(12) United States Patent
Marshall et al.

(10) Patent No.: US 7,037,894 B2
(45) Date of Patent: May 2, 2006

(54) STABILIZED PROTEINS

(75) Inventors: Christopher P. Marshall, Brooklyn, NY (US); Alexander Hoffman, Los Angeles, CA (US); Joseph P. Errico, Far Hills, NJ (US); Paul B. Marshall, Munich (DE)

(73) Assignee: Avatar Medical, LLC, Newark, NJ (US)

( * ) Notice: Subject to any disclaimer, the term of this patent is extended or adjusted under 35 U.S.C. 154(b) by 390 days.

(21) Appl. No.: 09/837,235

(22) Filed: Apr. 18, 2001

(65) Prior Publication Data

US 2002/0061549 A1 May 23, 2002

Related U.S. Application Data

(63) Continuation of application No. PCT/US00/28595, filed on Oct. 16, 2000.
(60) Provisional application No. 60/159,763, filed on Oct. 15, 1999.

(51) Int. Cl.
*A61K 38/00* (2006.01)
*A61K 38/43* (2006.01)
*C07K 1/00* (2006.01)
*C07K 16/00* (2006.01)
*C12N 9/00* (2006.01)

(52) U.S. Cl. .............. 514/12; 424/94.1; 424/130.1; 424/94.3; 530/350; 530/387.1; 530/388.21; 530/388.22; 530/388.24; 530/399; 435/183; 435/198; 514/2

(58) Field of Classification Search .............. 514/2, 514/12; 424/94.1, 94.3, 130.1, 192.1; 530/350, 530/387.1, 388.21, 388.22, 388.24, 399, 530/300, 387.9; 435/183, 198; 536/23.1, 536/23.2

See application file for complete search history.

(56) References Cited

U.S. PATENT DOCUMENTS

| 4,650,758 A | 3/1987 | Shaked et al. ............... 435/105 |
| 4,904,592 A | 2/1990 | Freeman et al. ............. 435/183 |
| 5,538,876 A | 7/1996 | Mutsaers et al. ........... 435/141 |
| 5,747,654 A | 5/1998 | Pastan et al. ............. 530/391.7 |

FOREIGN PATENT DOCUMENTS

| WO | WO 01/29247 | 4/2001 |
| WO | WO 01/54486 | 8/2001 |

OTHER PUBLICATIONS

Stachel et al., 1998, "Stabilization of a C7 Equatorial Gamma Turn in DMSO–d6 by a Ditryptophan Crosslink", Bioorganic and Medicinal Chemistry 6:1439–1446.

Malencik and Anderson, 1994, "Dityrosine Formation in Calmodulin: Conditions for Intermolecular Cross–Linking", Biochemistry 33:13363–13372.

Brown et al., 1995, "Highly Specific Oxidative Cross–Linking of Proteins Mediated by a Nickel–Peptide Complex", Biochemistry 34:4733–4739.

Fancy and Kodadek, 1999, "Chemistry for the analysis of protein–protein interactions: rapid and efficient cross–linking triggered by long wavelength light", PNAS USA 96:6020–6024.

Campbell et al., 1998, "Protein Cross–Linking Mediated by Metalloporphyrins", Biorg. And Medicinal Chem. 6:1301–7.

Galeazzi et al., 1999, "In vitro peroxidase oxidation induces stable dimmers of –amyloid (1–42) through dityrosine bridge formation", Amyloid: Int. J. Exp. Clin. Investig. 6:7–13.

Baudry et al., 1996, "Dityrosine bridge formation and thyroid hormone synthesis are tightly linked and are both dependent on N–glycans", FEBS Lett. 396:223–226.

Briza et al., 1994, "The sporulation–specific enzymes encoded by the DIT1 and DIT2 genes catalyze a two–step reaction leading to a soluble LL–dityrosine–containing precursor of the yeast spore wall", Proc. Natl. Acad. Sci. USA 91:4524–4528.

Briza et al., 1990, "Characterization of a DL–dityrosine–containing macromolecule from yeast ascospore walls", J. Biol. Chem. 265:15118–15123.

Briza et al., 1986, "Dityrosine is a prominent component of the yeast ascospore wall", J. Biol. Chem. 261:4288–4294.

DeVore and Gruebel, 1978, "Dityrosine in adhesive formed by the sea mussel, *Mytilus edulis*", Biochem. Biophys. Res. Comm. 80:993–999.

Downie et al. 1972, "An insoluble, dityrosine–containing protein from uterus", Biochim. Biophys. Acta 263:604–609.

(Continued)

*Primary Examiner*—Tekchand Saidha
(74) *Attorney, Agent, or Firm*—Jane M. Love; Wilmer Cutler Pickering Hale and Dorr LLP

(57) ABSTRACT

Isolated polypeptides or polypeptide chains are modified by di-tyrosine cross-linking such that the retain at least one functional activity. In one embodiment, the isolated polypeptide or polypeptide chains comprise at least one di-tyrosine cross-link, wherein at least one tyrosine of the di-tyrosine cross-link originates from a point mutation to tyrosine, and wherein the di-tyrosine cross-linked protein retains at least one function displayed by the protein in the absence of di-tyrosine cross-linking. In another embodiment, the di-tyrosine cross-linked polypeptide or polypeptide chain has enhanced stability compared to the same polypeptide or polypeptide chain in the absence of di-tyrosine cross-linking. A method for stabilization of a polypeptide or polypeptide complex, by the introduction of intra-polypeptide and/or inter-polypeptide di-tyrosine bonds, which simultaneously maintains the structure and function of the polypeptide or polypeptide complex is also described.

25 Claims, 26 Drawing Sheets

OTHER PUBLICATIONS

Figure 1A:
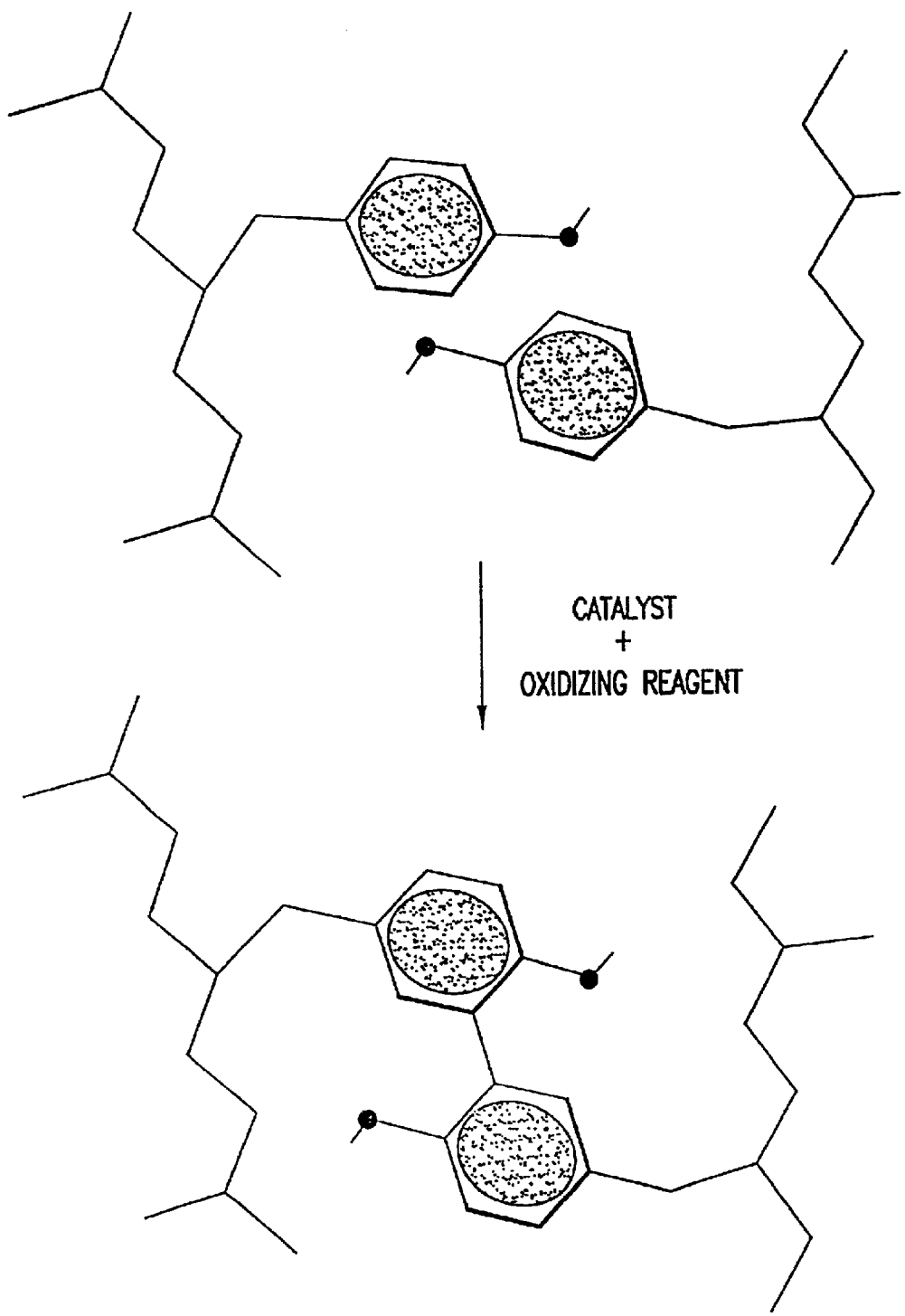
Figure 1B:
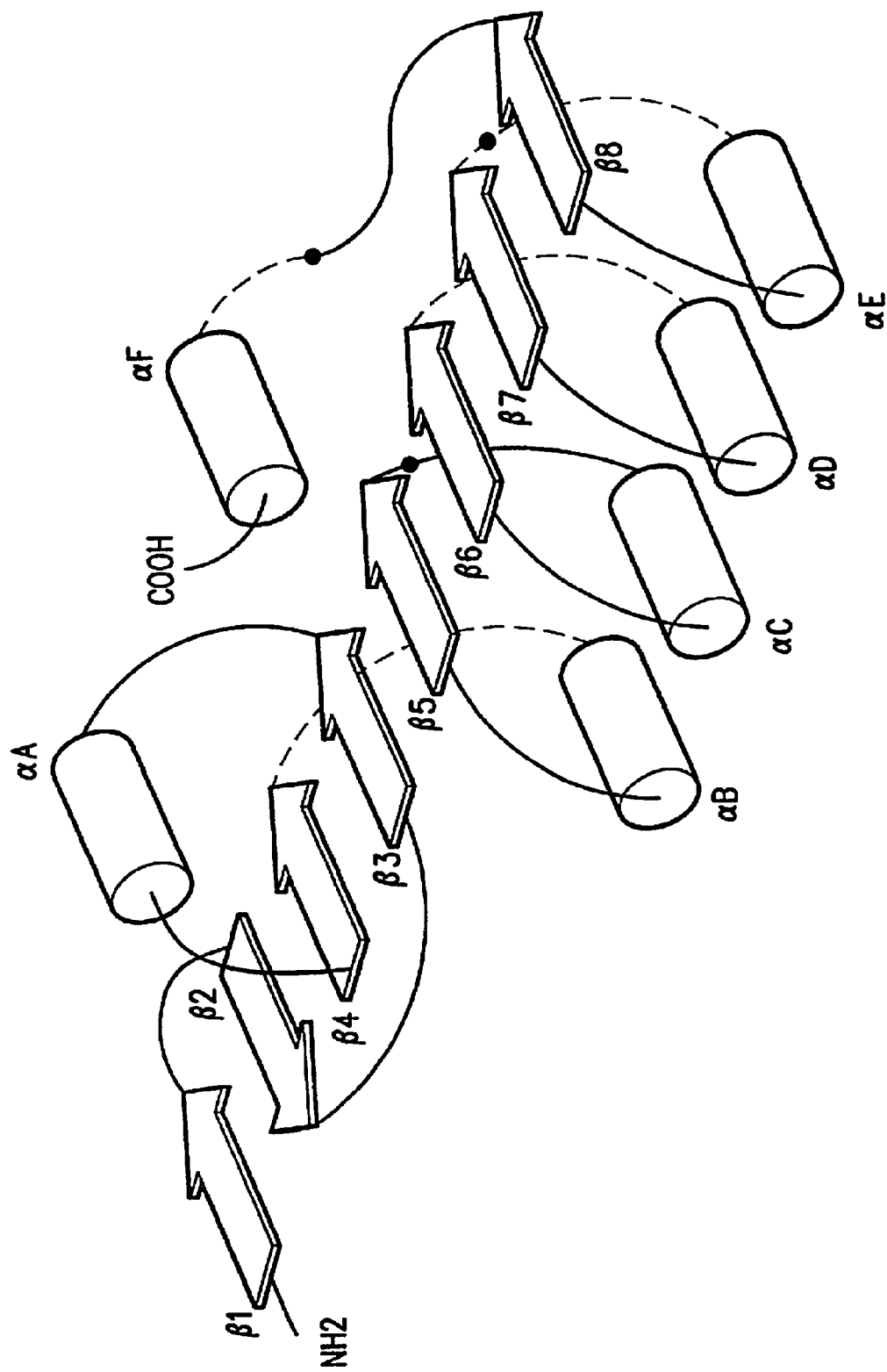
Figure 1C:
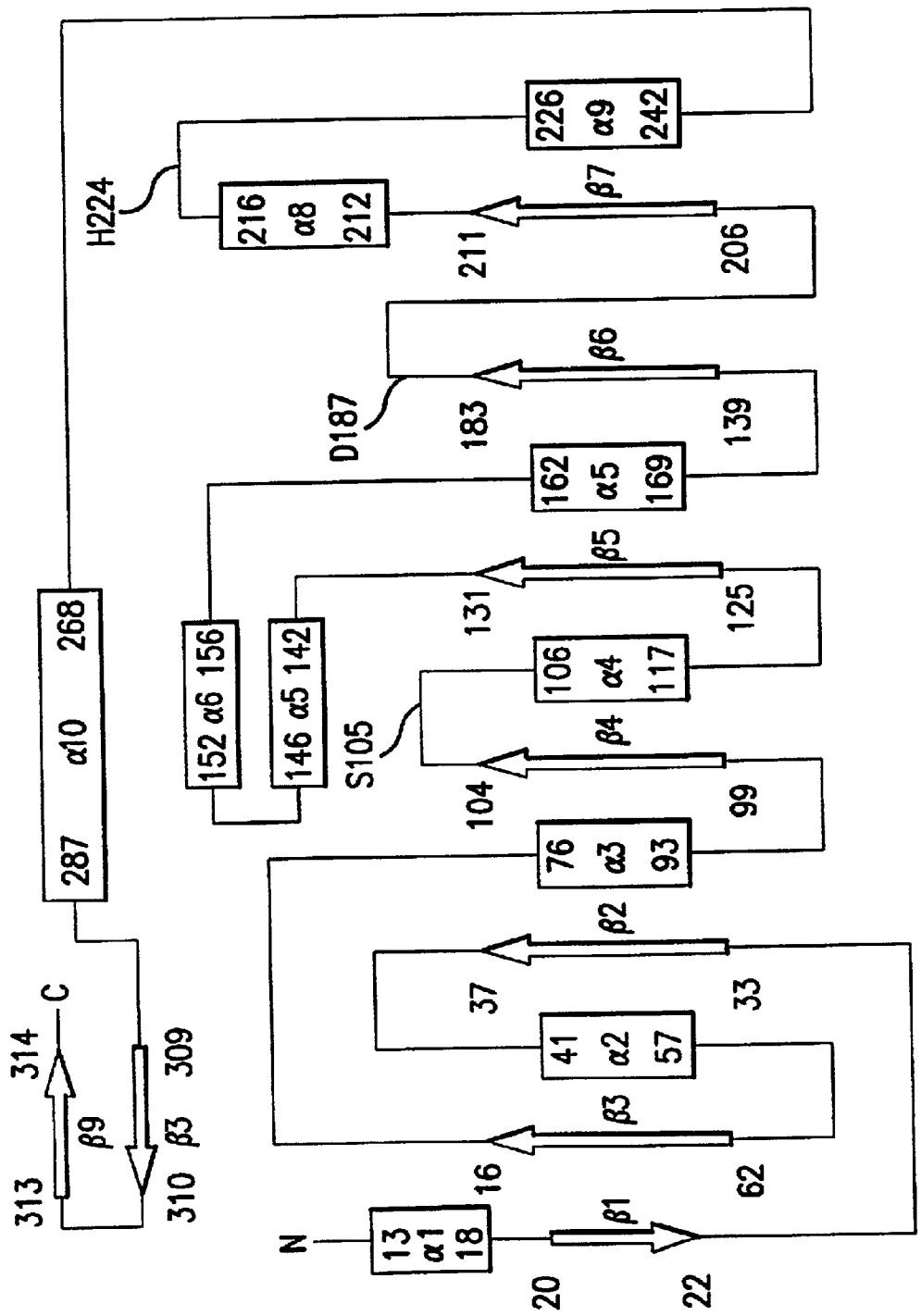

Fetterer et al., 1993, "Synthesis of tyrosine–derived cross–links in *Ascaris suum* cuticular proteins", J. Parasitol. 79:160–166.

Fetterer and Rhoads, 1990, "Tyrosine–derived cross–linking amino acids in the sheath of *Haemonchus contortus* infective larvae", J. Parasitol. 76:619–624.

Frater et al., 1960, "A role for thiol and disulphide groups in determining the rheological properties of dough made from wheaten flour", Nature 186:451–454.

Gmeiner and Seelos, 1989, "Phosphorylation of tyrosine prevents dityrosine formation in vitro", FEBS Lett. 255:395–397.

Grune et al., 2001, "Age–related changes in protein oxidation and proteolysis in mammalian cells", J. Gerontol. 56A:B459–B467.

Guptasarma and Balasubramanian, 1992, "Dityrosine formation in the proteins of the eye lens", Current Eye Res. 11:1121–1125.

Hensley et al., 1998, "Electrochemical analysis of protein nitrotyrosin and dityrosine in the Alzheimer brain indicates region–specific accumulation", J. Neurosci. 18:8126–8132.

Huggins et al., 1992, "Tyrosine and dityrosine concentrations in oxidized proteins and lens proteins with age", Annals NY Acad. Sci. 663:436–437.

Kanwar and Balasubramanian, 2000, "Structural studies on some dityrosine–cross–linked globular proteins: stability is weakened, but activity is not abolished", Biochem. 39:14976–14983.

Kanwar and Balasubramanian, 1999, "Structure and stability of the dityrosine–linked dimer of γB–crystallin", Exp. Eye Res. 68:773–784.

Kato et al., 1995, "Formation of protein–bound 3,4–dihydroxyphenylalanine in collagen types I and IV exposed to ultraviolet light", Photochem. Photobiol. 61:367–372.

Kay and Shapiro, 1987, "Ovoperoxidase assembly into the sea urchin fertilization envelope and dityrosine crosslinking", Devel. Biol. 121:325–334.

Keeley et al., 1969, "Dityrosine in a non–hydroxyproline, alkali–soluble protein isolated from chick aorta and bovine ligament", Biochem. Biophys. Res. Comm. 34:156–161.

LaBella et al., 1967, "Evidence for dityrosine in elastin", Biochem. Biophys. Res. Comm. 26:748–753.

Leonardi et al., 1994, "Presence of dityrosine bridges in thyroglobulin and their relationship with iodination", Biochem. Biophys. Res. Comm. 202:38–43.

Leeuwenburgh et al., 1999, "Oxidized amino acids in the urine of aging rats: potential markers for assessing oxidative stress in vivo", Am. J. Physiol. 276:R128–R135.

Li et al., 1996, "Involvement of peroxidase in chorion hardening in *Aedes aegypti*", Insect Biochem. Molec. Biol. 26:309–317.

Malanik and Ledvina, 1979, "The content of dityrosine in chick and rabbit aorta proteins", Connective Tissue Res. 6:235–240.

Malencik et al., 1996, "Dityrosine: preparation, isolation and analysis", Anal. Biochem. 242:202–213.

Michon et al., 1999, "Wheat prolamine crosslinking through dityrosine formation catalyzed by peroxidases: improvement in the modification of a poorly accessible substrate by "indirect" catalysis", Biotechnol. Bioeng. 63:449–458.

Nomura et al., 1990, "Pulcherosine, a novel tyrosine–derived, trivalent cross–linking amino acid from the fertilization envelope of sea urchin embryo", Biochem. 29:4525–4534.

Onorato et al., 1998, "Immunohistochemical and ELISA assays for biomarkers of oxidative stress in aging and disease", Annals NY Acad. Sci. 854:277–290.

Pandey and Aronson, 1979, "Properties of the *Bacillus subtilis* spore coat", J. Bacteriol. 137:1208–1218.

Raven et al., 1971, "Occurrence of dityrosine in Tussah silk fibroin and keratin", Biochim. Biophys. Acta 251:96–99.

Shewry et al., 1992, "High molecular weight subunits of wheat glutenin", J. Cereal Sci. 15:105–120.

Smail et al., 1995, "*Candida albicans* cell walls contain the fluorescent cross–linking amino acid dityrosine", Infect. Immun. 63:4078–4083.

Sobel and Ajie, 1992, "Modification in amino acids of Dead Sea scroll parchments", Free Radical Biol. Med. 13:701–702.

Souza et al., 2000, "Dityrosine cross–linking promotes formation of a stable α–synuclein polymers", J. Biol. Chem. 275:18344–18349.

Spangler and Erman, 1986, "Cytochrome c peroxidase compound I: formation of covalent protein crosslinks during the endogenous reduction of the active site", Biochim. Biophys. Acta 872:155–157.

Sullivan et al., 1940, "The action of oxidizing and reducing agents on flour", Cereal Chem. 17:507–528.

Tilley et al., 2001, "Tyrosine cross–links: molecular basis of gluten structure and function," J. Agric. Food Chem. 49: 2627–2632.

Totsune et al., 1993, "Chemiluminescence from bamboo shoot cut", Biochem. Biophys. Res. Comm. 194:1025–1029.

Waffenschmidt et al., 1993, "Isodityrosine cross–linking mediates insolubilization of cell walls in *Chlamydomonas*", Plant Cell 5:809–820.

Waykole and Heidemann, 1976, "Dityrosine in collagen", Connective Tissue Res. 4:219–222.

Wells–Knecht et al., 1993, "Oxidized amino acids in lens protein with age", J. Biol. Chem. 268:12348–12352.

Aeschbach et al., 1976, "Formation of Dityrosine Cross–Links in Proteins by Oxidation of Tyrosine Residues," Biochim. Biophys. Acta 439, 292–301.ikas.

Bodaness et al., 1984, "An Analysis of the $H_2O_2$–Mediated Crosslinking of Lens Crytallins Catalyzed by the Heme–Undecapeptide from Cytochrome c," Arch. Biochem. Biophys. 231 (2), 461–469.

Brown et al., 1998, "Determining Protein–Protein Interactions by Oxidative Cross–Linking of a Glycine–Glycine–Histidine Fusion Protein," Biochemistry 37, 4397–4406.

Campbell et al., 1998, "Protein Cross–Linking Mediated by Metalloporphyrins," Bioorg. Med. Chem. 6, 1301–1307.

Fancy & Kodadek, 1997, "Site–Directed Oxidative Protein Crosslinking," Tetrahedron. 53 (35), 11953–11960.

Fancy & Kodadek, 1999, "Chemistry for the Analysis of Protein–Protein Interactions: Rapid and Efficient Cross–Linking Triggered by Long Wavelength Light," Proc. Natl. Acad. Sci. USA 96, 6020–6024.

Gmeiner & Seelos, 1989, "Phosphorylation of Tyrosine Prevents Dityrosine Formation In Vitro," FEBS Lett. 255 (2), 395–397.

Govardhan, 1999, "Crosslinking of Enzymes for Improved Stability and Performance," Curr. Opin. Biotech. 10, 331–335.

Helms et al., 1998, "Flexibility Involving the Intermolecular Dityrosyl Cross–Links of Enzymatically Polymerized Calmodulin," Biochemistry 37, 8378–8384.

Kanwar & Balasubramanian, 1999, "Structure & Stability of the Dityrosine–Linked Dimer of gB–Crystallin," Exp. Eye Res. 698, 773–784.

Kanwar & Balasubramanian, 2000, "Structural Studies on Some Dityrosine–Cross–Linked Globular Proteins: Stability Is Weakened, But Activity Is Not Abolished," Biochemistry 39, 14976–14983.

Lardinois et al., 1999, "Spin Trapping and Protein Cross–Linking of the Lactoperoxidase Protein Radical," J. Biol. Chem. 274 (50), 35441–35448.

Malencik & Anderson, 1987, "Dityrosine Formation in Calmodulin," Biochemistry 26, 695–704.

Malencik & Anderson, 1991, "Fluorometric Characterization of Dityrosine: Complex Formation with Boric Acid and Borate Ion," Biochem. Biophys. Res. Commun. 178 (1), 60–67.

Malencik & Anderson, 1994, "Dityrosine Formation in Calmodulin: Conditions for Intermolecular Cross–Linking," Biochemistry 33, 13363–13372.

Malencik & Anderson, 1996, Dityrosine Formation in Calmodulin: Cross–Linking and Polymerization Catalyzed by *Arthromyces* Peroxidase, Biochemistry 35, 4375–4386.

LIGHT CHAIN (L)

| CHAIN | K&W | ATOM | AMINO ACID | x COORDINATE | y COORDINATE | z COORDINATE |
|---|---|---|---|---|---|---|
| L | 1 | N | ASP | 2.37 | −5.00 | −27.24 |
| L | 1 | Cα | ASP | 2.98 | −3.78 | −26.64 |
| L | 1 | C | ASP | 1.91 | −2.70 | −26.52 |
| L | 1 | O | ASP | 1.33 | −2.29 | −27.53 |
| L | 1 | Cβ | ASP | 4.14 | −3.29 | −27.53 |
| L | 1 | Cγ | ASP | 5.18 | −2.49 | −26.76 |
| L | 1 | Oδ1 | ASP | 4.86 | −1.38 | −26.27 |
| L | 1 | Oδ2 | ASP | 6.34 | −2.97 | −26.65 |
| L | 2 | N | ILE | 1.63 | −2.26 | −25.30 |
| L | 2 | Cα | ILE | 0.60 | −1.24 | −25.07 |
| L | 2 | C | ILE | 1.19 | 0.15 | −24.94 |
| L | 2 | O | ILE | 2.14 | 0.35 | −24.94 |
| L | 2 | Cβ | ILE | −0.21 | −1.52 | −23.78 |
| L | 2 | Cγ1 | ILE | −0.90 | −2.88 | −23.86 |
| L | 2 | Cγ2 | ILE | −1.24 | −0.43 | −23.58 |
| L | 2 | Cδ1 | ILE | −1.66 | −3.26 | −22.59 |
| L | 3 | . | . | . | . | . |
| . | . | . | . | . | . | . |
| . | . | . | . | . | . | . |

FIG.5A

HEAVY CHAIN (H)

| CHAIN | K&W | ATOM | AMINO ACID | x COORDINATE | y COORDINATE | z COORDINATE |
|---|---|---|---|---|---|---|
| H | 1 | N | GLU | 11.12 | −2.19 | 9.00 |
| H | 1 | Cα | GLU | 11.43 | −1.08 | 8.05 |
| H | 1 | C | GLU | 11.93 | −1.63 | 6.71 |
| H | 1 | O | GLU | 13.10 | −1.98 | 6.56 |
| H | 1 | Cβ | GLU | 12.47 | −0.12 | 8.66 |
| H | 1 | Cγ | GLU | 13.82 | −0.75 | 9.05 |
| H | 1 | Cδ | GLU | 13.70 | −1.77 | 10.17 |
| H | 1 | Oε1 | GLU | 13.38 | −1.36 | 11.31 |
| H | 1 | Oε2 | GLU | 13.94 | −2.97 | 9.92 |
| H | 2 | N | ILE | 11.02 | −1.70 | 5.74 |
| H | 2 | Cα | ILE | 11.36 | −2.24 | 4.42 |
| H | 2 | C | ILE | 12.10 | −1.22 | 3.59 |
| H | 2 | O | ILE | 11.77 | −0.04 | 3.64 |
| H | 2 | Cβ | ILE | 10.11 | −2.68 | 3.62 |
| H | 2 | Cγ1 | ILE | 9.31 | −3.73 | 4.39 |
| H | 2 | Cγ2 | ILE | 10.52 | −3.22 | 2.28 |
| H | 3 | Cδ1 | ILE | 8.49 | −3.17 | 5.55 |
| H | 3 | . | . | . | . | . |
| . | . | . | . | . | . | . |
| . | . | . | . | . | . | . |

FIG.5B

Fv FRAGMENT 1

| Ch | K&W | At | AA | x | y | z | | | | | |
|----|-----|----|----|----|----|----|---|---|---|---|---|
| | | | | | | | Ch | L | L | L | L | L |
| | | | | | | | K&W | 1 | 2 | 3 | 4 | 5 |
| | | | | | | | At | Cα | Cα | Cα | Cα | Cα |
| | | | | | | | AA | Asp | Ile | . | . | . |
| | | | | | | | x | 2.98 | 0.60 | . | . | . |
| | | | | | | | y | −3.78 | −1.24 | . | . | . |
| | | | | | | | z | −26.64 | −25.07 | . | . | . |
| H | 1 | Cα | Glu | 11.43 | −1.08 | 8.05 | | 35.80 | 34.84 | . | . | . |
| H | 2 | Cα | Ile | 11.36 | −2.24 | 4.42 | | 32.21 | 31.42 | . | . | . |
| H | 3 | Cα | . | . | . | . | | . | . | . | . | . |
| H | 4 | Cα | . | . | . | . | | . | . | . | . | . |
| H | 5 | Cα | . | . | . | . | | . | . | . | . | . |

FIG.6A

Fv FRAGMENT 2

| Ch | K&W | At | AA | x | y | z | | | | | |
|----|-----|----|----|----|----|----|---|---|---|---|---|
| | | | | | | | Ch | L | L | L | L | L |
| | | | | | | | K&W | 1 | 2 | 3 | 4 | 5 |
| | | | | | | | At | Cα | Cα | Cα | Cα | Cα |
| | | | | | | | AA | Glu | Ser | . | . | . |
| | | | | | | | x | 35.61 | 31.94 | . | . | . |
| | | | | | | | y | 83.10 | 83.89 | . | . | . |
| | | | | | | | z | 56.99 | 56.85 | . | . | . |
| H | 1 | Cα | Glu | 10.23 | 61.09 | 64.74 | | 34.48 | 32.46 | . | . | . |
| H | 2 | Cα | Val | 13.63 | 62.72 | 65.19 | | 31.07 | 29.20 | . | . | . |
| H | 3 | Cα | . | . | . | . | | . | . | . | . | . |
| H | 4 | Cα | . | . | . | . | | . | . | . | . | . |
| H | 5 | Cα | . | . | . | . | | . | . | . | . | . |

FIG.6B

Fv FRAGMENT 3

| Ch | K&W | At | AA | x | y | z |
|---|---|---|---|---|---|---|
| H | 1 | Cα | GLN | 26.71 | 9.76 | 10.88 |
| H | 2 | Cα | Val | 27.45 | 8.61 | 7.34 |
| H | 3 | Cα | . | . | . | . |
| H | 4 | Cα | . | . | . | . |
| H | 5 | Cα | . | . | . | . |

| Ch | L | L | L | L | L |
|---|---|---|---|---|---|
| K&W | 1 | 2 | 3 | 4 | 5 |
| At | Cα | Cα | Cα | Cα | Cα |
| AA | Glu | Ser | . | . | . |
| x | 19.56 | 19.09 | . | . | . |
| y | −13.02 | −15.06 | . | . | . |
| z | −15.86 | −12.67 | . | . | . |
|  | 35.84 | 35.05 | . | . | . |
|  | 32.69 | 32.11 | . | . | . |
|  | . | . | . | . | . |
|  | . | . | . | . | . |
|  | . | . | . | . | . |

FIG. 6C

| RESIDUE PAIRS | | AVERAGE | St.DEV. | MAX | MIN | MEDIAN |
|---|---|---|---|---|---|---|
| H1 | L1 | 35.38 | 0.78 | 35.84 | 34.48 | 35.80 |
| H1 | L2 | 34.12 | 1.44 | 35.05 | 32.46 | 34.84 |
| H1 | L3 | . | . | . | . | . |
| H1 | L4 | . | . | . | . | . |
| . | . | . | . | . | . | . |
| H1 | L106 | . | . | . | . | . |
| H2 | L1 | 31.99 | 0.83 | 32.69 | 31.07 | 32.21 |
| H2 | L2 | 30.91 | 1.52 | 32.11 | 29.20 | 31.41 |
| H2 | L3 | . | . | . | . | . |
| H2 | L4 | . | . | . | . | . |
| . | . | . | . | . | . | . |
| H2 | L106 | . | . | . | . | . |
| H3 | L1 | . | . | . | . | . |

FIG.7A

| RESIDUE PAIRS | | AVERAGE | St.DEV. | MAX | MIN | MEDIAN |
|---|---|---|---|---|---|---|
| H1 | L1 | 35.09 | 1.56 | 37.37 | 31.23 | 35.54 |
| H1 | L2 | 34.00 | 1.87 | 37.36 | 29.92 | 34.38 |
| H1 | L3 | . | . | . | . | . |
| H1 | L4 | . | . | . | . | . |
| . | . | . | . | . | . | . |
| H1 | L106 | . | . | . | . | . |
| H2 | L1 | 32.26 | 1.57 | 36.71 | 30.34 | 32.14 |
| H2 | L2 | 31.32 | 1.99 | 36.77 | 29.20 | 31.11 |
| H2 | L3 | . | . | . | . | . |
| H2 | L4 | . | . | . | . | . |
| . | . | . | . | . | . | . |
| H2 | L106 | . | . | . | . | . |
| H3 | L1 | . | . | . | . | . |

FIG.7B

| Ch | K&W | At | AA | x | y | z |
|---|---|---|---|---|---|---|
| H | 1 | Cβ | GLU | 12.47 | -0.12 | 8.66 |
| H | 2 | Cβ | ILE | 10.11 | -2.68 | 3.62 |
| H | 3 | Cβ | . | . | . | . |
| H | 4 | Cβ | . | . | . | . |
| H | 5 | Cβ | . | . | . | . |

| Ch | L | L | L | L | L |
|---|---|---|---|---|---|
| K&W | 1 | 2 | 3 | 4 | 5 |
| At | Cβ | Cβ | Cβ | Cβ | Cβ |
| AA | ASP | ILE | . | . | . |
| x | 4.14 | -0.21 | . | . | . |
| y | -3.29 | -1.52 | . | . | . |
| z | -27.53 | -23.78 | . | . | . |
|  | 37.27 | 34.85 | . | . | . |
|  | 31.73 | 29.30 | . | . | . |
|  | . | . | . | . | . |

FIG. 8

| ALPHA DISTANCES | | | | | | Ch | L | L | L | L | L |
| --- | --- | --- | --- | --- | --- | --- | --- | --- | --- | --- | --- |
| | | | | | | K&W | 1 | 2 | 3 | 4 | 5 |
| | | | | | | At | Cα | Cα | Cα | Cα | Cα |
| | | | | | | AA | ASP | ILE | . | . | . |
| | | | | | | x | 2.98 | 0.60 | . | . | . |
| | | | | | | y | −3.78 | −1.24 | . | . | . |
| | | | | | | z | −26.64 | −25.07 | . | . | . |
| Ch | K&W | At | AA | x | y | z | | | | | |
| H | 1 | Cα | GLU | 11.43 | −1.08 | 8.05 | 35.80 | 34.84 | . | . | . |
| H | 2 | Cα | ILE | 11.36 | −2.24 | 4.42 | 32.21 | 31.42 | . | . | . |
| H | 3 | Cα | . | . | . | . | . | . | . | . | . |
| H | 4 | Cα | . | . | . | . | . | . | . | . | . |
| H | 5 | Cα | . | . | . | . | . | . | . | . | . |

FIG.9A

| BETA DISTANCES | | | | | | Ch | L | L | L | L | L |
| --- | --- | --- | --- | --- | --- | --- | --- | --- | --- | --- | --- |
| | | | | | | K&W | 1 | 2 | 3 | 4 | 5 |
| | | | | | | At | Cβ | Cβ | Cβ | Cβ | Cβ |
| | | | | | | AA | ASP | ILE | . | . | . |
| | | | | | | x | 4.14 | −0.21 | . | . | . |
| | | | | | | y | −3.29 | −1.52 | . | . | . |
| | | | | | | z | −27.53 | −23.78 | . | . | . |
| Ch | K&W | At | AA | x | y | z | | | | | |
| H | 1 | Cβ | GLU | 12.47 | −0.12 | 8.66 | 37.27 | 34.85 | . | . | . |
| H | 2 | Cβ | ILE | 10.11 | −2.68 | 3.62 | 31.73 | 29.30 | . | . | . |
| H | 3 | Cβ | . | . | . | . | . | . | . | . | . |
| H | 4 | Cβ | . | . | . | . | . | . | . | . | . |
| H | 5 | Cβ | . | . | . | . | . | . | . | . | . |

FIG.9B

| DIFFERENCE | | | Ch K&W | L 1 | L 2 | L 3 | L 4 | L 5 |
|---|---|---|---|---|---|---|---|---|
| | | | AA | ASP | ILE | . | . | . |
| DIFFERENCES BETWEEN RESIDUE PAIR ALPHA- AND BETA CARBON DISTANCES | | | | | | . | . | . |
| | | | | | | . | . | . |
| | | | | | | . | . | . |
| Ch | K&W | AA | | | | | | |
| H | 1 | GLU | | −1.47 | −0.01 | . | . | . |
| H | 2 | ILE | | 0.48 | 2.10 | . | . | . |
| H | 3 | . . . . | | . | . | . | . | . |
| H | 4 | . . . . | | . | . | . | . | . |
| H | 5 | . . . . | | . | . | . | . | . |

FIG.9C

|  |  | L1 | L2 | L3 | L4 | L5 | . | . |
|---|---|---|---|---|---|---|---|---|
| Fv FRAGMENT 1 | H1 | −1.47 | −0.01 | . | . | . | . | . |
|  | H2 | 0.48 | 2.10 | . | . | . | . | . |
|  | H3 | . | . | . | . | . | . | . |
|  | H4 | . | . | . | . | . | . | . |
|  | . | . | . | . | . | . | . | . |
|  | . | L1 | L2 | L3 | L4 | L5 | . | . |
| Fv FRAGMENT 2 | H1 | −1.61 | 0.46 | . | . | . | . | . |
|  | H2 | 0.18 | 2.04 | . | . | . | . | . |
|  | H3 | . | . | . | . | . | . | . |
|  | H3 | . | . | . | . | . | . | . |
|  | . | . | . | . | . | . | . | . |
|  | . | L1 | L2 | L3 | L4 | L5 | . | . |
| Fv FRAGMENT 3 | H1 | 0.92 | 1.59 | . | . | . | . | . |
|  | H2 | 0.69 | 1.31 | . | . | . | . | . |
|  | H3 | . | . | . | . | . | . | . |
|  | H3 | . | . | . | . | . | . | . |
|  | . | . | . | . | . | . | . | . |
|  | . | L1 | L2 | L3 | L4 | L5 | . | . |
| Fv FRAGMENT 4 | H1 | . | . | . | . | . | . | . |

FIG.10

| RESIDUE PAIRS | | AVERAGE | Strd.DEV. | MAX | MIN | MEDIAN |
|---|---|---|---|---|---|---|
| H1 | L1 | −0.72 | 1.42 | 0.92 | −1.61 | −1.47 |
| H1 | L2 | 0.68 | 0.82 | 1.59 | −0.01 | 0.46 |
| H1 | L3 | . | . | . | . | . |
| H1 | L4 | . | . | . | . | . |
| . | . | . | . | . | . | . |
| . | . | . | . | . | . | . |
| H1 | L106 | . | . | . | . | . |
| H2 | L1 | 0.45 | 0.26 | 0.69 | 0.18 | 0.48 |
| H2 | L2 | 0.68 | 0.82 | 1.59 | −0.01 | 0.46 |
| H2 | L3 | . | . | . | . | . |
| H2 | L4 | . | . | . | . | . |
| . | . | . | . | . | . | . |
| . | . | . | . | . | . | . |
| H2 | L106 | . | . | . | . | . |
| H3 | L1 | . | . | . | . | . |

FIG.11A

| RESIDUE PAIRS | | AVERAGE | Strd.DEV. | MAX | MIN | MEDIAN |
|---|---|---|---|---|---|---|
| H1 | L1 | −0.68 | 1.04 | 0.92 | −2.20 | 0.83 |
| H1 | L2 | 0.34 | 0.82 | 2.37 | −0.54 | 0.09 |
| H1 | L3 | . | . | . | . | . |
| H1 | L4 | . | . | . | . | . |
| . | . | . | . | . | . | . |
| . | . | . | . | . | . | . |
| H1 | L106 | . | . | . | . | . |
| H2 | L1 | 0.74 | 0.69 | 1.83 | −0.18 | 0.59 |
| H2 | L2 | 1.78 | 0.50 | 2.55 | 0.75 | 1.94 |
| H2 | L3 | . | . | . | . | . |
| H2 | L4 | . | . | . | . | . |
| . | . | . | . | . | . | . |
| . | . | . | . | . | . | . |
| H2 | L106 | . | . | . | . | . |
| H3 | L1 | . | . | . | . | . |

FIG.11B

| Res. | AA | F | AA | F | AA | F | AA | F | AA | F | AA | F |
|---|---|---|---|---|---|---|---|---|---|---|---|---|
| 1 | Glu | 58 | Glu | 24 | Asp | 3 | Glu | 3 | Gly | 2 | Ala | 1 |
| 2 | Val | 99 | Ile | 2 | Ala | 1 | Glu | 1 | Met | 1 | – | – |
| 3 | Gln | 90 | Thr | 5 | Glu | 3 | His | 2 | Leu | 2 | Lys | 2 |
| 4 | Leu | 101 | Val | 3 | – | – | – | – | – | – | – | – |

FIG.12A

| Amino Acid | van der Waals volumes [Å$^3$] | Hydrophobicity |
|---|---|---|
| Ala | 67 | 0.62 |
| Arg | 148 | −2.50 |
| Asn | 96 | −0.78 |
| Asp | 91 | −0.90 |
| Cys | 86 | 0.29 |
| Gln | 114 | −0.85 |
| Glu | 109 | −0.79 |
| Gly | 48 | 0.30 |
| His | 118 | −0.40 |
| Ile | 124 | 1.40 |
| Leu | 124 | 1.10 |
| Lys | 135 | −1.50 |
| Met | 124 | 0.64 |
| Phe | 135 | 1.20 |
| Pro | 90 | 0.12 |
| Ser | 73 | −0.18 |
| Thr | 93 | −0.05 |
| Trp | 163 | 0.81 |
| Tyr | 141 | 0.26 |
| Val | 105 | 1.10 |

FIG.12B

| Res. | AA | F | AA | F | AA | F | AA | F | AA | F | AA | F |
|---|---|---|---|---|---|---|---|---|---|---|---|---|
| 1 | 109 | 61 | 109 | 24 | 91 | 3 | 48 | 2 | 67 | 1 | – | – |
| 2 | 105 | 99 | 124 | 2 | 67 | 1 | 109 | 1 | 124 | 1 | – | – |
| 3 | 114 | 90 | 93 | 5 | 109 | 3 | 118 | 2 | 124 | 2 | 135 | 2 |
| 4 | 124 | 101 | 105 | 3 | – | – | – | – | – | – | – | – |

FIG.12C

VAN DER WAALS VOLUMES

| CHAIN | K&W | CONS. | WEIGHTED AVERAGE | StDev. | UNWEIGHTED AVERAGE | StDev. |
|---|---|---|---|---|---|---|
| H | 1 | Glu | 108 | 11 | 90 | 27 |
| H | 2 | Val | 105 | 5 | 106 | 23 |
| H | 3 | Gln | 114 | 6 | 116 | 14 |
| H | 4 | Leu | 123 | 3 | 115 | 13 |

FIG.13A

HYDROPHOBICITY

| CHAIN | K&W | CONS. | WEIGHTED AVERAGE | StDev. | UNWEIGHTED AVERAGE | StDev. |
|---|---|---|---|---|---|---|
| H | 1 | Glu | −0.77 | 0.24 | −0.37 | 0.72 |
| H | 2 | Val | 1.08 | 0.20 | 0.59 | 0.84 |
| H | 3 | Gln | −0.78 | 0.33 | −0.42 | 0.89 |
| H | 4 | Leu | 1.10 | 0.00 | 1.10 | 0.00 |

FIG.13B

C. Antarctica Lipase B Nucleotide and Amino Acid Sequence

```
           10          20         30         40         50         60
ctaccttccggttcggaccctgcctttccgcagcccaagtcggtgctcgatgcgggtctg
 L   P   S   G   S   D   P   A   F   S   Q   P   K   S   V   L   D   A   G   L
           70          80         90        100        110        120
acctgccagggtgcttcgccatcctcggtctccaaacccatccttctcgtccccggaacc
 T   C   Q   G   A   S   P   S   S   V   S   K   P   I   L   L   V   P   G   T
          130         140        150        160        170        180
ggcaccacaggtccacagtcgttcgactcgaactggatcccctctcaacgcagttgggt
 G   T   T   G   P   Q   S   F   D   S   N   W   I   P   L   S   T   Q   L   G
          190         200        210        220        230        240
tacacaccctgctggatctcaccccgccgttcatgctcaacgacacccaggtcaacacg
 Y   T   P   C   W   I   S   P   P   F   M   L   N   D   T   Q   V   N   T
          250         260        270        280        290        300
gagtacatggtcaacgccatcaccgcgctctacgctggttcgggcaacaacaagcttccc
 E   Y   M   V   N   A   I   T   A   L   Y   A   G   S   G   N   N   K   L   P
          310         320        330        340        350        360
gtgcttacctggtcccagggtggtctggttgcacagtggggtctgaccttcttccccagt
 V   L   T   W   S   Q   G   G   L   V   A   Q   W   G   L   T   F   F   P   S
          370         380        390        400        410        420
atcaggtccaaggtcgatcgacttatggccttcgcgcccgactacaagggcaccgtcctc
 I   R   S   K   V   D   R   L   M   A   F   A   P   D   Y   K   G   T   V   L
          430         440        450        460        470        480
gccggccctctcgatgcactcgcggttagtgcacctccgtatggcagcaaaccaccggt
 A   G   P   L   D   A   L   A   V   S   A   P   S   V   W   Q   Q   T   T   G
          490         500        510        520        530        540
tcggcactcaccaccgcactccgaaacgcaggtggtctgacccagatcgtgcccaccacc
 S   A   L   T   T   A   L   R   N   A   G   L   T   Q   I   V   P   T   T
          550         560        570        580        590        600
aacctctactcggcgaccgacgagatcgttcagcctcaggtgtccaactcgccactcgac
 N   L   Y   S   A   T   D   E   I   V   Q   P   Q   V   S   N   S   P   L   D
          610         620        630        640        650        660
tcatcctacctcttcaacggaaagaacgttcaggcacaggccgtgtgtgggccgctgttc
 S   S   Y   L   F   N   G   K   N   V   Q   A   Q   A   V   C   G   P   L   F
          670         680        690        700        710        720
gtcatcgaccatgcaggctcgctcacctcgcagttctcctacgtcgtcggtcgatccgcc
 V   I   D   H   A   G   S   L   T   S   Q   F   S   Y   V   V   G   R   S   A
          730         740        750        760        770        780
ctgcgctccaccacgggccaggctcgtagtgcagactatggcattacggactgcaaccct
 L   R   S   T   T   G   Q   A   R   S   A   D   Y   G   I   T   D   C   N   P
          790         800        810        820        830        840
cttcccgccaatgatctgactcccgagcaaaaggtcgccgcggctgcgctcctggcgccg
 L   P   A   N   D   L   T   P   E   Q   K   V   A   A   A   L   L   A   P
          850         860        870        880        890        900
gcagctgcagccatcgtggcgggtccaaagcagaactgcgagcccgacctcatgccctac
 A   A   A   I   V   A   G   P   K   Q   N   C   E   P   D   L   M   P   Y
          910         920        930        940        950
gcccgcccctttgcagtaggcaaaaggacctgctcaggcatcgtcacccctga(SEQ ID NO: 1)
 A   R   P   F   A   V   G   K   R   T   C   S   G   I   V   T   P   *  (SEQ ID NO: 2)
```

FIG. 15A

PCR Oligos for *Candida antarctica* Lipase B

*Oligos for pPal-CALB*

Primer A: 5'atg gga att cca tca tca tca tca cag cag cgg cct acc ttc cgg ttc gga ccc3' (SEQ ID NO: 3)

Primer B: 5'cta ttg gcg gcc gct tat cag ggg gtg acg atg ccg g3' (SEQ ID NO: 4)

*Oligos for Point Mutations (made in pPal-CALB)*

M1- F9Y primer M1P: 5'atg gga att cca tca tca tca tca cag cag cgg cct acc ttc cgg ttc gga ccc tgc ctA ttc gc3' (SEQ ID NO: 5)

M2- W52Y

Primer M2F: 5'cga ctc gaa ctA Cat ccc cct ctc3' (SEQ ID NO: 6)

Primer M2R: 5'gag agg ggg atO Tag ttc gag tcg3' (SEQ ID NO: 7)

M3- F117Y

Primer M3F: 5'ggg tctg acc tAc ttc ccc agt atc3' (SEQ ID NO: 8)

Primer M3R: 5'gat act ggg gaa gTa ggt cag acc c3' (SEQ ID NO: 9)

*Oligos for pYal-CALB*

Primer C:

5'- cgA Tga gat ttc ctt caa ttt -3'
(SEQ ID NO:10)

Primer D:

5'-5'tct aga aag gtg gcg gcc gcc-3' (SEQ ID NO: 11)

*Oligos for error-prone PCR*

Primer E:
5'gaa gct gga ttc cat cat cat c3'
(SEQ ID NO: 12)

Primer D:
5'-5'tct aga aag gtg gcg gcc gcc-3' (SEQ ID NO: 13)

FIG. 15B

Subtilisin E Nucleotide and Amino Acid Sequence

```
         10         20         30         40         50         60         70         80
atgtctgtgcaggctgccggaaaaagcagtacagaaaagaaatacattgtcggatttaaacagacaatgagtgccatgag
 M  S  V  Q  A  A  G  K  S  S  T  E  K  K  Y  I  V  G  F  K  Q  T  M  S  A  M  S
         90        100        110        120        130        140        150        160
ttccgccaagaaaaaggatgttatttctgaaaaaggcggaaaggttcaaaagcaatttaagtatgttaacgcggccgcag
 S  A  K  K  K  D  V  I  S  E  K  G  G  K  V  Q  K  Q  F  K  Y  V  N  A  A  A
        170        180        190        200        210        220        230        240
caacattggatgaaaaagctgtaaaagaattgaaaaaagatccgagcgttgcatatgtggaagaagatcatattgcacat
 A  T  L  D  E  K  A  V  K  E  L  K  K  D  P  S  V  A  Y  V  E  D  H  I  A  H
        250        260        270        280        290        300        310        320
gaatatgcgcaatctgttccttatggcatttctcaaattaaagcgccggctcttcactctcaaggctacacaggctctaa
 E  Y  A  Q  S  V  P  Y  G  I  S  Q  I  K  A  P  A  L  H  S  Q  G  Y  T  G  S  N
        330        340        350        360        370        380        390        400
cgtaaaagtagctgttatcgacagcggaattgactcttctcatcctgacttaaacgtcagaggcggagcaagcttcgtac
 V  K  V  A  V  I  D  S  G  I  D  S  S  H  P  D  L  N  V  R  G  G  A  S  F  V
        410        420        430        440        450        460        470        480
cttctgaaacaaacccataccaggacggcagttctcacggtacgcatgtagccggtacgattgccgctcttaataactca
 P  S  E  T  N  P  Y  Q  D  G  S  S  H  G  T  H  V  A  G  T  I  A  A  L  N  N  S
        490        500        510        520        530        540        550        560
atcggtgttctgggcgttagcccaagcgcatcattatatgcagtaaaagtgcttgattcaacaggaagcggccaatatag
 I  G  V  L  G  V  S  P  S  A  S  L  Y  A  V  K  V  L  D  S  T  G  S  G  Q  Y  S
        570        580        590        600        610        620        630        640
ctggattattaaaggcattgagtgggccatttccaacaatatggatgttatcaacatgagcttggcggaccctactggtt
 W  I  I  N  G  I  E  W  A  I  S  N  N  M  D  V  I  N  M  S  L  G  G  P  T  G
        650        660        670        680        690        700        710        720
ctacagcgctgaaaacagtcgttgacaaagccgtttccagcggtatcgtcgttgctgccgcagccggaaacgaaggttca
 S  T  A  L  K  T  V  V  D  K  A  V  S  S  G  I  V  V  A  A  A  A  G  N  E  G  S
        730        740        750        760        770        780        790        800
tccggaagcacaagcacagtcggctaccctgcaaaatatccttctactattgcagtaggtgcggtaaacagcagcaacca
 S  G  S  T  S  T  V  G  Y  P  A  K  Y  P  S  T  I  A  V  G  A  V  N  S  S  N  Q
        810        820        830        840        850        860        870        880
aagagcttcattctccagcgcaggttctgagcttgatgtgatggctcctggcgtgtccatccaaagcacacttcctggag
 R  A  S  F  S  S  A  G  S  E  L  D  V  M  A  P  G  V  S  I  Q  S  T  L  P  G
        890        900        910        920        930        940        950        960
gcacttacggcgcttataacggaacgtccatggcgactcctcacgttgccggagcagcagcgttaattctttctaagcac
 G  T  Y  G  A  Y  N  G  T  S  M  A  T  P  H  V  A  G  A  A  A  L  I  L  S  K  H
        970        980        990       1000       1010       1020       1030       1040
ccgacttggacaaacgcgcaagtccgtgatcgtttagaaagcactgcaacatatcttggaaactctttctactatggaaa
 P  T  W  T  N  A  Q  V  R  D  R  L  E  S  T  A  T  Y  L  G  N  S  F  Y  Y  G  K
       1050       1060       1070
agggttaatcaacgtacaagcagctgcacaataa (SEQ ID NO: 14)
 G  L  I  N  V  Q  A  A  A  Q  *  (SEQ ID NO: 15)
```

FIG. 16A

Subtilisin Amino Acid Alignment

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| | ALA | GLN | SER | VAL | PRO | TRP | GLY | ILE | SER | ARG | VAL | GLN | ALA | PRO | ALA | ALA | HIS | ASN |
| | ALA | GLN | SER | VAL | PRO | TYR | GLY | ILE | SER | GLN | ILE | LYS | ALA | PRO | ALA | LEU | HIS | SER |
| | ALA | LYS | CYS | VAL | SER | TYR | GLY | VAL | SER | GLN | ILE | LYS | ALA | PRO | ALA | LEU | HIS | SER |

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| | ARG | GLY | LEU | THR | GLY | SER | GLY | VAL | LYS | VAL | ALA | VAL | LEU | ASP | THR | GLY | ILE | SER |
| | GLN | GLY | TYR | THR | GLY | SER | ASN | VAL | LYS | VAL | ALA | VAL | ILE | ASP | SER | GLY | ILE | ASP |
| | GLN | GLY | TYR | THR | GLY | SER | ASN | VAL | LYS | VAL | ALA | VAL | ILE | ASP | SER | GLY | ILE | ASP |

| | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| | THR | --- | HIS | PRO | ASP | LEU | ASN | ILE | ARG | GLY | GLY | ALA | SER | PHE | VAL | PRO | GLY | GLU |
| | SER | SER | HIS | PRO | ASP | LEU | ASN | VAL | ARG | GLY | GLY | ALA | SER | PHE | VAL | PRO | SER | GLU |
| | SER | SER | HIS | PRO | ASP | LEU | ASN | VAL | ALA | GLY | GLY | ALA | SER | PHE | VAL | PRO | SER | GLU |

| | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| | --- | --- | PRO | SER | THR | GLN | ASP | GLY | ASN | GLY | HIS | GLY | THR | HIS | VAL | ALA | GLY | THR |
| | THR | ASN | PRO | TYR | --- | GLN | ASP | GLY | SER | SER | HIS | GLY | THR | HIS | VAL | ALA | GLY | THR |
| | THR | ASN | PRO | PHE | --- | GLN | ASP | ASN | ASN | SER | HIS | GLY | THR | HIS | VAL | ALA | GLY | THR |

| | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|
| | ILE | ALA | ALA | LEU | ASN | ASN | SER | ILE | GLY | VAL | LEU | GLY | VAL | ALA | PRO | ASN | ALA | GLU |
| | ILE | ALA | ALA | LEU | ASN | ASN | SER | ILE | GLY | VAL | LEU | GLY | VAL | SER | PRO | SER | ALA | SER |
| | --- | --- | --- | --- | --- | --- | --- | --- | --- | VAL | LEU | ALA | VAL | ALA | PRO | SER | ALA | SER |

| | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|
| | LEU | TYR | ALA | VAL | LYS | VAL | LEU | GLY | ALA | SER | GLY | SER | GLY | SER | VAL | SER | SER | ILE |
| | LEU | TYR | ALA | VAL | LYS | VAL | LEU | ASP | SER | THR | GLY | SER | GLY | GLN | TYR | SER | TRP | ILE |
| | LEU | TYR | ALA | VAL | LYS | VAL | LEU | GLY | ALA | ASP | GLY | SER | GLY | GLN | TYR | SER | TRP | ILE |

| | 109 | 110 | 111 | 112 | 113 | 114 | 115 | 116 | 117 | 118 | 119 | 120 | 121 | 122 | 123 | 124 | 125 | 126 |
|---|---|---|---|---|---|---|---|---|---|---|---|---|---|---|---|---|---|---|
| | ALA | GLN | GLY | LEU | GLU | TRP | ALA | GLY | ASN | ASN | GLY | MET | HIS | VAL | ALA | ASN | LEU | SER |
| | ILE | ASN | GLY | ILE | GLU | TRP | ALA | ILE | SER | ASN | ASN | MET | ASP | VAL | ILE | ASN | MET | SER |
| | ILE | ASN | GLY | ILE | GLU | TRP | ALA | ILE | ALA | ASN | ASN | MET | ASP | VAL | ILE | ASN | MET | SER |

| | 127 | 128 | 129 | 130 | 131 | 132 | 133 | 134 | 135 | 136 | 137 | 138 | 139 | 140 | 141 | 142 | 143 | 144 |
|---|---|---|---|---|---|---|---|---|---|---|---|---|---|---|---|---|---|---|
| | LEU | GLY | SER | PRO | SER | PRO | SER | ALA | THR | LEU | GLU | GLN | ALA | VAL | ASN | SER | ALA | THR |
| | LEU | GLY | GLY | PRO | THR | GLY | SER | THR | ALA | LEU | LYS | THR | VAL | VAL | ASP | LYS | ALA | VAL |
| | LEU | GLY | GLY | PRO | SER | GLY | SER | ALA | ALA | LEU | LYS | ALA | ALA | VAL | ASP | LYS | ALA | VAL |

| | 145 | 146 | 147 | 148 | 149 | 150 | 151 | 152 | 153 | 154 | 155 | 156 | 157 | 158 | 159 | 160 | 161 | 162 | |
|---|---|---|---|---|---|---|---|---|---|---|---|---|---|---|---|---|---|---|---|
| | SER | ARG | GLY | VAL | LEU | VAL | VAL | ALA | ALA | SER | GLY | ASN | SER | GLY | --- | ALA | GLY | SER | (SEQ ID NO: 16) |
| | SER | SER | GLY | ILE | VAL | VAL | ALA | ALA | ALA | ALA | GLY | ASN | GLU | GLY | SER | SER | GLY | SER | (SEQ ID NO: 17) |
| | ALA | SER | GLY | VAL | VAL | VAL | ALA | ALA | ALA | ALA | GLY | ASN | GLU | GLY | THR | SER | GLY | SER | (SEQ ID NO: 18) |

FIG. 16B

Subtilisin Amino Acid Alignment (cont'd.)

```
163 164 165 166 167 168 169 170 171 172 173 174 175 176 177 178 179 180
ILE SER --- --- --- TYR PRO ALA ARG TYR ALA ASN ALA MET ALA VAL GLY ALA
THR SER THR VAL GLY TYR PRO ALA LYS TYR PRO SER THR ILE ALA VAL GLY ALA
SER SER THR VAL GLY TYR PRO GLY LYS TYR PRO SER VAL ILE ALA VAL GLY ALA 181 182 183 184 185 186 187 188 189 190 191 192 193 194 195 196 197 198
THR ASP GLN ASN ASN ASN ARG ALA SER PHE SER GLN TYR GLY ALA GLY LEU ASP
VAL ASN SER SER ASN GLN ARG ALA SER PHE SER SER ALA GLY SER GLU LEU ASP
VAL ASP SER SER ASN GLN ARG ALA SER PHE SER SER VAL GLY PRO GLU LEU ASP 199 200 201 202 203 204 205 206 207 208 209 210 211 212 213 214 215 216
ILE VAL ALA PRO GLY VAL ASN VAL GLN SER THR TYR PRO GLY SER THR TYR ALA
VAL MET ALA PRO GLY VAL SER ILE GLN SER THR LEU PRO GLY GLY THR TYR GLY
VAL MET ALA PRO GLY VAL SER ILE CYS SER THR LEU PRO GLY ASN LYS TYR GLY 217 218 219 220 221 222 223 224 225 226 227 228 229 230 231 232 233 234
SER LEU ASN GLY THR SER MET ALA THR PRO HIS VAL ALA GLY ALA ALA ALA LEU
ALA TYR ASN GLY THR CYS MET ALA THR PRO HIS VAL ALA GLY ALA ALA ALA LEU
ALA LYS SER GLY THR SER MET ALA SER PRO HIS VAL ALA GLY ALA ALA ALA LEU 235 236 237 238 239 240 241 242 243 244 245 246 247 248 249 250 251 252
VAL LYS GLN LYS ASN PRO SER TRP SER ASN VAL GLN ILE ARG ASN HIS LEU LYS
ILE LEU SER LYS HIS PRO THR TRP THR ASN ALA GLN VAL ARG ASP ARG LEU GLU
ILE LEU SER LYS HIS PRO ASN TRP THR ASN THR GLN VAL ARG SER SER LEU GLU 253 254 255 256 257 258 259 260 261 262 263 264 265 266 267 268 269 270
ASN THR ALA THR SER LEU GLY SER THR ASN LEU TYR GLY SER GLY LEU VAL ASN
SER THR ALA THR TYR LEU GLY ASN SER PHE TYR TYR GLY LYS GLY LEU ILE ASN
ASN THR THR THR LYS LEU GLY ASN SER PHE TYR TYR GLY LYS GLY LEU ILE ASN 271 272 273 274 275 276
ALA GLU ALA ALA THR ARG (SEQ ID NO: 16)
VAL GLN ALA ALA ALA GLN (SEQ ID NO: 17)
VAL GLN ALA ALA ALA GLN (SEQ ID NO: 18)
```

FIG. 16C

PCR Oligos for Subtilisin E

A primer-

5'-cog agc gttg cat atg tgg aag-3'
    (SEQ ID NO: 19)

B-primer-

5'-tta gga tcc tta atg atg atg atg atg atg ttg tgc agc tgc ttg tac gtt gat-3' (SEQ ID NO: 20)

---

1.- K27Y

F 5'-ggc tct aac gta TaT gta gct gtt atc-3'
    (SEQ ID NO: 21)
    R 5'-gat aac agc tac AtA tac gtt aga gcc-3'
    (SEQ ID NO: 22)

2.- K237Y

F 5'-tta att ctt tct TaC cac ccg act tgg-3'
    (SEQ ID NO: 23)
    R 5'-cca agt cgg gtg GtA aga aag aat taa c-3'
    (SEQ ID NO: 24)

3.1- D36Y

F 5'-gac agc gga att T act ctt ctc atc-3'
    (SEQ ID NO: 25)
    R 5'-gat gag aag agt A aat tcc gct gtc-3'
    (SEQ ID NO: 26)

3.2- P210Y

F 5'-caa agc aca ctt TAt gga ggc act tac-3'
    (SEQ ID NO: 27)
    R 5'-ta agt gcc tcc aTA aag tgt gct ttg-3'
    (SEQ ID NO: 28)

4.1- K170Y

F 5'-ggc tac cct gca TaT tat cct tct act a-3'
    (SEQ ID NO: 29)
    R 5'-agt aga agg ata AtA tgc agg gta gcc-3'
    (SEQ ID NO: 30)

4.2- E195Y

F 5'-agc gca ggt tct TaT ctt gat gtg atg -3'
    (SEQ ID NO: 31)
    R 5'-cat cac atc aag AtA aga acc tgc gct-3'
    (SEQ ID NO: 32)

5.1- G61Y

F 5'-cca tac cag gaa TAc agt tct cac gg-3' (SEQ ID NO: 33)
    R 5'-cc gtg aga act gTA ttc ctg gta tgg-3' (SEQ ID NO: 34)

5.2- S98Y

F 5'-aa gtg ctt gat TAT aca gga agc ggc-3' (SEQ ID NO: 35)
    R 5'-gcc gct tcc tgt ATA atc aag cac tt-3' (SEQ ID NO: 36)

6.1- H17Y

F 5'-gcg ccg gct ctt Tac tct caa ggc t-3' (SEQ ID NO: 37)
    R 5'-a gcc ttg aga gtA aag agc cgg cgc-3' (SEQ ID NO: 38)

6.2- P86Y

F 5'-ctg ggc gtt agc TAT agc gca tca tta-3'(SEQ ID NO: 39)
    R 3'-taa tga tgc gct ATA gct aac gcc cag-3'(SEQ ID NO: 40)

7.- P201Y

F 5'-gat gtg atg gct TAt ggc gtg tcc atc-3' (SEQ ID NO: 41)
    R 5'-gat gga cac gcc aTA agc cat cac atc-3'(SEQ ID NO: 42)

FIG. 16D

STABILIZED PROTEINS

This application is a continuation-in-part of PCT/US00/28595 filed Oct. 16, 2000, which claims priority of U.S. Provisional Application No. 60/159,763 filed Oct. 15, 1999, each of which is incorporated-by-reference herein in its entirety.

1. FIELD OF THE INVENTION

The present invention relates to cross-linking methods to stabilize polypeptides and polypeptide complexes for commercial uses (pharmaceutical, therapeutic, and industrial), and to polypeptides and polypeptide complexes so cross linked.

2. BACKGROUND OF THE INVENTION

2.1. Structure and Function of Polypeptides and Polypeptide Complexes

A protein molecule consists of a linear polypeptide chain of amino acids that is intricately folded in three dimensions to form, e.g., interaction surfaces, binding pockets and active sites. A specific three-dimensional fold is generally required for protein function, wherein the fold itself is specified by the linear sequence of amino acids (i.e., the primary structure of the protein). It is notable, however, that dissimilar primary structures can have nearly identical three-dimensional folds. Evolution has conserved specific folds to a greater extent than specific primary structures. The protein folding process remains an active field of study. It is known, however, that secondary structure elements such as alpha helices, beta sheets and beta turns contribute to assembly of the tertiary structure of a polypeptide. A biological protein entity made up of several polypeptides is said to have quaternary structure.

Protein folding ultimately results from the interaction of intra- and inter-molecular forces. As such, a folded protein has a finite stability that translates into a finite structural and functional "half-life" in a given solvent environment. For example, in an aqueous environment, proteins attain stability in part by clustering hydrophobic residues in the protein core and hydrophilic residues at the protein-solvent interface. Accordingly, the activity half-life for a given protein is in part a function of solvent properties. Additionally, chemical bonds such as disulfides occur in nature to fix the co-ordination of non-neighboring side chains in close proximity in a folded protein, thereby stabilizing its structure and function.

In many biological systems, proteins associate with each other to form dimers or higher order multimers (i.e. quaternary structures), and only as such carry out their specific functions. The formation of such complexes is often an important event in regulating the activity of proteins. Various mechanisms have been found to regulate protein complex formation, such as ligand binding, or post-translational modification. The functions of protein complexes can range from providing structure to the intra-cellular matrix, where, for instance, actin forms a structural lattice, to transcription factors.

Proteins consist of discrete functional domains. Domains of similar or analogous function in different proteins usually show amino acid sequence similarities and are related in evolution. "Domain shuffling" has played a major role in the evolution (as well as in the gene engineering) of proteins with highly diverse functionalities. Interaction domains, for example, can be found in proteins of many different functions; however, sequence similarities reveal their presence. Crystallographic studies have shown that related domains are even more conserved in secondary, tertiary and quaternary structure than in primary amino acid sequence, such that structural inferences can be made about a particular domain if structural data is available on one or preferably multiple related domains (see e.g., Hofmann K., Cell Mol. Life Sci. vol. 55(8–9): pp. 1113–28, 1999; Chou J. J. et al., Cell vol. 94(2): pp. 171–80, 1998).

2.2. Biocatalytic Enzymes

There are numerous conceivable commercial applications of stabilized proteins, protein complexes and protein-protein interactions. As an example of a class of proteins for which stabilization is desirable, enzymes and other proteins that have been used as biocatalysts in industrial applications are considered in this section. Valuation of the biocatalytic enzyme market is also considered.

Industrial biocatalytic processes have use in many industrial sectors, including the chemical, detergent, pharmaceutical, agricultural, food, cosmetics, textile, materials-processing, and paper industries. Within these industries, biocatalysts have many applications, ranging from product synthesis (e.g., amino acid manufacturing), use as active agents in certain products (e.g., biological washing powders), use in diagnostic testing equipment, and use as therapeutic agents. Total sales of industrial biocatalysts in 1999 were roughly $1.4 billion. This figure is expected to grow significantly over the next decade as biocatalyst applications are enabled by novel technologies such as the invention described herein.

Market sectors believed to have potential for growth and technological innovation include engineered enzymes (e.g., for providing faster throughput, cheaper production, and/or the capability to produce novel products), pollution-control systems (e.g., for bioremediation), and non-aqueous biocatalytic systems (e.g., for oil and fat bioprocessing and drug manufacture) (see Business Intelligence Center, Explorer: "BIC Explorer"; Business Opportunities in Technology Commercialization).

Historically, only a handful of fine chemical companies such as DSM, Lonza and Avecia Ltd., have embraced and invested in biocatalytic processes. More recently, however, there have been several significant corporate investments in the field of biocatalysis. One example of such an investment is Bayer's recent announcement that it will use 6–7% of fine chemical sales to develop enzyme-based processes for certain molecules.

Major customers of fine chemical companies tend to favor suppliers with a broad range of process development. This consideration suggests that those with biocatalytic expertise stand to gain a further competitive edge in the marketplace. Some firms have recognized this and are trying quickly to close the gap via acquisitions (e.g. Great Lakes's acquisition of NSC Technologies and Cambrex's purchase of Celgene). Others acknowledge that they will lose out on further business opportunities if they don't do something to access the basic skills required for biocatalysis (Joe Blanchard, Altus Biologics Inc., 1999).

Major enzyme manufacturers (e.g. Novo, Genencor, Roche, etc.) tend to focus on large-scale enzyme production for the major industrial markets (such as detergents and textiles) and not on the application of enzymes for fine chemical development (Joe Blanchard, Altus Biologics Inc., 1999).

The continued growth in interest in the commercial use of biocatalysis and the fragmentation of the biocatalyst industry will allow both large and small companies to exploit innovative biocatalysts and the products and processes that utilize them (BIC Explorer: Business Opportunities in Technology Commercialization, 1999).

Bioremediation applications may, in the future, turn into one of the most economically important applications of biocatalytic enzymes. For example, approximately 2.3 trillion gallons of municipal effluent and 4.9 billion gallons of industrial waste are passed into U.S. waters each year, and approximately 1 million gallons of hydrocarbons enter our environment per day. Hydrocarbon cleansing is a routine requirement for various commercial operations (e.g., oil tankers, marine bilges, storage, fuel and truck tanks).

Currently, there are several processes in development that utilize biocatalysts for decontamination/decomposition of both hydrocarbons and wastewater. Not only are these processes commercially the most promising systems due to efficiency and low costs, but they are also the cleanest.

Furthermore, biocatalytic desulfurization is an inexpensive and attractive technology to the crude oil production market, where low-sulfur crude oil commands a premium price over high-sulfur crude oil. There is a growing need for cost-effective sulfur management and desulfurization worldwide due to an increased level of sulfur in fossil fuels and increasingly stringent regulations requiring lower sulfur emissions. Compliance with these regulations is expected to cost the European refining industry alone more than $50 billion in capital and $10 billion annually in operating expenditures.

All catalyst manufacturing in 1997 represented a $10 billion-plus market in the U.S., a figure quoted by the American Chemical Society (see also, "Catalyst Industry Stresses Need for Partners as Key to Future Success," C&E News, Jul. 11, 1994; CatCon '96 presentations by T. Ludermann of CONDEA Chemie GmbH, Paul Lamb of Englehard Corporation, and J. Ohmer and K. Herbert of Degussa Corporation). According to Maxigen, the total industrial enzymes market (a segment of the catalyst manufacturing market) is estimated at $1.4 billion today, growing at roughly 10% annually.

2.3. Stabilization Strategies

Several protein stabilization strategies are known in the art and have been previously described, as highlighted below.

2.3.1. Stabilization of Biocatalytic Enzymes

Several approaches have been taken to enhance the stability of biocatalysts. On the protein level, the most prominent approaches include discovery of stable biocatalysts from investigation of thermophilic organisms, directed evolution, and computational- and protein engineering, as described below.

Thermophilic organisms, or 'extremophiles', are sought in extreme environments such as deep-sea vents and Yellowstone geysers. Although enzymes of commercial relevance have been identified from them, this 'discovery' approach is limited by what can be found in nature. This approach has not yielded as many commercially-relevant, thermostable biocatalysts as was initially hoped for and/or projected.

'Directed evolution' techniques are powerful approaches capable of generating stabilized enzymes, often also with altered/improved functional specificities. However, the approach is limited by the feasibility of the selection procedure.

Algorithms that calculate intra-molecular forces within proteins are being used to design and/or evolve enzymes with greater thermostability in silico. This approach is still severely hampered by the limited understanding of the intra-molecular forces and the processes involved in protein folding.

Addition of chemical modifications that can hold proteins in their correct conformation is often referred to as protein engineering. Such protein engineering approaches include derivatization (e.g. PEGylation, addition of polymeric sucrose and/or dextran, methoxypolyethylene glycol, etc.) and old methods of protein cross-linking (e.g. production of cross-linked enzyme crystals or CLEC's). Unfortunately, these approaches are often ineffectual or cause dramatic losses in activity.

Strategies for the operational stabilization of biocatalysts that have proven successful in some respects include (a) catalyst immobilization and (b) the use of organic solvents in the reaction medium (termed medium engineering). Thermal stability upon immobilization is the result of molecular rigidity and the creation of a protected microenvironment. Methods include multi-point covalent attachment and gel-entrapment. Immobilization of biocatalysts is the most used strategy as additional benefits are obtained, such as flexibility of reactor design, and facilitated product recovery without catalyst contamination. However, despite its great technological potential, few large-scale processes utilize immobilized enzymes. Severe restrictions often arise in scale-up because of additional costs, activity losses, and issues regarding diffusion.

The main purpose of medium engineering in biocatalysis was originally to utilize robust commercial hydrolytic enzymes in organic synthesis. However, enhanced thermostability in organic media has proven an additional and significant bonus. It is hypothesized that partial or almost total substitution of water is beneficial since water is involved in enzyme inactivation. Whatever the mechanism, numerous cases have recently been reported where remarkable enzyme stability has been obtained in organic media such as polyglycols and glymes. Despite this advance, medium engineering is unlikely to solve all biocatalysis stability problems.

Some of the most promising solutions to biocatalysis problems have combined evolutionary approaches with operational stabilization techniques, such as using directed evolution to generate enzymes with higher reaction rates in organic solvents. Such combined approaches may provide significant synergies which maximally improve upon and enable commercially-relevant biocatalytic processes. In principle, the invention described herein below can be applied in combination with any of the above-mentioned known stabilization approaches.

2.3.2. Stabilization of Other Proteins

Molecular biological techniques have made it possible to stabilize some proteins by, e.g., engineering fusion-proteins. Some fusion proteins have even displayed novel functionalities. To make a fusion-protein, a single nucleic acid construct is created that directs the expression of modular domains derived from at least two proteins as one protein. Due to fusion, two domains can be held in very close proximity to each other, thereby making the local concentration of each domain very high with respect to the other. In this way, a functional complex is stabilized. For example, homo- and heterodimers of the interleukin 8 family have been stabilized in this way, maintaining functionality similar to wild type (Leong S. R. et al. Protein Sci.; vol. 6(3): pp:

609–17, 1997) Another example of protein complexes stabilized in this way is the method stabilizing immunoglobulin Fv fragments, consisting of the variable domains of immunoglobulin heavy and light chains, lacking the stabilizing effect of inter-chain disulfide bonds. It is necessary to stabilize the complex by another means to maintain the affinity of the immunoglobulin complex, and expression of both polypeptides as a single chain is one of the methods used (Pluckthun and P. Pack. Immunotechnology; vol. 3(2): pp. 83–105, 1997).

However, in the design of pharmacological reagents, it is often disadvantageous to create fusion proteins that require a linker sequence to stabilize them. For example, such linkers introduce non-self epitopes which are often recognizes by the organism as foreign and elicit immune responses. This reduces the efficacy of such therapeutics and/or diagnostics because the reagents are then cleared by the immune system (see, for example, Raag R. and Whitlow M. FASEB; vol. 9: pp. 73–80, 1995). In the case of single chain Fv fragments, the linker, which is most frequently chosen to be a highly flexible structure, allows the complex to disassociate, since the affinity of the two polypeptides to each other is low. The single chain Fv fragments then aggregate, or clump, and thereby loose their functionality (Webber K. O. et al. Mol. Immunol.; vol. 32(4): pp. 249–258, 1995). More rigid linkers that lend the complex more stability, and would thereby decrease the level or speed of aggregation and loss of functionality, are associated with increased immunogenicity (Raag R. and Whitlow M. FASEB; vol. 9: pp. 73–80, 1995).

Cross-linking the domains at close contact sites would circumvent these problems, where it is possible to direct the cross-link between two proteins to such surfaces of the proteins where after the reaction the cross-link is buried. One such means is to stabilize complexes by introducing a disulfide bond between two polypeptides by introducing point mutations to cystine in both polypeptide chains. The mutations are introduced at positions that allow the formation of such bonds (see, for example, Reiter Y. et al. Nat Biotech.; vol. 14: pp. 1239–1245, 1996; Pastan et al. U.S. Pat. No. 5,747,654, issued May 5, 1998).

Disulfide bonds are, however, unstable under many physiological conditions (Klinman J. P. (ed) Methods in Enzymology; vol. 258, 1995). Physiological conditions vary widely, for instance with respect to redox potential (oxidizing vs. reducing) and acidity (high vs. low pH) of the various, physiological milieus (intracellular, extracellular, pinocytosis vesicles, gastro-intestinal lumen, etc.). Di-sulfide bonds are found in nature only in extracellular proteins, and they are known to fall apart in reducing environments, such as the intracellular milieu. But even in the extracellular milieu, many engineered di-sulfide bonds are unstable.

Several other chemical cross-link methodologies allow the formation of bonds that are stable under a broad range of physiological and non-physiological pH and redox conditions. However, in order to maintain the complex's activity and specificity, it is necessary that the cross-link is specifically directed and controlled such that, first, the overall structure of the protein is minimally disrupted, and second, that the cross-link is buried in the protein complex so as not to be immunogenic. But with most cross-link methodologies, the degree to which it is possible to direct the bond to a specific site is too limited to allow them to be used for most bio-pharmaceutical and/or diagnostic applications. Examples of such cross-link methodologies include UV-cross-linking, and treatment of protein with formamide or glutaraldehyde.

2.3.3. Fv Fragments

Immunoglobulin Fv fragments comprise another example of a class of proteins for which stabilization is desirable. Immunoglobulin Fv fragments are the smallest fragments of immunoglobulin complexes shown to bind antigen. Fv fragments consist of the variable regions of immunoglobulin heavy and light chains and have broad applicability in pharmaceutical and industrial settings.

Value of Fv Fragment Market

A recent analysis estimated that 20 to 40 percent of all bio-technological therapeutics and diagnostics currently in development are based on immunoglobulin (Pharmaceutical Research and Manufacturers of America. New Medicines in Development, Survey. 1998). Furthermore, a significant portion, and the majority of current "state of the art" Ig-based therapeutics and diagnostics in development are Fv fragment-based (Price Waterhouse: Survey of Biopharmaceutical Industry, 1998). For reviews of the utility of immunoglobulin as a pharmacological agent, see Penichet M. L. et al., Hum Antibodies; vol. 8(3): pp. 106–18, 1997; Sensel M. G. et al. Chem. Immunol.; vol. 65: pp. 129–58, 1997; Reiter Y. and Pastan I. TIBTECH; vol. 16(12): pp. 513–520, 1998; Reiter Y. et al. Nat Biotech.; vol. 14: pp. 1239–1245, 1996; Pluckthun and P. Pack. Immunotechnology; vol. 3(2): pp. 83–105, 1997; Wright A. and Morrison S. L. Trends Biotechnol.; vol. 15(1): pp. 26–32, 1997; Schwartz M. A. et al. Cancer Chemother. Biol. Response Modif.; vol. 13:pp. 156–74, 1992; Houghton A. N. and Scheinberg D. A. Semin Oncol.; vol. 13(2): pp. 165–79, 1986; and Cao Y. and Suresh M. R. Bioconjugate Chemistry; vol. 9(6): pp. 635–644, 1998.

Following the successful introduction of the first Ig-based biotech drug, ReoPro by Centocor, in 1994, six more Ig-based drugs were approved in 1997 and 1998 and six more were in phase III clinical trials as of the end of 1998. Sales of a single, clinically successful, immunoglobulin-based product can result in annual revenues on the order of several hundreds of millions of dollars (Pharmaceutical Research and Manufacturers of America. New Medicines in Development, Survey, 1998). Together, these facts give evidence of the commercial and clinical value of these types of products.

The cost of developing, producing and clinically testing such products is, however, immense and the risk of failure is often great. Because of this, any technology that can either increase the product's effectiveness, broaden its range of applications or increase its chances of succeeding in clinical trials will add enormously to the Net Present Value of a product in development (Boston Consulting Group: The Contribution of Pharmaceutical Companies: What's at stake for America, 1993).

Fv Fragment Stabilization Methods

To date, a variety of methodologies have been employed to stabilize engineered antibodies. First, introduction of additional di-sulfide bonds has been performed through molecular biological manipulation of the antibody-expressing construct (Reiter Y. and Pastan I. TIBTECH; vol. 16(12): pp. 513–520, 1998). Second, introduction of a linker has been employed that allows both fragments to be expressed as a single chain (single chain Fv fragments) (Pluckthun and P. Pack. Immunotechnology; vol. 3(2): pp. 83–105, 1997; Cao Y. and Suresh M. R. Bioconjugate Chemistry; vol. 9(6): pp. 635–644, 1998). Finally, fusion of an exogenous di- or oligomerization domain to each of the Fv fragment chains has been performed (Pluckthun and P. Pack. Immunotechnology; vol. 3(2): pp. 83–105, 1997; Cao Y. and Suresh M. R. Bioconjugate Chemistry; vol. 9(6): pp. 635–644, 1998; see also Antibody Engineering Page, IMT, University of Marburg, FRG.

However, all of these technologies have significant drawbacks. Disulfide bonds are a suitable bond in the context of Fab fragments (see FIG. 1D), and many other extra-cellular proteins, to stabilize protein complexes. Furthermore the introduction of disulfide bonds avoids the need to introduce foreign peptides, and the resultant stabilized complexes are minimally immunogenic. Nonetheless, the introduction of disulfide bonds in Fv fragments by molecular biological means results in complexes that are insufficiently stable under many commercially relevant, physiological conditions, such as the intracellular milieu and sometimes even serum. As such they have limited usefulness in the pharmaceutical context.

With single chain Fv fragments there is a trade-off between the stability of the complex and its immunogenicity in a therapeutic or in vivo diagnostic context. Linkers that result in stable conjugates that are more rigid structures, and elicit immune responses, which in turn results in decreased utility. Linkers that are not immunogenic are generally the more flexible linkers that provide insufficient stability (see above, Raag R. and Whitlow M. FASEB; vol. 9: pp. 73–80, 1995).

Fv fragments stabilized by fusion to multimerization domains are significantly immunogenic, and lack the most significant advantage of Fv fragments in the first place: reduced size and resultant increased tissue penetration.

Other currently available chemical cross-link methods, such as UV cross-linking (see above), are severely limited in the degree to which it is possible to direct the bond to a specific site. As bio-pharmaceutical and/or diagnostic applications require the maintenance of the polypeptide's function, specificity in the cross-link reaction is paramount.

2.4. The Tyrosyl-Tyrosyl Oxidative Cross-Link

Oxidative cross-link reactions between tyrosyl side-chains have been demonstrated to occur naturally. For example, cytochrome c peroxidase compound I has been demonstrated to form di-tyrosine bonds during the endogenous reduction of its active site (Spangler B. D. and Erman J. E. Biochim. Biophys. Acta; vol. 872(1–2): pp. 155–7, 1986), and di-tyrosine-linked dimers of gammaB-crystallin are reportedly associated with cataractogenesis of the eye lens. In vitro, di-tyrosine protein-protein links are readily formed photodynamically in the presence of sensitizers (Kanwar R. and Balasubramanian D. Exp. Eye Res.; vol. 68(6): pp. 773–84, 1999). Furthermore, protein cross-linking through the formation of di-tyrosine bonds can be catalysed, for example, by peroxidase (Gmeiner B. and Seelos C. FEBS Lett; vol. 255(2): pp. 395–7, 1989), or by metallo-ion complexes (Campbell et al. Bioorganic and Medicinal Chemistry, vol. 6: pp. 1301–1037, 1998; Brown K. C. et al. Biochem.; vol.34(14): pp.4733–4739, 1995), and by light-triggered oxidants (Fancy D. A. and Kodadek T. Proc. Natl. Acad. Sci., U.S.A.; vol. 96: pp. 6020–24, 1999).

As described by Campbell et al., in the presence of an appropriate catalyst and an appropriate oxidizing reagent, an oxidative cross-link reaction can occur between tyrosyl side-chains of proteins that are properly spaced. In this reaction, the hydroxyl groups of the tyrosyl side-chains react with each other, an $H_2O$ molecule is released, and the side-chains are linked by a covalent bond. This reaction is thought to proceed through a high-valent metallo-oxo complex which abstracts an electron from an accessible tyrosyl side-chain, followed by covalent coupling of the resultant tyrosyl radical with another tyrosyl side-chain that is in sufficient proximity.

This cross-link methodology was originally developed to cross-link proteins that interact in cell lysates, as a proxy to the in vivo situation, to enable the study of the functionality of proteins by identifying other proteins they interact with. The reaction only occurs with tyrosine side-chains that are in very close proximity to each other. Furthermore, the bond formed between the tyrosyl side-chains is irreversible and stable under a very wide range of physiological conditions.

None of the above-cited references disclose or suggest methods using di-tyrosyl cross-linking for formation of buried chemical cross-links for stabilizing a protein complex while maintaining the complex's activities and specificities. Accordingly, a need exists for such methods wherein the product is functional under a wide range of physiological and non-physiological conditions, and wherein the structure, function, and specificity of the cross-linked protein complex is maintained.

Citation or identification of any reference in Section 2 or any other section of this application shall not be construed as an admission that such reference is available as prior art to the present invention.

3. SUMMARY OF THE INVENTION

This invention provides a method for stabilization of a polypeptide or polypeptide complex, by the introduction of intra-polypeptide and/or inter-polypeptide di-tyrosine bonds, which simultaneously maintains the structure and function of the polypeptide or polypeptide complex. Further, this invention provides various methods for optimizing protein stabilization. Such methods include statistical analyses of the primary amino acid sequences of related proteins (two-dimensional data analysis) and statistical analyses of the three-dimensional coordinates of proteins believed to be related in three-dimensional structure (three-dimensional data analysis).

Further, this invention provides stabilized polypeptides and polypeptide complexes. To achieve stabilization, the cross-link reaction is carefully controlled such that polypeptides and polypeptide complexes maintain their original functionality. In one embodiment, the invention provides a method for the identification of amino acid residues which, when cross-linked, are least disruptive to the structure and function of the polypeptide or polypeptide complex. In another embodiment, the invention provides a method for mutagenesis of identified residues to further control the cross-link reaction. Polypeptides and polypeptide complexes so stabilized can be utilized under a wide variety of physiological and non-physiological conditions. Further, the cross-link methodology disclosed herein may preclude the need for addition of exogenous structures to engineered proteins and complexes, such as peptide linkers. In another embodiment, the invention provides a method for statistical analysis of databases of structural and/or sequence information available for polypeptides and polypeptide complexes to be stabilized. The statistical analysis identifies suitable residue pairs which are least likely to be disruptive of structure and function when cross-linked. Further, in a polypeptide chain or chains to be cross-linked, potentially undesirable reactive side-chains may be altered using site-directed mutagenesis, e.g., to introduce a maximally conservative point mutation that will not support the cross-link reaction. The cross-link reaction conditions may also be adjusted to prevent undesired cross-links. At residues identified as desirable positions for cross-linking, reactive side-chains may be introduced by site-directed mutagenesis, and the cross-link reaction is carried out using the conditions identified above.

4. BRIEF DESCRIPTION OF THE FIGURES

The present invention may be understood more fully by reference to the following detailed description, illustrative examples of specific embodiments and the appended figures.

FIG. 1 The dityrosyl cross-link and example proteins which can be stabilized according to methods of the invention. A. Schematic representation of a dityrosyl cross-link. Addition of a cross-linking catalyst and an oxidizing reagent to a protein or protein complex preparation wherein at least two tyrosine residues occur in close proximity and in proper orientation results in a dityrosyl cross-link and one water molecule. B. Schematic representation of the canonical fold of a/b hydrolases, a group of enzymes which includes lipases. The topological positions of the active site residues are indicated as solid circles. From K.-E. Jaeger et al., 1999, Ann. Rev. Microbiol. 53, 315–351. C. Schematic representation of secondary structure of *Candida antarctica* lipase B. The topological positions of the active site residues are indicated as residues S105, D187, and H224. From J. Uppenberg et al., 1994, Structure 2, 293–308. D. Schematic representation of an immunoglobulin molecule (IgG). The immunoglobulin hetero-tetramer comprises two identical light chains, and two identical heavy chains. The complex is stabilized by inter-chain disulfide bonds; the disulfide bonds are indicated by the "S-S" links in the schematic representation. Both antigen-binding domains, one at either end of the "fork", consist of a pair of heavy and light chain variable regions, and are referred to as the "Fv fragments". The antigen-binding domain is the Fv fragment, consisting of the variable region of both the heavy and light chain consist of four relatively conserved Framework Regions that provide the overall structure, and of three Complementarity Determining Regions that lend the Fv fragment its specificity for a specific antigen. The Fab fragment, which comprises both the light and heavy chain variable regions (Vl & Vh), constant region of light chain (Cl), and the first constant region of the heavy chain (Ch1), is stabilized by an inter-chain disulfide bond. In the Fv fragment none of the immunoglobulin inter-chain disulfide bonds are present, as indicated, resulting in the requirement for this protein complex to be stabilized artificially.

FIG. 2. A. Schematic representation of a tyrosyl side-chain, consisting of an alpha carbon (A) which is still part of the polypeptide back-bone, a beta carbon (B), the first atom in the side-chain not part of the back-bone, an aromatic ring, which, in turn, consists of six carbon atoms, and a hydroxyl group (OH). The angle $\beta$ in the beta carbon between the beta carbon-hydoxyl oxygen axis and the alpha carbon-beta carbon bond is indicated. B. Schematic representation of a tyrosyl-tyrosyl bond indicating in addition the angle $\beta$, the angle $\omega$, which is the angle between the dityrosyl bond and the carbon-carbon bond in the aromatic ring of the cross-linked tyrosyl side chain that is proximal to the beta-carbon of the same side chain, projected into the two plane of the two aromatic rings. Also indicated are the angle $\alpha$, the angle between all carbon residues in the plane of the aromatic rings (120°), and the degrees of rotational freedom (1) in the dityrosine bond itself, and (2), of the alpha carbon around the beta carbon-gamma carbon (most proximal carbon atom in the aromatic ring) axis. C. Three-dimensional angles formed by the alpha carbon-alpha carbon axis, the beta carbons ($\psi$ and $\phi$), and the two planes ($\chi$) described by the alpha carbon-alpha carbon axis and (1) the alpha carbon-beta carbon bond of the first chain (A1-B1), and (2) the alpha carbon-beta carbon bond of the second chain (A2-B2).

Figure 2A:
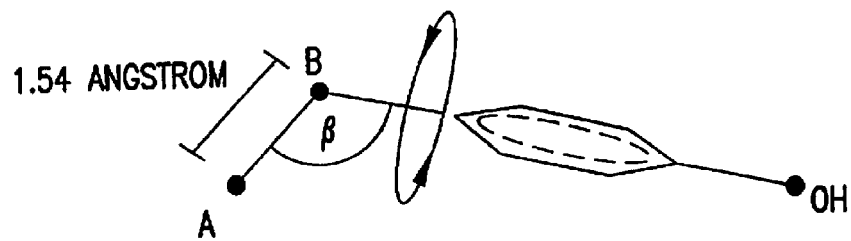
Figure 2B:
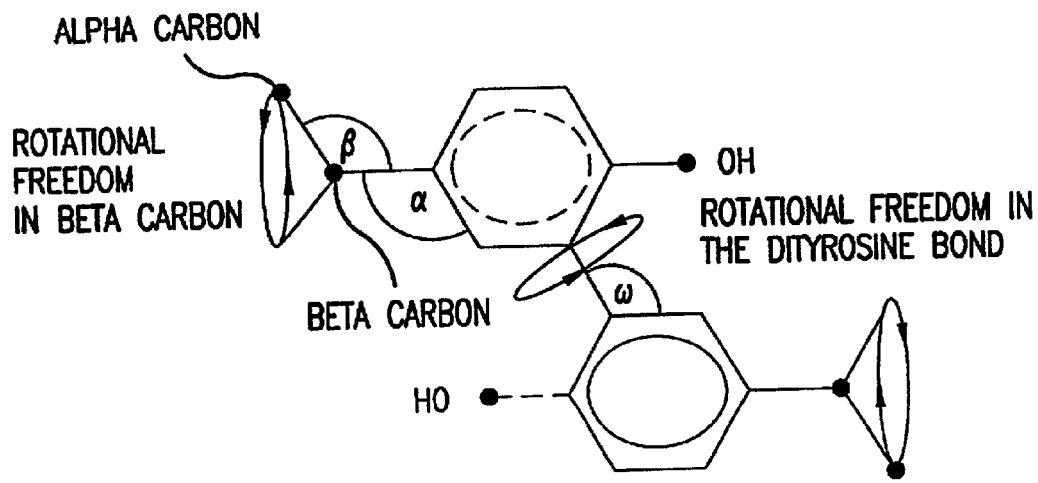
Figure 3A:
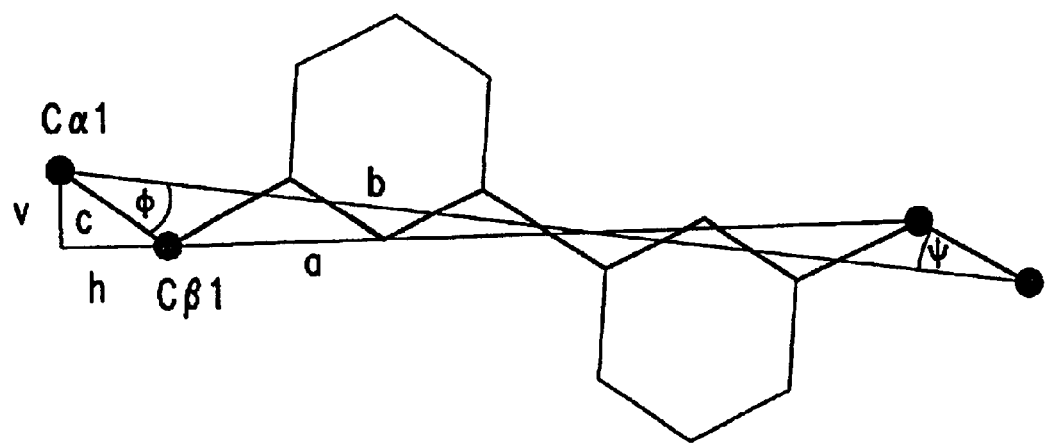
Figure 3B:
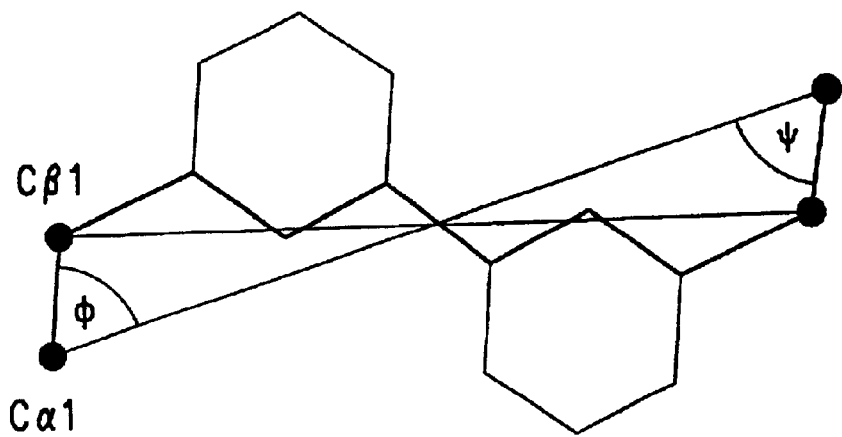

FIG. 3. The angle $\omega$, indicated in FIG. 2B, is +120°. For this configuration, the alpha carbon distances, angles $\psi$ and $\phi$, and the alpha-beta distance differences (see text) are represented geometrically for maximal and minimal configurations (that fall into one plane), given this angle $\omega$. The angle b is 109.50°, the tetrahedral angle of carbon atoms, and complete rotational freedom of the alpha carbon around the around the beta carbon-gamma carbon axis is assumed. In A, the length c is the distance between the two carbon atoms of a carbon-carbon bond; the length v is $\cos((180°-\alpha)/2) \times c$, the length h is $\sin((180°-\alpha)/2) \times c$, length a is half of the square root of the sum of 7v squared and h squared, and the length b is the square root of the sum of the square of (a+v) and h squared. In B, v is the $\cos(180°-(\beta-(180°-\alpha)/2+\arctan(h/7v)) \times c$, h is the $\sin(180°-(\beta-(180°-\alpha)/2+\arctan(h/7v)) \times c$, and, analogously, length a is half of the square root of the sum of 7v squared and h squared, and the length b is the square root of the sum of the square of (a+v) and h squared. In the configuration depicted in A, at which the alpha carbon distance is maximal, the angles $\psi$ and $\phi$ are $(180°-\alpha)/2-\arctan(h/7v)$; in the configuration in B, at which the alpha carbon distance is minimal for an angle w of +120°, $\psi$ and $\phi$ are $\beta-(180°-\alpha)/2-\arctan(h/7v)$.

Figure 4A:
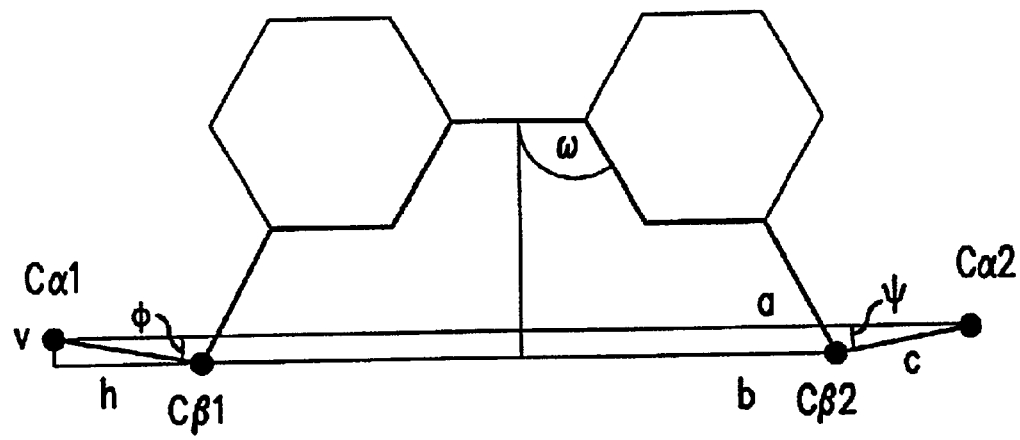
Figure 4B:
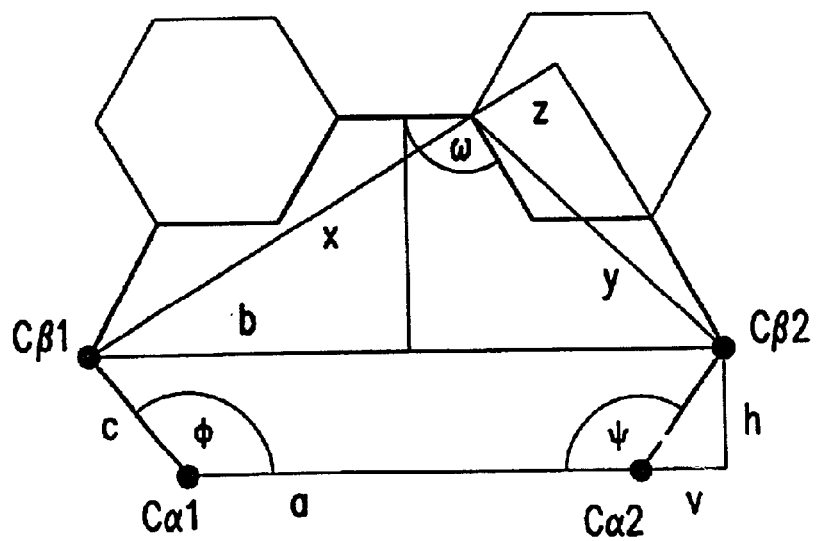

FIG. 4. The angle $\omega$, indicated in FIG. 2B, is −120°. In FIG. 4, the alpha carbon distances, angles $\psi$ and $\phi$, and the alpha-beta distance differences (see text) are represented geometrically for maximal and minimal configurations (that fall into one plane), given this angle $\omega$. The angle $\beta$ is kept constant at 109.5°, the tetrahedral angle of carbon atoms, and complete rotational freedom of the alpha carbon around the around the beta carbon-gamma carbon axis is assumed. In A, the length x is 4v, the length y is the square root of the sum of h squared and 3v squared, the length z is the $\cos(180°-120°+\arctan(h/3v)) \times y$, the length a is half of the square root of the sum of (x+z) squared and y squared, the length v is the $\cos(120°-\beta) \times c$, and the length b is the sum of the lengths a and v. In B, the length v is the $\cos((\beta-2x(180°-\alpha)/2) \times c$, and the length b is the difference of the lengths a and v. In the configuration depicted in A, at which the alpha carbon distance is maximal for an angle $\omega$ of +120°, $\psi$ and $\phi$ are $\alpha-\beta$, in the configuration in B, at which the alpha carbon distance is minimal, $\psi$ and $\phi$ are $180°-(\beta-2x((180°-\alpha)/2)$.

FIG. 5. Structural Coordinate Data, the primary (or input-) data of a 3-D database. First two amino acid residues of a representative Fv Fragment heavy (H) and light (L) chain, in Angstroms; the data of each atom is represented in rows, the atoms are listed in columns. Coordinate data is represented for all residue atoms other than Hydrogen atoms, including those involved in the polypeptide backbone and those in the amino acid's side-chain. In the left-hand column, under the heading "Chain", the identity of the polypeptide chain is listed, with which an atom's coordinates are associated. An Fv fragment consists of two polypeptides: a heavy chain (H; below) and a light chain (L; above). The number under the heading "K&W" indicates the position of the atom's residue within the Kabat & Wu (K&W) alignment system. Under the heading "Atom", the identity of an atom of the specific amino acid present in the representative polypeptide at that particular residue are indicated (identified under the heading "Amino Acid" in three letter code). The x, y, and z three-dimensional coordinates of each atom are represented in the right-hand columns, as indicated.

FIG. 6. Schematic representation of 3 actual Fv fragment entries into a 3-D database. Arrays of alpha-carbon coordinate data of heavy and light chain residues of the Fv fragments, and, as an example of relevant derivative data, calculated inter-chain, inter-atomic distances. Heavy chain alpha-carbon data is represented in rows, as described in the description of FIG. 5, and light chain alpha-carbon data is transposed, and the light chain data described in FIG. 5 is represented in columns. Derivative data describing the inter-chain, 3-D relationships of the atoms on both chains is represented at the intersection of each heavy chain row and light chain column.

FIG. 7. Statistical measurements in a 3-D database of alpha carbon distances between of Fv fragment heavy and light chain residue pairs, as an example of relevant derivative data. A. Illustrative statistical measurements of the alpha carbon distances between residue pairs of the three representative Fv Fragment heavy and light chains in the description of FIG. 6 (i.e. data shown for n=3). B. Actual statistical measurements of the alpha carbon distances between the residue pairs of all Fv fragment heavy and light chains in the sample of Fv fragments used for the selection (data shown for n=17).

FIG. 8. Schematic representation of a Fv fragment entry (Fv Fragment 1 of FIG. 6) into a 3-D database. Arrays of beta-carbon coordinate data of heavy and light chain residues of the Fv fragment, and, as an example of relevant derivative data, calculated inter-chain, inter-atomic distances. Heavy chain beta-carbon data is represented in rows, and light chain beta-carbon data is transposed and represented in columns, as described in the description of FIG. 5. Derivative data describing the inter-chain, 3-D relationships of the atoms on both chains is represented at the intersection of each heavy chain row and light chain column.

FIG. 9. Schematic Representation of the approach taken to calculate the differences between the inter-chain, inter-atomic residue pair alpha-carbon and beta-carbon distances ('alpha-beta distance differences') for an individual Fv fragment in the 3-D database (Fv Fragment 1 of FIG. 6 and 8). Heavy chain alpha-(top) and beta-carbon (middle) data is represented in rows, and light chain alpha- and beta-carbon data is transposed, and represented in columns, as described in the description of FIG. 5. Derivative data describing the inter-chain, inter-atomic distances in the top and middle panels, and the alpha-beta distance differences in the bottom panel, is represented at the intersection of each heavy chain row and light chain column.

FIG. 10 Alpha-beta distance difference data, derived as describe in FIG. 9, of representative Fv fragments (Fv fragments 1, 2, and 3 of FIG. 6) in a 3-D database. Heavy and light chain residues are represented in arrays, where the heavy chain residues are listed vertically, and the light chain residues are listed horizontally. Data correlated with heavy and light chain residues is represented at the intersection of each heavy chain row and light chain column.

FIG. 11. Statistical measurements in a 3-D database of alpha-beta distance differences of Fv fragment heavy and light chain residue pairs, as an example of relevant derivative data. A. Illustrative statistical measurements of the alpha-beta distance differences of the pairs between the three representative Fv Fragment heavy and light chains in FIG. 6 (i.e. data shown for n=3). B. Actual statistical measurements of the alpha-beta distance differences of the pairs between all Fv fragment heavy and light chains in the sample of Fv fragments used in the for selection (data shown for n=17).

FIG. 12. Quantification of amino acid side-chain physical properties, as an example of relevant derivative data, at (the first four, representative) residues of the Fv fragment heavy chain, based on Fv fragment polypeptide sequence data, compiled in a 2-D database. A. Amino Acid Sequence Data. Representation of primary data compiled in a 2-D database. Amino acids (AA) occurring at each residue are sorted by the frequency (F) of their occurrence at that specific residue. B. Amino Acid Side-chain Quantification Tables. Representation of numeric values used in a 2-D database to obtain relevant derivative data by quantifying the physical properties of amino acids: e.g. van der Waals volume $[A^3]$ (Richards, F. M.) and numeric hydrophobicity values (Eisenberg, D.). C. Quantification of the physical properties, exemplified here by van der Waals volumes, of the amino acid side-chains present at each residue in the sample of Fv fragment sequences in the 2-D database.

FIG. 13. Statistical measurements in a 2-D database of side-chain physical properties at each residue of Fv fragment heavy chains present in the 2-D database (sample), as an example of relevant derivative data, quantified as described in the description of FIG. 12. In the third column from the left, under the heading "Cons", the consensus, or most frequently occurring amino acid for each represented residue is listed. As representative statistical measures, average and standard deviations are shown, both weighted and un-weighted by the frequency of each amino acid's occurrence in the sample at each residue represented in this figure. A. Average and standard deviations are shown for residue van der Waals volumes, both weighted and un-weighted by the frequency of each amino acid's occurrence in the sample at each residue represented in this figure. B. Average and standard deviations are shown for residue Hydrophobicity quantities, both weighted and un-weighted by the frequency of each amino acid's occurrence in the sample at each residue represented in this figure.

Figure 14:
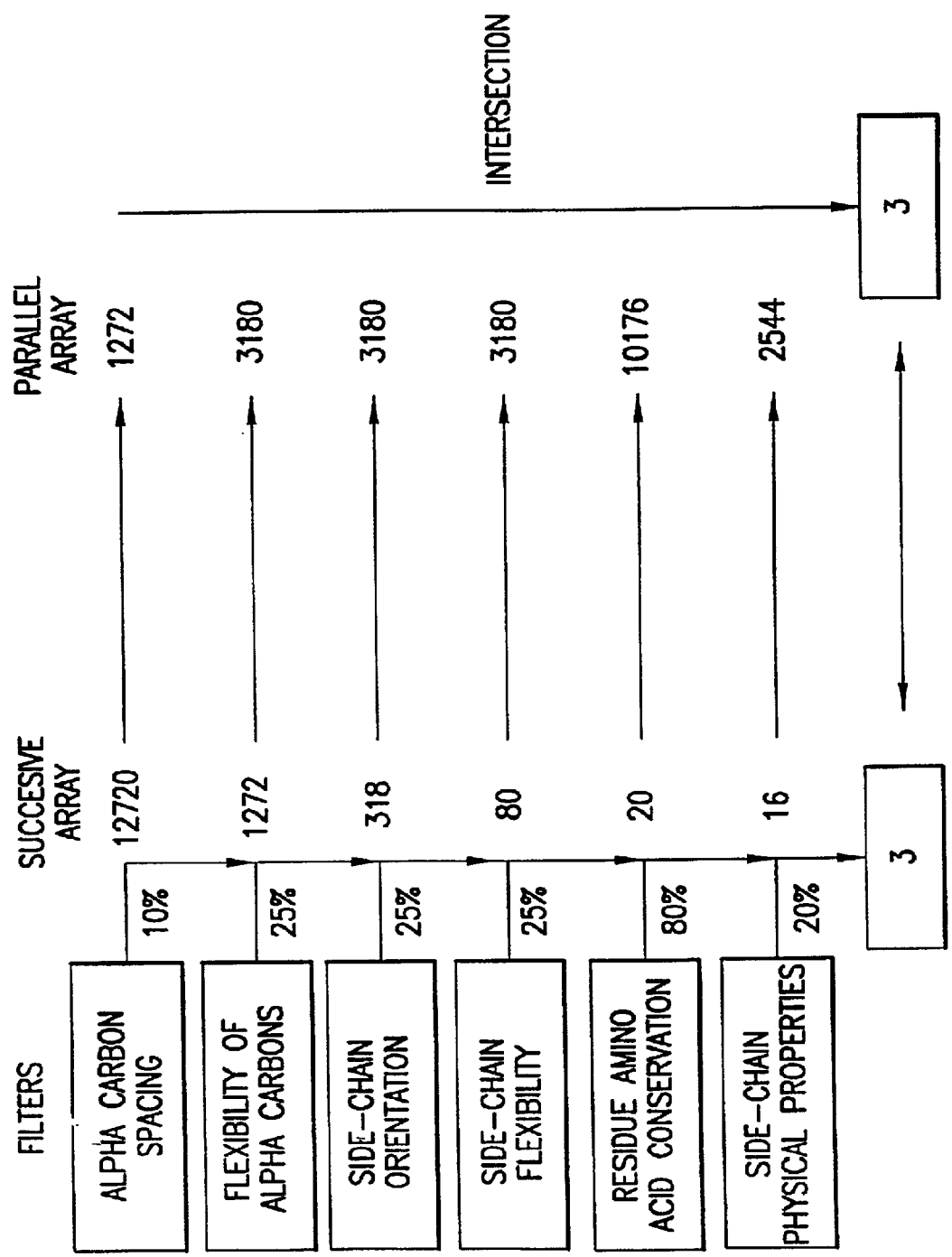

FIG. 14. Schematic illustration of a successive array and a parallel array of filters designed for automation using a computer system and software for the residue pair selection process. The filters shown are an illustrative set of filters taken from the filters described above (see Identification of Suitable Residues for the Reaction). In this illustration, the number of selected residues that "passed" each filter, either in succession (left) or in parallel (right), is derived from an analysis of the 106 amino acids of the Fv fragment light chain, the 120 amino acids of the Fv fragment heavy chain, and the resultant 12720 possible residue pairs in a given Fv fragment. The percentages indicating the permissiveness of each filter are also illustrative of the Fv fragment example. See text for further discussion (Software for Selection Process).

FIG. 15. A. Nucleotide and amino acid sequence of the *C. antayclica* Lipase B. Both sequences start where the 25 amino acid pre-propeptide is cleaved. B. Sequences of oligonucleotides used for cloning, site-directed mutagenesis, and error-prone PCR as indicated. The pPal-CALB vector is based on the pPICZalphaA vector, whereby the insert is the N-terminally His-tagged reading frame of the CALB gene, as represented in A, that is cloned into the EcoRI and NotI sites in the multiple cloning site of the vector. The vector pYal-CALB is based on the pYES2.1 V5-His-TOPO vector, whereby the insert is the alpha factor—CALB fusion, containing the N-terminal His-tag, EcoRI and NotI restriction sites, amplifed from the pPal-CALB vector. Primers for error-prone PCR allow for directional cloning of the PCR product into the EcoRI and NotI sites in the pYal-CALB vector. All of the construcis are generated by single amino acid substitutions.

FIG. 16. A. Nucleotide and amino acid sequence of Subtilisin E from *B. subtilis*. B and C. Amino acid sequence alignment of the functionally and structurally related subtilisin enzymes: the middle row represents the sequence of subtilisin E. D. Oligonucleotides used for cloning and site-directed mutagenesis of Subtilisin E, as indicated. The A Primer hybridizes with the 5' end of the gene, B-Primer hybridizes with the 3' end of the gene and further encodes a C-terminal his(6)-tag for use in affinity purification. The forward and reverse primers indicated are for the constructs 1–7 containing single and double amino acid substitutions. Constructs with double amino acid substitutions are generated by making the first amino acid substitution using the forward and reverse primers X.1, then generating the second substitution using the forward and reverse primers X.

5. DETAILED DESCRIPTION OF THE INVENTION

The invention described herein comprises methods for stabilizing polypeptides and polypeptide complexes. Also provided are polypeptides and polypeptide complexes stabilized using the described methods. The stabilization reaction is controlled such that the polypeptides and polypeptide complexes maintain their original functionality by providing specifically localized reactive side-chains. The stabilized polypeptides and polypeptide complexes can be maintained and utilized under a wide variety of physiological and non-physiological conditions without exogenous chemical structures that could be immunogenic and/or significantly decrease their efficacy.

By taking a statistical approach to analyzing databases of structural and sequence information for domains of proteins, suitable residue pairs may be identified at which the cross-link reaction is likely to be least disruptive of the overall structure.

At these residues, reactive side-chains are placed via site-directed point mutations. In the polypeptide chains that are to be cross-linked, the codons of potentially reactive side-chains at other positions are also altered to introduce a maximally conservative point mutation that will not support the reaction.

5.1. Polypeptide and Polypeptide Complexes Suitable for Application of the Invention Polypeptides and polypeptide complexes that can be stabilized by the methods described herein are single polypeptides or complexes that consist of two or more polypeptides and that remain functionally active upon application of the instant invention. Nucleic acids encoding the foregoing polypeptides are also provided. The term "functionally active" material, as used herein, refers to that material displaying one or more functional activities or functionalities associated with one or more of the polypeptides of the complex. Such activities or functionalities may be the polypeptide complexes' original, natural or wild-type activities or functionalities, or they may be designed and/or engineered. Such design and/or engineering may be achieved, for example, either by deleting amino acids, or adding amino acids to, parts of one, any, both, several, or all of the polypeptides, by fusing polypeptides of different polypeptides or polypeptide complexes, by adding or deleting post-translational modifications, by adding chemical modifications or appendixes, or by introducing any other mutations by any methods known in the art to this end as set forth in detail below.

The compositions may consist essentially of the polypeptides of a complex, and fragments, analogs, and derivatives thereof. Alternatively, the proteins and fragments and derivatives thereof may be a component of a composition that comprises other components, for example, a diluent, such as saline, a pharmaceutically acceptable carrier or excipient, a culture medium, etc.

In specific embodiments, the invention provides fragments of a stabilized polypeptide consisting of at least 3 amino acids or of a stabilized polypeptide complex consisting of at least 6 amino acids, 10 amino acids, 20 amino acids, 50 amino acids, 100 amino acids, 200 amino acids, 500 amino acids, 1000 amino acids, 2000 amino acids, or of at least 5000 amino acids.

5.1.1. Polypeptide Derivatives and Analogs

Derivatives or analogs of proteins include those molecules comprising regions that are substantially homologous to a protein or fragment thereof (e.g., in various embodiments, at least 40% or 50% or 60% or 70% or 80% or 90% or 95% identity over an amino acid or nucleic acid sequence of identical size or when compared to an aligned sequence in which the alignment is done, for example, by a computer homology program known in the art) or whose encoding nucleic acid is capable of hybridizing to a coding gene sequence, under high stringency, moderate stringency, or low stringency conditions.

Further, one or more amino acid residues within the sequence can be substituted by another amino acid of a similar polarity that acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophane and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

The derivatives and analogs of the polypeptides of the complex to be stabilized by application of the instant invention can be produced by various methods known in the art. The manipulations that result in their production can occur at the gene or protein level. For example, a cloned gene sequence can be modified by any of numerous strategies known in the art.

Chimeric polypeptides can be made comprising one or several of the polypeptides of a complex to be stabilized by the instant invention, or fragment, derivative, analog thereof (preferably consisting of at least a domain of a protein complex to be stabilized, or at least 6, and preferably at least 10 amino acids of the protein) joined at its amino- or carboxy-terminus via a peptide bond to an amino acid sequence of a different protein.

Such a chimeric polypeptide can be produced by any known method, including: recombinant expression of a nucleic acid encoding the polypeptide (comprising a polypeptide coding sequence joined in-frame to a coding sequence for a different polypeptide); ligating the appropriate nucleic acid sequences encoding the desired amino acid sequences to each other in the proper coding frame, and expressing the chimeric product; and protein synthetic techniques, for example, by use of a peptide synthesizer.

5.1.2. Manipulations of a Protein Sequence at the Protein Level

Included within the scope of the invention are polypeptides, polypeptide fragments, or other derivatives or analogs, which are differentially modified during or after translation or synthesis, for example, by glycosylation, acetylation, phosphorylation, amidation, derivatization by known protecting/blocking groups, proteolytic cleavage, etc.

Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, polypeptides, polypeptide fragments, or other derivatives or analogs that can be stabilized using the methods of the instant invention can be chemically synthesized. For example, a peptide corresponding to a portion of a protein can be synthesized by use of a peptide synthesizer. Furthermore, if desired, non-classical amino acids or chemical amino acid analogs can be introduced as substitutions and/or additions into the sequence of one, any, both, several or all of the polypeptides of the complex.

Non-classical amino acids include, but are not limited to, the D-isomers of the common amino acids, fluoro-amino acids, designer amino acids such as β-methyl amino acids, C γ-methyl amino acids, N γ-methyl amino acids, and amino acid analogs in general.

Examples of non-classical amino acids include: α-aminocaprylic acid, Acpa; (S)-2-aminoethyl-L-cysteine.HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cys-teic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-flurophenylalanine, Fphe; D-glucoseaminic acid, Gaa; homoarginine, Hag; δ-hydroxylysine.HCl, Hlys; DL-β-hydroxynorvaline, Hnvl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl)alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3-trifluroalanine, Tfa; 6-hydroxydopa, Thphe; L-vinylglycine, Vig; (−)-(2R)-2-amino-3-(2-aminoethylsulfonyl)propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (−)-(2R)-2-amino-3-(2-hydroxyethylsulfonyl)propanoic acid, Ahsopa; (−)-(2R)-2-amino-3-(2-hydroxyethylsulfanyl)propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (S)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al. (Sandberg M. et al. J. Med. Chem.; vol. 41(14): pp. 2481–91, 1998).

5.1.3. Molecular Biological Methods

Nucleic acids encoding one or more polypeptides stabilized by the methodology of instant invention are provided. The polypeptides, their derivatives, analogs, and/or chimers, of the complex can be made by expressing the DNA sequences that encode them in vitro or in vivo by any known method in the art. Nucleic acids encoding one, any, both, several, or all of the derivatives, analogs, and/or chimers of the complex to be stabilized by the methodology of the instant invention can be made by altering the nucleic acid sequence encoding the polypeptide or polypeptides by substitutions, additions (e.g., insertions) or deletions that provide for functionally acitve molecules. The sequences can be cleaved at appropriate sites with restriction endonuclease(s), followed by further enzymatic modification if desired, isolated, and ligated in vivo or in vitro. Additionally, a nucleic acid sequence can be mutated in vitro or in vivo, to create and/or destroy translation, initiation, and/or termination sequences, or to create variations in coding regions and/or to form new, or destroy preexisting, restriction endonuclease sites to facilitate further in vitro modification.

Due to the degeneracy of nucleotide coding sequences, many different nucleic acid sequences which encode substantially the same amino acid sequence as one, any, both, several, or all of the polypeptides of complex to be stabilized may be used in the practice of the present invention. These can include nucleotide sequences comprising all or portions of a domain which is altered by the substitution of different codons that encode the same amino acid, or a functionally equivalent amino acid residue within the sequence, thus producing a "silent" (functionally or phenotypically irrelevant) change.

Any technique for mutagenesis known in the art can be used, including but not limited to, chemical mutagenesis, in vitro site-directed mutagenesis, using, for example, the QuikChange Site-Directed Mutagenesis Kit (Stratagene), etc.

5.2. Applications of the Stabilization Technology

The polypeptide and polypeptide complex stabilization methods of the invention have broad applicability. Some non-limiting examples are set forth below.

5.2.1. General

Polypeptide complexes which are held together in nature by domains that mediate protein-protein interactions may be stabilized using the methods of the invention. Further, single polypeptide chains may be stabilized using the methods of the invention to engineer intra-chain di-tyrosine cross-links. For example, hormones (e.g. insulin, erythropoietin, human growth hormone or bovine growth hormone), other growth factors (e.g. insulin-like growth factors, neurotrophic factors), and enzymes and/or biosensors and biocatalysts can be stabilized, either alone or together as a complex with a receptor or other protein binding partner (McInnes C. and Sykes B. D. Biopolymers; vol. 43(5): pp. 339–66, 1997). Examples of protein-protein interaction domains which may be stabilized using the methods of the invention include, but are not limited to, leucine-zipper domains (Alber T. Curr. Opin. Genet. Dev.; vol. 2(2): pp. 205–10, 1992), SH2 and SH3 domains (Pawson T. Princess Takamatsu Symp.; vol. 24: pp. 303–22, 1994), PTB and PDZ domains (Cowburn D.

Curr. Opin. Struct. Biol.; vol. 7(6): pp. 835–8, 1997; Bockaert J. and Pin J. P. EMBO J.; vol. 18(7): pp. 1723–9, 1999), WD40 domains (Royet J. et al. EMBO J.; vol. 17(24): pp. 7351–60, 1998), death- and death effector domains (Strasser A. and Newton K. Int. J. Biochem. Cell. Biol.; vol. 31(5): pp. 533–7, 1999), disintegrin domains (Black R. A. and White J. M. Curr Opin Cell Biol.; vol. 10(5): pp. 654–9, 1998), and CARD domains (Chou J. J. et al. Cell; vol. 94(2): pp. 171–80, 1998).

Proteins which dimerize or multimerize to function may be stabilized using the methods of the invention. Such proteins include most immunoglobulin complexes, including the fragments that retain immunoglobulin functionality, such as, for example, Fab, $F(ab)_2$, Fc, and Fv fragments (Penuche M. L. et al. Hum Antibodies; vol. 8(3): pp. 106–18, 1997; Sensel M. G. et al. Chem. Immunol.; vol. 65: pp. 129–58, 1997). Most cell-surface receptors that transmit extracellular signals to intracellular signaling systems dimerize and contain some of the above mentioned domains that mediate protein-protein interactions (McInnes C. and Sykes B. D. Biopolymers; vol. 43(5): pp. 339–66, 1997; Guogiang J. et al.; Nature; vol. 401: pp.606–610, 1999). Further examples are intracellular protein complexes, such as, for example, the caspases (Chou J. J. et al. Cell; vol. 94(2): pp. 171–80, 1998).

Growth factors which may be stabilized using the methods of the invention include, but are not limited to, those that dimerize to function, such as interleukin-8 (Leong S. R. et al. Protein Sci.; vol. 6(3): pp: 609–17, 1997) and members of the NGF/TGF family. These proteins are generally characterized as having 110–120 amino acid residues, up to 50% homology with each other, and are used for the treatment of a variety of health disorders, such as cancer, osteoporosis, spinal cord injury and neuronal regeneration. Examples of the NGF family include, but are not limited to, NGF, BDNF, NT-3, NT-4/5, and NT-6, TRAIL, OPG, and FasL polypeptides (Lotz M. et al. J. Leukoc. Biol.; vol. 60(1): pp. 1–7, 1996; Casaccia-Bonnefil P. et al Microsc Res Tech.; vol. 45(4–5): pp. 217–24, 1999; Natoli G. et al. Biochem. Pharmacol.; vol. 56(8): pp. 915–20, 1998). TRAIL is currently in clinical trials, and may be useful to induce apoptosis in cancer cells. OPG is also in clinical trials and may be useful to strengthen bone tissue and prevent bone loss during menopause (Wickelgren I. Science; vol. 285(5430): pp. 998–1001, 1999).

Growth factors that do not dimerize to function, that may be stabilized using the methods of the invention include, but are not limited to, polypeptides that can be stabilized by introducing intra-chain di-tyrosine bonds, such as, as examples, insulin, erythropoietin, any of the colony stimulating factors (CSF's), PDGF.

Industrial biocatalytic processes are used in many industry sectors, including the chemical, detergent, pharmaceutical, agricultural, food, cosmetics, textile, materials-processing, and paper industries. Within these industries, biocatalysts have many applications, ranging from product synthesis (e.g. amino acid manufacturing, and fine chemical synthesis of small-molecule pharmaceuticals) through use as active agents in products (for example, in biological washing powders) to use in diagnostic testing equipment. Biocatalysts also have industrial applications that range from wastewater and agricultural soil treatment, to crude oil refinement.

Enzymes that may be stabilized using the methods of the invention include, but are not limited to, enzymes with applications as catalysts in basic, applied, or industrial research, or industry sectors, that include, for example, but are not limited to, the chemical, detergent, pharmaceutical, agricultural, food, cosmetics, textile, materials-processing, and paper industries. Within such industry sectors, enzymes, or biocatalysts, may be applied in any way, or have any kind of utility, such as, but not limited to, product synthesis, use as active agents in products, use in diagnostic testing equipment, or any other applications that may include, but are not limited to, wastewater and agricultural soil treatment, and crude oil refinement. Examples of synthetic applications include, but are not limited to, amino acid manufacturing and fine chemical synthesis. Examples of biocatalytic applications as active agents in products include, but are not limited to, such applications as biological washing powders.

Biocatalysts may be derived from enzymes of any class, family, or any other categorization of enzymes, including, but not limited to, oxidoreductases, transferases, hydrolases, lyases, isomerases, ligases, polymerases, lipases, esterases, proteases, glycosidases, glycosyl transferases, phosphatases, kinases, monooxygenases, dioxygenases, transaminases, amidases, and acylases; they may comprise a single polypeptide chain, or two or more polypeptide chains of a polypeptide complex.

A biosensor is defined as a device that consists of a biological recognition system, often called a bioreceptor, and a transducer. The interaction of the analyte with the bioreceptor is designed to produce an effect measured by the transducer, which converts the information into a measurable effect, such as an electrical signal. A biochip consists of an array of individual biosensors that can be individually monitored and generally are used for the analysis of multiple analytes. A bioreceptor can be a biological molecular species (e.g., an antibody, an enzyme, or a protein) that utilizes a biochemical mechanism for recognition. Common forms of bioreceptors used in biosensing are based on antibody/antigen and enzymatic interactions. Biosensors are widely applied in biological monitoring and environmental sensing. Furthermore, significant advances are being made in their use in the analysis of samples of biomedical interest. (Vo-Dinh and Cullum. Fresenius J Anal Chem., vol. 366: pp. 540 551, 2000). As described above, enzymes and immunoglobulin-derived polypeptides and polypeptide complexes can be stabilized by application of the instant invention. The improvements that stabilization of these molecules provides, as described above, is also of significant relevance to their use in biosensors and biochips.

The technology described herein can be applied alone, or in combination with other technologies. In one embodiment, the technology can be applied in combination with one or more alternative technologies that provide additional stability for the protein or protein complex. In another embodiment, the technology described herein can be applied in combination with one or more alternative technologies that provide additional beneficial attributes to the protein or protein complex. In yet another embodiment, the technology may be applied in combination with a single alternative technology that both stabilizes and provides additional beneficial attributes. In yet another embodiment, the technology may be applied in combination with two or more technologies, at least one of which that provides additional stability, and at least one of which that provides at least one additional attribute.

Combinations of technologies often leads to synergistic effects, i.e. the combination of technologies is more effective than the sum of the effects of the individual technologies applied individually. Synergies may be observed with regard specifically to stabilization, as example, but not limited to, by combining application of the instant invention with an in vitro evolutionary approach or immobilization strategies (see below).

Alternative technologies that provide additional stability when applied in combination with the instant technology include, but are not limited to, generating fusion proteins, such as, for example, single chain Fv fragments (scFv's; see Pluckthun and Pack, Immunotechnology; vol. 3(2): pp. 83–105, 1997); protein derivatization, such as, for example, PEGylation (Wright and Morrison. Trends Biotechnol.; vol. 15(1): pp. 26–32, 1997; DeSantis & Jones. Curr. Opin. Biotech., vol. 10(4) pp. 324–330, 1999); disulfide cross-linking, generating such products as disulfide stabilized biocatalysts (Illanes. Elec. J. Biotech., vol. 2(1): pp. 7–15, 1999) or Fv fragments (dsFv's; Reiter and Pastan. TIBTECH; vol. 16(12): pp. 513–520, 1998; Reiter et al. Nat Biotech.; vol. 14: pp. 1239–1245, 1996); other cross-link methodologies, such as, for example, generating cross-linked enzyme crystals by glutaraldehyde cross-linking (CLECs; Govardhan. Curr. Opin. Biotech., vol. 10(4) pp. 331–334, 1999; Haring and Schreier. Curr. Opin. Chem. Biol., vol. 3(1): pp.35–38, 1999; Illanes. Elec. J. Biotech., vol. 2(1): pp. 7–15, 1999); other immobilization strategies, such as, for example, embedding biocatalysts in gels, such as polyacrylamide (Illanes. Elec. J. Biotech., vol. 2(1): pp. 7–15, 1999), medium engineering, such as, for example, use of a biocatalyst in organic or aqueous-organic solvents (Carrea G. and Riva S. Angew. Chem. Int. Ed. Engl; vol. 39(13): pp. 2226–2254, 2000), and any in vitro evolution strategies, such as, for example, directed evolution by DNA shuffling (Stemmer. Nature, vol. 370: pp. 389–391, 1994; Zhao and Arnold. Nucleic Acids Res. vol. 25: pp. 1307–1308, 1997; Zhao et al. Nat. Biotechnol., vol 16: pp. 258–261, 1998; Shao et al Nucleic Acids Res. vol. 26: pp. 681–683.).

Technologies that may provide additional beneficial attributes to a polypeptide or polypeptide complex when applied in combination with the instant technology include, but are not limited to, generating fusion proteins, such as, for example, hetero specific diabodies or Fv fragments fused to cytotoxins, protein derivatization, such as, for example, PEGylation, medium engineering, such as, for example, use of a biocatalyst in an organic or aqueous-organic solvent, and any in vitro evolution strategies, such as, for example, directed evolution by DNA shuffling (see above).

Technologies can be applied simultaneously either by incorporating the process of the other technology or technologies in the process of applying the instant invention, or vice versa. This would be the case, as a non-limiting example, when applying an in vitro evolutionary approach in combination with the instant technology, such as described in Example II, Chapter 7. Alternatively, technologies can be applied in any succession that best meets the requirements and circumstances of a specific application.

5.2.2. Immunoglobulin Fv Fragments

Antibodies or immunoglobulin molecules (Ig) are among the most therapeutically useful molecules. Their utility results from their ability to bind to given target molecules with extremely high specificity and affinity. Their function in the immune system is to bind to foreign molecules (such as those present on the surface of pathogens) and to trigger the removal of these foreign molecules from the body using a variety of effector mechanisms.

With the advent of hybridoma technology, based on the work of G. Kohler and C. Milstein in the early 1980s, it has become possible to engineer pure clones of cells expressing a single antibody. The utility of such monoclonal antibodies (MAbs), whose unique binding specificity can be characterized in detail, is vast. From a monoclonal population of antibody-producing cells it is possible to isolate the genes encoding the polypeptide chains that make up the antibody. Efficient large-scale production of recombinant immunoglobulin in yeast or bacterial expression systems is an active interest of the biotechnology industry. More importantly, however, molecular biological techniques allow us to manipulate these genes and thereby produce antibody-derived proteins custom-tailored to individual applications, such as those described below.

One of the major limitations to the clinical effectiveness of antibodies is their size. Full-length immunoglobulin molecules are effective as humoral agents, but their size makes it difficult for them to penetrate tissues such as solid tumors. As a result, smaller, engineered versions of antibodies have been designed. Such engineered antibodies are designed to retain normal functional specificity with respect to antigen binding in a much smaller molecule, while at the same time uncoupling this binding function from the immunoglobulin molecule's other biological effector functions (e.g. complement activation or macrophage binding, FIG. 1D).

Figure 1D:
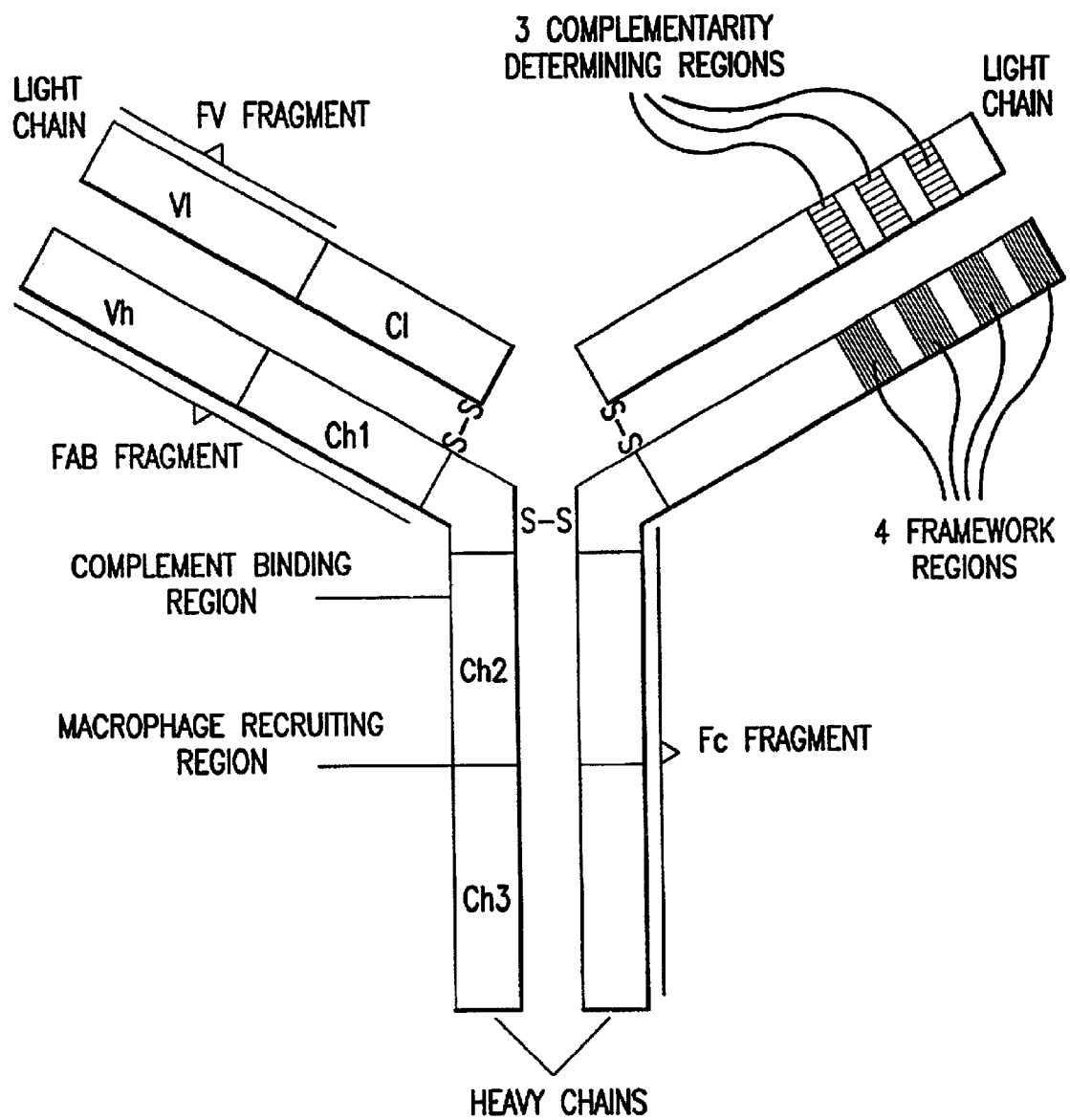

Fv fragments have been shown to be the smallest Ig-derived fragments that retain full binding specificity (FIG. 1D). The Fv fragment essentially comprises only those amino acid sequences of the antibody molecule that constitute the "variable domain" responsible for antigen binding. Due to their minimal size, Fv fragments show significantly better tissue penetration and can therefore be used in a broader range of contexts (e.g. solid tumor therapy). As used herein, Fv fragments shall include the variable region of immunoglobulin molecules or the equivalent or homologous region of a T cell receptor.

Amino acid sequence comparisons of the 110–120 residue long $V_H$ and $V_L$ regions reveal that each is made up of four relatively conserved sequence segments, called the "Framework Regions" (FRs), and three highly variable sequence segments, called "Complementarity Determining Regions" (CDR I, II, & III), which largely determine the specificity of the antibody (FIG. 1D, "right arm").

The heavy and light chain Fv fragment polypeptides associate with each other largely at sites within the conserved FRs. Fv fragments, however, lack the structural stabilizing inter-chain di-sulfide bonds present in the Ig constant regions. In order to keep recombinant Fv heavy and light chains associated and achieve functional stability and affinity, the two chains of the molecule must be "stabilized" by some other means.

5.3. Biocatalysts

Biocatalysts are a preferred class of catalysts for industrial process development, due to their high specificity and process yields. Specifically, they allow for the use of less energy and less expensive feedstocks (starting materials), reduce the number of individual steps leading to a product, and reduce waste products. Their commercial use is, however, still limited by instability, curtailing key applications. This invention provides methods for stabilizing such enzymes, improving their performance as industrial catalysts, and prolonging their half-lives and shelf-lives. Application of the instant invention also enables the industrial use of novel, previously unstable, biocatalysts, and thereby also shortens industrial process innovation cycle times.

Specifically, application of the instant invention stabilizes biocatalysts, for example, by preventing the unfolding of the protein. This increases their ability to catalyze chemical reactions under adverse reaction conditions, prolongs their half- and shelf-lives, and maximizes their activity at milder, actual process temperatures.

5.4. Obtaining Polypeptides to be Stabilized

Any method known to one skilled in the art may be used to obtain a polypeptide or polypeptide complex to be stabilized according to the methods of the invention.

5.4.1. Purification of Polypeptides

A polypeptide or polypeptide complex to be stabilized using the methods of the instant invention may be obtained, for example, by any protein purification method known in the art. Such methods include, but are not limited to, chromatography (e.g. ion exchange, affinity, and/or sizing column chromatography), ammonium sulfate precipitation, centrifugation, differential solubility, or by any other standard technique for the purification of proteins. A polypeptide may be purified from any source that produces it. For example, polypeptides may be purified from sources including, prokaryotic, eukaryotic, mono-cellular, multi-cellular, animal, plant, fungus, vertebrate, mammalian, human, porcine, bovine, feline, equine, canine, avian, tissue culture cells, and any other natural, modified, engineered, or any otherwise not naturally occurring source. The degree of purity may vary, but in various embodiments, the purified protein is greater than 50%, 75%, 85%, 95%, 99%, or 99.9% of the total mg protein. Thus, a crude cell lysate would not comprise a purified protein.

Where it is necessary to introduce one or more tyrosine residues to be cross-linked into a purified polypeptide or polypeptide complex, the polypeptide(s) can be micro-sequenced to determine a partial amino acid sequence. The partial amino acid sequence can then be used together with library screening and recombinant nucleic acid methods well known in the art to isolate the clones necessary to introduce tyrosines.

5.4.2. Expression of DNA Encoding a Polypeptide

Source of DNA

Any prokaryotic or eukaryotic cell can serve as the nucleic acid source for molecular cloning. A nucleic acid sequence encoding a protein or domain to be cross-linked or stabilized may be isolated from sources including prokaryotic, eukaryotic, mono-cellular, multi-cellular, animal, plant, fungus, vertebrate, mammalian, human, porcine, bovine, feline, equine, canine, avian, etc.

The DNA may be obtained by standard procedures known in the art from cloned DNA (e.g., a DNA "library"), by chemical synthesis, by cDNA cloning, by the cloning of genomic DNA, or fragments thereof, purified from the desired cell (see e.g., Sambrook et al.; Glover (ed.). MRL Press, Ltd., Oxford, U.K.; vol. I, II, 1985). The DNA may also be obtained by reverse transcribing cellular RNA, prepared by any of the methods known in the art, such as random- or poly A-primed reverse transcription. Such DNA may be amplified using any of the methods known in the art, including PCR and 5' RACE techniques (Weis J. H. et al. Trends Genet. 8(8): pp. 263–4, 1992; Frohman M. A. PCR Methods Appl. 4(1): pp. S40–58, 1994).

Whatever the source, the gene should be molecularly cloned into a suitable vector for propagation of the gene. Additionally, the DNA may be cleaved at specific sites using various restriction enzymes, DNAse may be used in the presence of manganese, or the DNA can be physically sheared, as for example, by sonication. The linear DNA fragments can then be separated according to size by standard techniques, such as agarose and polyacrylamide gel electrophoresis and column chromatography.

Cloning

Once the DNA fragments are generated, identification of the specific DNA fragment containing the desired gene may be accomplished in a number of ways. For example, clones can be isolated by using PCR techniques that may either use two oligonucleotides specific for the desired sequence, or a single oligonucleotide specific for the desired sequence, using, for example, the 5' RACE system (Cale J. M. et al. Methods Mol. Biol.; vol.105: pp. 351–71, 1998; Frohman M. A. PCR Methods Appl.; vol. 4(1): pp. S40–58, 1994). The oligonucleotides may or may not contain degenerate nucleotide residues. Alternatively, if a portion of a gene or its specific RNA or a fragment thereof is available and can be purified and labeled, the generated DNA fragments may be screened by nucleic acid hybridization to the labeled probe (e.g. Benton and Davis. Science; vol. 196(4286): pp. 180–2, 1977). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

The presence of the desired gene may also be detected by assays based on the physical, chemical, or immunological properties of its expressed product. For example, cDNA clones, or DNA clones which hybrid-select the proper mRNAs, can be selected and expressed to produce a protein that has, for example, similar or identical electrophoretic migration, isoelectric focusing behavior, proteolytic digestion maps, hormonal or other biological activity, binding activity, or antigenic properties as known for a protein.

Using an antibody to a known protein, other proteins may be identified by binding of the labeled antibody to expressed putative proteins, for example, in an ELISA (enzyme-linked immunosorbent assay)-type procedure. Further, using a binding protein specific to a known protein, other proteins may be identified by binding to such a protein either in vitro or a suitable cell system, such as the yeast-two-hybrid system (see e.g. Clemmons D. R. Mol. Reprod. Dev.; vol. 35: pp. 368–374, 1993; Loddick S. A. et al. Proc. Natl. Acad. Sci., U.S.A.; vol. 95: pp. 1894–1898, 1998).

A gene can also be identified by mRNA selection using nucleic acid hybridization followed by in vitro translation. In this procedure, fragments are used to isolate complementary mRNAs by hybridization. Such DNA fragments may represent available, purified DNA of another species (e.g., Drosophila, mouse, human). Immunoprecipitation analysis or functional assays (e.g. aggregation ability in vitro, binding to receptor, etc.) of the in vitro translation products of the isolated products of the isolated mRNAs identifies the mRNA and, therefore, the complementary DNA fragments that contain the desired sequences.

In addition, specific mRNAs may be selected by adsorption of polysomes isolated from cells to immobilized antibodies specifically directed against protein. A radiolabeled cDNA can be synthesized using the selected mRNA (from the adsorbed polysomes) as a template. The radiolabeled mRNA or cDNA may then be used as a probe to identify the DNA fragments from among other genomic DNA fragments.

Alternatives to isolating the genomic DNA include, chemically synthesizing the gene sequence itself from a known sequence or making cDNA to the mRNA which encodes the protein. For example, RNA for cDNA cloning of the gene can be isolated from cells that express the gene.

Vectors

The identified and isolated gene can then be inserted into an appropriate cloning or expression vector. A large number of vector-host systems known in the art may be used. Possible vectors include plasmids or modified viruses, but the vector system must be compatible with the host cell used. Such vectors include bacteriophages such as lambda derivatives, or plasmids such as pBR322 or pUC plasmid derivatives or the Bluescript vector (Stratagene).

The insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Furthermore, the gene and/or the vector may be amplified using PCR techniques and oligonucleotides specific for the termini of the gene and/or the vector that contain additional nucleotides that provide the desired complementary cohesive termini. In alternative methods, the cleaved vector and a gene may be modified by homopolymeric tailing (Cale J. M. et al. Methods Mol. Biol.; vol. 105: pp. 351–71, 1998). Recombinant molecules can be introduced into host cells via transformation, transfection, infection, electroporation, etc., so that many copies of the gene sequence are generated.

Preparation of DNA

In specific embodiments, transformation of host cells with recombinant DNA molecules that incorporate an isolated gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The sequences provided by the instant invention include those nucleotide sequences encoding substantially the same amino acid sequences as found in native proteins, and those encoded amino acid sequences with functionally equivalent amino acids, as well as those encoding other derivatives or analogs, as described below for derivatives and analogs.

Structure of Genes and Proteins

The amino acid sequence of a protein can be derived by deduction from the DNA sequence, or alternatively, by direct sequencing of the protein, for example, with an automated amino acid sequencer.

A protein sequence can be further characterized by a hydrophilicity analysis (Hopp T. P. and Woods K. R. Proc. Natl. Acad. Sci., U.S.A.; vol. 78: pp. 3824, 1981). A hydrophilicity profile can be used to identify the hydrophobic and hydrophilic regions of the protein and the corresponding regions of the gene sequence which encode such regions.

Secondary, structural analysis (Chou P. Y. and Fasman G. D. Biochemistry; vol. 13(2): pp. 222–45, 1974) can also be done, to identify regions of a protein that assume specific secondary structures. Manipulation, translation, and secondary structure prediction, open reading frame prediction and plotting, as well as determination of sequence homologies, can also be accomplished using computer software programs available in the art. Other methods of structural analysis include X-ray crystallography, nuclear magnetic resonance spectroscopy and computer modeling.

5.5. Suitable Residues for a Cross-Linking Reaction

The identification and/or engineering of suitable residues for a cross-linking reaction may involve one or more of the several steps set forth below.

5.5.1. Introduction of Point Mutations to Control the Cross-Link Reaction

Engineering the overall structure and function of a stabilized polypeptide or polypeptide complex is achieved by controlling the availability of tyrosyl side-chains for the cross-linking reaction, for example, but not limited to, via mutagenesis. Functionality of a polypeptide or polypeptide complex may be compromised or altered by a tyrosine-tyrosine cross-link reaction. In this case, an undesirable hydroxyl group of a tyrosyl side-chain may be removed by mutating such residues to phenylalanine, or masked to inhibit Its participation in such a reaction. In this way, a tyrosyl residue available for the cross-linking reaction but that may lead to distortion of structure and compromise functionality and/or specificity of the polypeptide or polypeptide complex is removed. Moreover, point mutations to tyrosine may be introduced at positions where the tyrosyl side-chains will react with each other to form a bond that causes the least distortion to structure arid function; these positions are identified as described in detail below. Thereby, the overall structure and functionality of the polypeptide or polypeptide complex is maintained.

5.5.2. Removing Undesirable Reactive Side-Chains

Reactive side-chains identified in a polypeptide chain or in the polypeptide chains of a complex are identified that subjected to the conditions of the oxidative cross-link described above would result in a bond that would distort the structure of the complex. These residues are identified by comparison of the polypeptides' amino acid sequences to available structural information on such or similar complexes (see below). Such a bond can be formed either between two polypeptide chains of the complex (inter-chain bond) or between two residues of one and the same polypeptide chain (intra-chain bond). The effect of the formation of a bond is determined by both of the reactive side-chains involved in the formation of such a bond, and therefore these residues would be identified in pairs.

To neutralize this damaging effect of the cross-link reaction, masking reagents that protect aromatic side chains (Pollitt S. and Schultz P. Agnew. Chem. Int. Ed.; vol. 37(15): pp. 2104–2107, 1998) may be use, or amino acid substitutions to phenylalanine, or any other amino acid, may be introduced at least at one of the residues involved, for example, by introducing a point mutation in the cDNA of the gene directing the expression of the polypeptide.

5.5.3. Introducing Reactive Side-Chains

To achieve a stabilized polypeptide or polypeptide complex without disrupting its structure and/or function, positions within each polypeptide are identified at which a reactive side-chain would be able to form a bond with a reactive side-chain on the, or one of the, other polypeptide chain(s). Such positions are selected both with respect toward maintaining the overall structure of the same polypeptide, and with respect toward the suitability of a position in the other polypeptide involved in the bond, and the positions are therefore selected in pairs (see below for detailed description of selection process).

When at a selected residue of either, or any, polypeptide(s) the reactive tyrosyl side-chain is not already present, a point mutation may be introduced, for example, but not limited to, by using molecular biological methods to introduce such a point mutation into the cDNA of the gene directing its expression, such that a reactive side-chain is present and available for the reaction.

5.6. Structurally Conserved Domains

5.6.1. Relationship Between Structure and Function

It is the three-dimensional, or the tertiary, structure of every protein, and the quaternary structure of every protein complex that lends them the functionality that has allowed them to be maintained and developed through the evolutionary process over time. A point mutation in the gene of a polypeptide or polypeptide complex that leads to an amino acid substitution at any given residue will alter the structure of the polypeptide and/or of the overall complex to a greater or lesser extent. The extent of such an amino acid substitution's effect on the structure of the polypeptide or polypeptide complex is dependent on the structural context of the residue, and on the nature of the resultant amino acid's side-chain.

Protein domains that show extensive similarity in their amino acid sequences to domains in other proteins are referred to as "conserved domains". Within conserved domains individual residues are more conserved than others; some can be 100% conserved, and others not at all. Most conserved domains are not only similar in their amino acid sequences, but also in their three-dimensional structures, and also in their functions. In the absence of evolutionary pressures that require a residue of a domain to be conserved, it is thought that the amino acid present at a residue would vary widely due to the rate of mutation that drives evolutionary diversification. Hence, the residues within a conserved domain that are highly conserved are thought to be important contributors to the overall structure, or the architecture, of the domain. Among the residues that are less conserved are those that contribute to the specificity of the individual domain of the group.

Conserved domains, however, can also show very little sequence homology and yet have conserved structures, such as, for examples, leucine zippers (Alber T. Curr. Opin. Genet. Dev.; vol. 2(2): pp. 205–10, 1992). Since a conserved structure also yields structurally conserved residues, the distinction between the above described 'architectural' and 'specificity determining' residues can also be made in the absence of sequence conservation. For the purposes of the instant invention, a conserved domain is defined, depending on the availability of data, either by sequence homology, which can be as low as 5% identity or similarity, or by the group of domains' structure or functionally.

5.6.2. Alignment of Conserved Residues

Alignment of the two-dimensional sequences of conserved domains reveals further that between conserved residues there are frequently interspersed by chains of varying lengths, i.e. there are varying numbers of amino acid residues between conserved residues important for the overall structure of the domain. In order to be able to compare the sequences of individual domains to determine where to direct the cross-link reaction to, it is essential that the sequences are aligned in such a way that amino acids that correspond structurally to one another are compared. For residues identified from amino acid and nucleotide sequence analyses as highly conserved, this is easily accomplished.

5.7. Statistical Selection Method

Structural comparisons of proteins and protein complexes can inform toward the identification of important residues, and toward determining the suitability of a residue or group of residues for modifications that are intended not to disrupt the fold, structure, and/or function of the protein or protein complex. A method of evaluating sets of data on related to the amino acid sequence, the structure, and/or function/functionality of related polypeptides statistically for the purpose of identifying important residues, or suitable residues for modification within a protein or protein complex of interest, or a group of related proteins or protein complexes of interest, is disclosed.

Given the availability of relevant data, it is often possible to assign quantitative values for certain characteristics of an amino acid side chain present at each residue of a domain, polypeptide, or polypeptide complex. Furthermore, given the relevant data on domains, polypeptides, or polypeptide complexes, it is possible to give groups of amino acids values that describe their structural and/or functional relationship. These values can be compared between individual domains by aligning the data in such a way that the sets of values to be compared are structurally and functionally related (see above). If there is a sufficient number of individual domains, polypeptides, or polypeptide complexes, for which such data is available, it is possible to analyze these sets of data statistically.

Statistical analysis of sets of data provides information concerning the degree of structural conservation and/or variability of a residue or a group of residues in a sample, and an indication to what extent a residue or a group of residues are involved in providing the underlying architecture, or the specificity, of a domain. This information is derived from statistical measurements that include, but are not limited to, a given value's average, variance, standard deviation, range, maximum, and minimum. For example, high variance or standard deviation measurements of a certain value implies high variability of a certain value of a residue or a group of residues, and thus a low degree of conservation, and vice versa.

From the measurements that are made on a set of data, it is possible to make predictions for the suitability of residues, or groups of residues, in related domains, polypeptides of polypeptide complexes that are, and that are not, present in the sample. A residue that is highly conserved in a sample of related polypeptides with regard to one or more relevant sets of data has a high likelihood of having similarity in all individual polypeptides including those not present in the sample. Therefore, using statistical analyses to identify important residues and/or to determine which residues are suitable for modification, lends this methodology a higher degree of generally applicability.

Potential applications of this methodology include, but are not limited to, structure-function analyses of polypeptides or polypeptide complexes, that include, for example, but are not limited to, determining the importance of one of more side-chains of a residue or a group of residues in either the active site of an enzyme, the protein-protein interaction surface of a polypeptide or polypeptide complex, the substrate binding pocket of an enzyme, and/or the binding pocket of an inhibitor.

Furthermore, as described below, this methodology can be applied to identify residues or groups of residues that are suitable for modifications that include, but are not limited to, the substitution of one or more amino acids (for example, by point-directed mutagenesis) and/or chemical modification. Non-limiting examples of such modifications include substitutions of amino acids to cysteines toward the formation of disulfide bonds; substitution of amino acids to tyrosine and subsequent chemical treatment of the polypeptide toward the formation of dityrosine bonds, as disclosed in detail herein; one or more amino acid substitutions and/or chemical modification toward generating a binding pocket for a small molecule (substrate or inhibitor), and/or the introduction of side-chain specific tags (e.g. to characterize molecular interactions or to capture protein-protein interaction partners).

The selection of residues and/or residue pairs to which a modification can be directed to stabilize a polypeptide or polypeptide complex functionally is preferably carried out by analyzing data on several polypeptide or polypeptide complex structures of a group of conserved domains or polypeptides statistically and selecting the residue pairs based on selection criteria, such as those developed and described below.

5.8. Generation and use of Databases

5.8.1. Generating Data Relevant to the Selection Criteria

The increasing availability of data concerning the genes, proteins, and other bio-molecules of many living species, make it possible to compile a significant amount of data on several protein domains/modules for statistical analyses to make predictions, as described above. This data can be transformed into data that can be utilized for such analyses directly.

Such transformations can, for instance, be done by converting nucleotide data into amino acid sequence data, and further by converting amino acid sequence data into numeric data concerning the physical properties of the amino acids' side-chains of a given residue. Such properties, for instance, can be the charge or the degree of hydrophobicity of a residue's side-chains (see below).

Furthermore, structural data of a polypeptide or of two or several polypeptides in a complex can be transformed into numeric data that describes the structural relationship of the individual residues with the other residues of the polypeptide or those of the other polypeptide(s) in the complex. An example for such a transformation would be the calculation of the distances between the alpha carbons of a residue pair using three-dimensional coordinate data derived from crystallographic resolution of a polypeptide's or a complex' structure using Pythagorean three-dimensional geometry.

It is possible to generate many different sets of data relevant for the stabilization according to the procedure of this invention concerning many of the structural features of the residues and residues pairs of a domain or a complex. As often more qualitative judgements are required to determine the reliability of the selection inputs, it also becomes a more qualitative decision how many different sets of data should be used in the identification or selection of residues or groups of residues. The less reliable the inputs, the more useful it is to implement additional information in the selection.

5.8.2. Data Sources

Sequence Data

The most direct way of accumulating sequences is by cloning and sequencing cDNAs of proteins that contain the domains/modules of interest. Sequence data is becoming more and more available through the efforts of the genome projects. Much of the sequence data is available in databases that can be accessed through the internet, or otherwise, and furthermore there are several published sources that have accumulated sequences of specific domains/modules. One such collection of specific sequence data is the Kabat Database of Sequences of Proteins of Immunological Interest Johnson, G. et al. Weir's Handbook of Experimental Immunology I. Immunochemistry and Molecular Immunology, Fifth Edition, Ed. L. A. Herzenberg, W. M. Weir, and C. Blackwell, Blackwell Science Inc., Cambridge, Me., Chapter 6.1–6.21, 1996) that contains, among other things, sequences of immunoglobulin molecules (see Sections 6–8, Examples). Such sequence data is also available from Genbank®.

Structural Data

Three-dimensional structures, as described by atomic coordinate data, of a polypeptide or complex of two or more polypeptides can be obtained in several ways.

The first approach is to mine databases of existing structural co-ordinates for the proteins of interest. The data of solved structures is often available on databases that are easily accessed in the form of three-dimensional coordinates (x, y, and z) in Ångström ($10^{-10}$ m) units. Often this data is also accessible through the internet (e.g., on-line protein structure database of the National Brookhaven Laboratory).

The second utilizes diffraction patterns (by for example, but not limited to X-rays or electrons) of regular 2- or 3-dimensional arrays of proteins as for example used in the field of X-ray crystallography. Computational methods are used to transform such data into 3-dimensional atomic co-ordinates in real space.

The third utilizes Nuclear Magnetic Resonance (NMR) to determine inter-atomic distances of molecules in solution. Multi-dimensional NMR methods combined with computational methods have succeeded in determining the atomic co-ordinates of polypeptides of increasing size. A fourth approach consists entirely of computational modeling. Algorithms may be based on the known physio-chemical nature of amino-acids and bonds found in proteins, or on iterative approaches that are experimentally constrained, or both. An example of software is the CNS program developed by Axel Brunger and colleagues at the HHMI at Yale University (Adams P. D. et al. Acta Crystallogr. D. Biol. Crystallogr.; vol. 55 (Pt 1): pp. 181–90, 1999).

Functional Data

Functional data is not as easily used, as there is no uniform way of standardizing and compiling it, such as nucleotide or amino acid sequence data, or coordinates for structural data. It is generated in many different ways, such as genetic, biochemical, and mutational analyses, molecular biological dissection and the construction of chimerical domains. In many cases the data available is not always clearly interpretable and therefore its use becomes less clearly delineated. But when available, functional data provides valuable information concerning the specificity and functionality of a domain/module, and where possible is preferably incorporated into the selection process.

Functional data is preferably also generated after the cross-link reaction according to the present invention to ensure that the predictions made were accurate for the specific application, and that the polypeptide or polypeptide complex actually retained its functionality and specificity.

5.8.3. Construction of Databases

3-D Database

A database of structural information including the atomic coordinate data of crystallographically solved polypeptides and polypeptide complexes of a group of conserved polypeptides or domains and their ligands, and derivative, relevant data is compiled. Input data is derived from structural coordinate data files. Data relevant to the selection process in this database is derived from coordinate data by applying coordinate geometry in three dimensions. This database preferably contains, for example, in addition to the structural coordinate data, the following, relevant data together with statistical measurements (e.g. mean, median, mode, standard deviation, maximum, and minimum) on each of the following features for each residue pair, whereby the sample polypeptides or polypeptide complexes are aligned as described above.

1. Inter-chain alpha carbon to alpha carbon distances of the polypeptide pair(s) of a polypeptide or complex, in order to find residue pairs that are appropriately spaced for a tyrosyl-tyrosyl bond to be formed. These distances are calculated by, for instance, but not limited to, applying Pythagorean geometry to the 3D coordinates of the alpha carbons. For every residue pair statistical measurements are calculated, such as the average, standard deviation, range and median of corresponding alpha carbon-alpha carbon distances.

2. The three angles, $\phi$, $\psi$ and $\chi$ (FIG. 2C) in relation to which the side-chains of each residue pair are oriented toward each other relative to the inter-chain alpha carbon—alpha carbon axes, are calculated from the coordinates of the alpha and beta carbons of each pair for each polypeptide or polypeptide complex in the sample. The angles are calculated by defining two planes, each of which are defined by both alpha carbon positions and one of the beta carbons' positions. By applying analytical geometry, each of the angles in the alpha carbons (scalar products), and the angle formed by the planes (vector products) are calculated. Statistical measurements are also made from this set of data, as described for the alpha carbon spacing.

The difference between the alpha carbon distance (i.e. the backbone carbon distance) and the beta carbon distance (i.e. the distance between the first carbons in each side chain) of each residue pair can also be calculated as a proxy of the orientation of the side chains relative to each other (see below).

2-D Database

A database of DNA or amino acid sequences of polypeptides or polypeptides involved in complexes of a kind, including residue side-chain usage from sequence data and derivative, relevant data is compiled. Data relevant to the selection process in this database is derived from sequence data by applying a numeric value representing the physical properties of every occurring amino acid side chain at each residue, whereby the sample polypeptides or polypeptide complexes are aligned as described above. This database contains, for example, in addition to sequence data, the following, relevant data together with statistical measurements (e.g. mean, median, mode, standard deviation, maximum, and minimum) on each of the following features for each residue pair. The statistical measurements can be made and stored on the occurring amino acids at each residue both weighted and un-weighted by the frequency at which the specific side chain occurs at this residue.

1. Numeric data concerning the bulk/volume of residues' side chains, such as, but not limited to, chemical composition, molecular weight and van der Waals volumes (Xia X. and Li W. H.; Richards, F. M.).

2. Numeric data concerning the polarity of the residues side-chains, such as, but not limited to, charge, isoelectric point, and hydrophobicity (Xia X. and Li W. H.; Eisenberg, D.).

Examples of other amino acid side chain property measurements that can be incorporated in such a database are that can be analyzed are aromaticity, aliphaticity, hydrogenation, and hydroxythiolation (Xia X. and Li W. H.).

Database of Functional Data

Where it is possible to obtain functional data that indicates the importance of a residue/residue pair for the polypeptide's or polypeptide complex' overall structure and/or specificity, it is preferably incorporated into the selection process, as it enhances the accuracy of the statistical predictions made. Such data is preferably quantified, to whatever degree possible, with respect to individual residues and/or residue pairs of a polypeptide or complex, or with respect to sub-domains or domains that mediate protein folding or protein-protein interactions, and compiled in a suitable database.

5.8.4. Required Sample Size (N)

Often the availability of data is limiting for this approach. However, to make statistical measurements on a sample of polypeptides or polypeptide complexes in order to identify residues or select residues or groups of residues for modification, it is best to use a large sample, as it will yield more accurate predictions. But often it is very labor-intensive accumulating and/or aligning the data in such a way that measurements become meaningful (see above). Since there is always a limited range of values, and since therefore their variability is also limited, accurate predictions can also be made from smaller sets of data. A sample with more than 15 individual structures, sequences or functional units is preferable.

However, previously methods have been used to position other cross-links, such as di-sulfide bonds, by examining only the one polypeptide or complex in which the point mutations are to be made, and this has resulted in functional complexes (Pastan et al., U.S. Pat. No. 5,747,654 issued May 5, 1998). Therefore it is possible to make predictions that can be accurate on a small sample. However, in order to make predictions based on statistics that include such measurements as standard deviations, it is not meaningful to use a sample size less than three (a standard deviation on 2 points of data is not a meaningful measurement). Therefore the minimum of a sample size is three for any statistical analyses.

5.9. Selection Process 5.9.1. Selection Criteria for Amino Acid Substitutions

Structural Suitability

The object of such analyses is to determine which residues pairs will be most suited for the cross-link reaction in order to main the structure, function, and specificity of a polypeptide or polypeptide complex. Therefore, many of the criteria the residue pairs are selected for relate to the pairs' potential to accommodate two cross-linked reactive side-chains without distorting the peptide-bond backbone and altering the structure of the polypeptide or complex at positions that enable and define its function and specificity.

Measurements that can be made to attain information concerning this potential relate to the determinants of the space available for the reactive side-chains and the bond. Such measurements include the distance between the residue pairs' alpha-carbons, which are the carbon atoms that are a part of the "backbone" formed by the peptide bonds between all amino acids of the polypeptide. The selected residue pairs should have an average alpha-carbon distance dose to the distance that the alpha-carbons of the cross-linked tyrosyl side-chains would be from each other if point mutations were introduced, and the cross-link reaction were directed to that residue pair. The selected residue pairs should be so close to the distance of the alpha-carbons of cross-linked tyrosyl side-chains to ensure that the functionality of the polypeptide or polypeptide complex is maintained. The criteria for this selection are described in detail below (Selection Process: Determination of the Alpha Carbon Distance in the Tyrosyl-tyrosyl Bond, The Filters). Since the variability of a residue pair's structural characteristics is also an important criterion in the selection of suitable residue pairs for the cross-link reaction (see below), the required proximity to the optimal distance is calculated for each residue pair, dependent on the variability of its alpha-carbon distances in the sample. The calculation of this requirement is also described in detail below (Selection Process: The Filters).

Measurements can also be made to determine whether the protein will fold in such a way that the reactive side-chains will be directed toward each other. Selection criteria can be developed based on the angles of the reactive side-chains and of the cross-link, the rotational freedom of the reactive side-chains, and measurements concerned with the three-dimensional geometrical relationship between the alpha-carbons and the beta-carbons of each residue pair. The beta carbon is the first carbon atom of the amino acid side-chains not part of the backbone. Such selection criteria are described in detail below (Selection Process: Calculations of Side-chain Angles in the Tyrosyl Bond, The Filters). The smallest amino acid, glycine, does not have a beta-carbon, and therefore residue pairs of which one or both of the amino acids is a conserved glycine cannot be analyzed in this way. Since mutation of a conserved glycine would likely lead to a significant structural distortion, residue pairs of which one or both residues are a conserved glycine are eliminated. This selection criterion is also described in detail below (Selection Process: The Filters). Furthermore, the structural context of the residue pair is preferably considered to ascertain the availability of three-dimensional space for the reactive side-chains and the bond. The relevant amino acid side-chain characteristics of proximal residues therefore are preferably taken into account, to further substantiate that the reactive side-chains will be able to rotate such that the bond can be formed without distorting the polypeptide backbone. If the context is such that the reactive side-chains introduced by point mutation will not be able to rotate freely into the desired position, the bond will either not readily be formed, or distortions will occur that could potentially impair or alter the function and/or specificity of the polypeptide or polypeptide complex. Therefore, selection criteria are developed to allow more conservative point mutations to be introduced that will be less likely to cause structural distortions. Such criteria are based on the amino acids present at, and surrounding, the residues of a pair, and are quantified based on numeric values of the physical properties of those amino acid side-chains. The calculation of such requirements is described in detail below (Selection Process: The Filters).

If a suitable residue pair can be identified that is already an appropriated reactive amino acid on both chains at some frequency in the sample, this pair would be an ideal selection. However, reactive side-chains present in the polypeptides or polypeptides of the complex to be cross-linked that would cause structural distortions by forming either inter- or intra-chain bonds should be neutralized, either by a means of masking/protecting them (Pollitt S. and Schultz P. Agnew. Chem. Int. Ed.; vol. 37(15): pp. 2104–2107, 1998) or by introducing maximally conservative point mutations. Such reactive residue pairs are identified using the same criteria as for the positive selection of residue pairs suitable for cross-linking. However, the presence of undesirable side-chains can only be determined by analyzing the specific sequence of an individual domain, and by comparing it with the structural information used for the positive selection.

Variability

The specificity of each individual domain and its counterpart in the same protein or in another protein of a complex is generally determined by residues that are less, or not, conserved. Therefore, considering the specificity of an individual domain, a residue with high variability can be a less desirable choice to which to direct the cross-link reaction. However, considering the overall structure and architecture of a domain, the architecture of the domain can more likely accommodate a mutation at a residue that exhibits a high degree of variability. Thus, from this perspective, high variability indicates that a residue is a better candidate at which to introduce a point mutation, and place a reactive side-chain.

Depending on the reliability and accuracy of these analyses, which, in turn, depends on the reliability of the inputs into the analyses (see below), it is possible to vary the requirement for a position's, or a pair's variability (which indicates a certain degree of flexibility and/or robustness). Thus, if the inputs are highly accurate, and sufficient data is present in the sample, it is possible to determine that a residue pair is highly suitable for the reaction although its variability is low. However, in cases where there is insufficient data or insufficient accuracy in the inputs for the analyses to allow for low variability, a residue that is important for the specificity, but not for the overall architecture of the domain may be selected. In the absence of functional data it is very difficult to determine a residue's contribution to the specificity of the domain.

5.9.2. Determination of the Alpha Carbon Distance in the Tyrosyl-Tyrosyl Bond

As stated above, selected residue pairs should have an average alpha-carbon distance close to the distance of the alpha-carbons of cross-linked tyrosyl side-chains. The range of distances that is possible between the alpha carbons of two cross-linked tyrosines is calculated for the epsilon-epsilon bonded isoform of the cross-link by applying standard geometry, Pythagorean geometry, and trigonometry. The calculations are based on all carbon-carbon bonds dityrosine bond forming 120 degree angles due to the planar structure of the aromatic ring with the exception of the angle in the beta carbon, which forms the tetrahedral angle of 109.5 degrees (FIG. 2A).

Furthermore, these calculations take into consideration that the structure of the dityrosine has significant degrees of rotational freedom, and that therefore the distance between the alpha carbons of the two tyrosines can be quite different depending on its conformation. Specifically, the rotational freedoms in the beta carbon-gamma carbon bonds, and the rotational freedom in the bond linking the aromatic rings are considered. Other isoforms of the cross-link are, however, possible, which would enable even closer distances between the alpha-carbons of the dityrosine, which is further taken into consideration in setting the possible ranges in the selection process of the residue pairs, as described below in the "Filters".

Figure 2C:
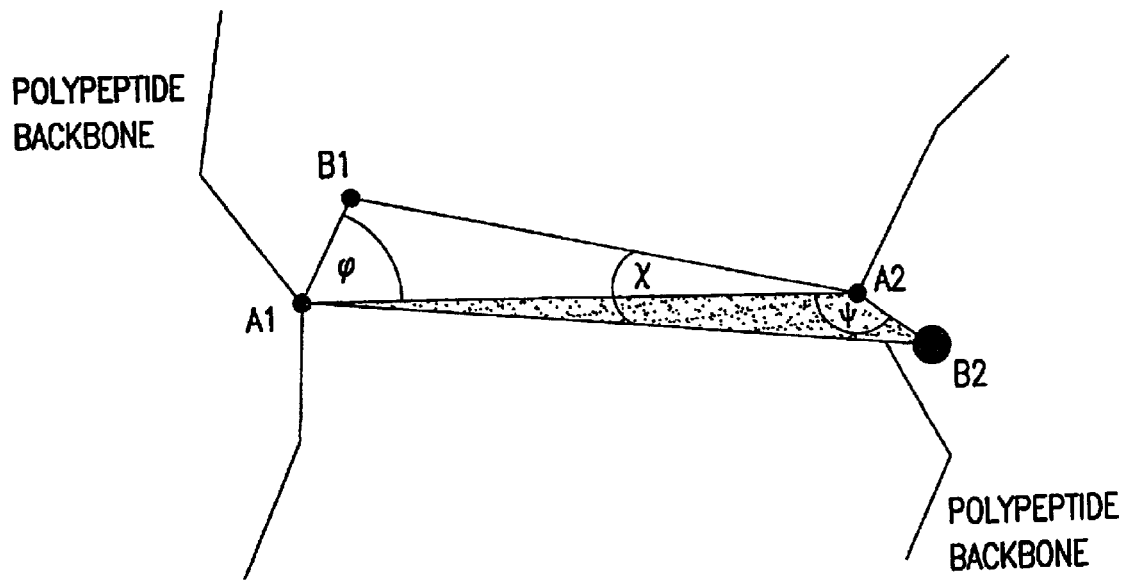

The angle $\chi$ in FIG. 2C is the angle formed by the two planes, each defined by the alpha carbon-alpha carbon axis, and individually by the positions of each of the beta carbons of the two tyrosyl side-chains involved in the bond. The angle $\omega$, determined by the rotational freedom in the dityrosine bond itself, is 120° in FIG. 3, and –120° in FIG. 4.

The schematic depictions of possible bond configurations for an angle $\omega$ of 120° in FIG. 3 represent an angle $\chi$ of 180°, at which both the maximal and minimal angles are in the projected plane. The schematic depictions of possible bond configurations for an angle ω of 120° in FIG. 4 represent an angle χ of 0°, at which both the maximal and minimal angles are in the projected plane.

For an angle ω of 120° and an angle χ of 180°, and in the configuration at which the alpha carbon distance is at a minimum (FIG. 3A), the alpha carbon distance is 1174 Å; in the configuration, in which the alpha carbon distance is at a maximum (FIG. 3B), the alpha carbon distance is 9.56 Å.

For an angle ω of −120° and an angle χ of 180°, and in the configuration at which the alpha carbon distance is at a minimum (FIG. 4A), the alpha carbon distance is 10.73 Å; in the configuration, in which the alpha carbon distance is at a maximum (FIG. 4B), the alpha carbon distance is 5.70 Å.

5.9.3. Calculations of Side-chain Angles in the Tyrosyl Bond

The angles ϕ and ψ (FIG. 2C) are the angles in each of the alpha carbon atoms between the alpha carbon-alpha carbon axis and the alpha carbon-beta carbon bond. They are calculated for the maximum and minimum distances between the alpha carbon atoms based on the rotational flexibility of the carbon-carbon bonds in the beta carbon atom.

The schematic depictions of possible bond configurations for an angle ω of 120° in FIG. 3 represent an angle χ of 180°, at which both the maximal and minimal angles are in the projected plane. The schematic depictions of possible bond configurations for an angle ω of 120° in FIG. 4 represent an angle χ of 0°, at which both the maximal and minimal angles are in the projected plane.

For an angle ω of 120° and an angle χ of 180°, and in the configuration at which the alpha carbon distance is at a minimum (FIG. 3A), the angles ϕ and ψ are maximal and equal at approximately 77.1°; in the configuration, in which the alpha carbon distance is at a maximum (FIG. 3B), the angles ϕ and ψ are minimal and equal, at approximately 34.5°.

For an angle ω of −120° and an angle χ of 0°, at which the alpha carbon distance is at a minimum (FIG. 4A), the angles ϕ and ψ are maximal and equal at 130.5°; in the configuration, in which the alpha carbon distance is at a maximum (FIG. 3B), the angles ϕ and ψ are minimal and equal, at 10.

Differences in the alpha-alpha and beta-beta distances

As a proxy to the orientation of the side-chains, the difference in the alpha-alpha and beta-beta distances ("alpha-beta distance difference") and its range are calculated again based on the extremes of alpha carbon spacing for angles ω of 120° and −120° (FIGS. 3 and 4). The maximum and minimum of the alpha-beta distance difference is calculated for both ω angles at which the both aromatic rings of the tyrosyl side-chains are in the same plane, and at which the alpha-beta distance difference is at its extremes. This difference is calculated by subtracting twice the length a from twice the length b in FIGS. 3 and 4.

For an angle ω of 120° (FIG. 3), and in the configuration, at which the alpha carbon distance is maximal, the alpha-beta distance difference is 2.37 Å, in the configuration, at which the alpha carbon distance is minimal, the alpha-beta distance difference is 0.19 Å. For an angle ω of −120° (FIG. 4), and in the configuration, at which the alpha carbon distance is maximal, the alpha-beta distance difference is 3.03 Å; in the configuration, at which the alpha carbon distance is minimal, the alpha-beta distance difference is −2.00 Å.

5.10. The Filters

In cases where sufficient data is available, the selection process preferably consists of a series of statistical tests or "filters" aimed at successively narrowing down the residue pairs most likely to result in an inter-chain cross-linked tyrosine pair of a polypeptide or polypeptide complex that minimally alters the polypeptide's or polypeptide complex' structural characteristics.

Where it is not possible or inconvenient to obtain the required data for statistical analyses, residue pairs can also be selected in any other way, including, for example, trial and error. Such selection processes yield residue pairs to which the cross-link can be directed while maintaining the functionality of the polypeptide or polypeptide complex.

An example of a successive set of filters is the following:

1. Selection based on residue pair alpha carbon spacing, based on (1) the calculated maximal and minimal distances in a cross-linked tyrosine pair (see above), and (2) the distances measured and compiled in a 3-D database. The selection is carried out on the average, median, mode, or any other statistical value suitable to determine whether the pair is likely to be spaced in such a way that the cross-link will minimally distort the overall structure. The optimal range of residue pair alpha carbon distances to be selected is determined by averaging first the minimal distances in a cross-linked tyrosine pair of the isoform depicted in FIG. 2B for ω angles of 120° and −120°, and then, analogously, averaging the maximal distances, as calculated above. These calculations result in the following optimal range:

Min: 7.63 Å, Max: 11.24 Å.

Since distances are possible in a larger range, and because other isoforms are also possible that would allow for configurations with zero distance, the average between a zero-distance and the minimal distance between alpha carbons for either angle ω provides the lower limit and the maximal distance between alpha carbons for either angle ω provides the upper limit of the preferred range. Therefore, the preferred range is:

Min: 2.85 Å, Max: 11.74 Å

Furthermore, it has been demonstrated in several cases that a protein structure can often absorb a certain amount of structural changes, and that the specificity and functionality is nonetheless maintained. It is therefore also possible, though less preferred, to introduce the reactive side-chains into residue pairs that are spaced even beyond the preferred range. Given this degree of structural flexibility the largest range possible is:

Min: 0 Å, Max: 13.74 Å.

2. Selection based on positional flexibility is carried out, as examples, on the measured/calculated standard deviations or ranges of the alpha-carbon distances in the sample, or any other statistical measure that quantifies the variability of the pairs' distances measured/calculated and compiled in a 3-D database. The range for this selection is preferably set in such a way that the average measured alpha-carbon distance of the selected residue pairs is within less than one standard deviation of the preferred range. However, 2 standard deviations are also possible as a selection criterion.

3. Selection based on side-chain orientation, determined either by calculating the three-dimensional angles relative to the alpha-carbon-alpha carbon axis (ψ, ϕ, and χ angles, as described in FIG. 2C), or by calculating a proxy, e.g. an estimate of the orientation based on the alpha-beta distance difference described above. The selection is carried out on the average, median, mode, or any other statistical value of the angles, or the proxy, suitable to determine whether the side-chains of the pair are likely to be oriented such that the cross-link will minimally distort the overall structure.

The angle $\chi$ can vary by 360°, and the bond is still possible without any distortion of the structure, so long as the angles $\psi$ and $\phi$ adjust correspondingly. Therefore, the selection range based on the angle $\chi$ should be set by a metric driven by the angles $\psi$, $\phi$, and $\chi$ with a degree of flexibility similar to that for the angles $\psi$ and $\phi$, or for the alpha-beta distance difference, the range for which is described below.

The range for the angles $\psi$, $\phi$ is, analogous to the optimal range of alpha carbon distances in Filter 1, optimally between the averages of the extreme values calculated for the isoform of the dityrosine pair depicted in FIG. 2B, and for $\omega$ angles of 120° and 120°. This optimal range is thus between:

Min: 22.49°, Max: 103.80°.

Since these angles are possible in a larger range even within this one isoform of the dityrosine bond, and since the above optimal range is often too restrictive, the minimal angle for either angle $\omega$ provides the lower limit and the maximal angle for either angle $\omega$ provides the upper limit of the preferred range. Therefore, the preferred range is:

Min: 10.5°, Max: 130.5°.

Furthermore, it has been demonstrated in several cases that a protein structure can often absorb a certain amount of structural changes, and that the specificity and functionality is nonetheless maintained. It is therefore also possible, though less preferred, to introduce the reactive side-chains into residue pairs that have angles $\psi$ and $\phi$ even beyond the preferred range. Given this degree of structural flexibility the largest range possible is:

Min: 0°, Max: 140°.

The optimal range of residue pair alpha carbon distances to be selected is determined by averaging first the minimal alpha-beta distance difference in a cross-linked tyrosine pair of the isoform depicted in FIG. 2B, and for $\omega$ angles of 120° and 120°, and then, analogously, averaging the maximal alpha-beta distance difference, as calculated above. This these calculations result in the following optimal range:

Min: 0.90 Å, Max: 2.70 Å.

Since distance differences are possible in a larger range, and since the above optimal range is often too restrictive, the minimal alpha-beta distance difference for either angle $\omega$ provides the lower limit and the maximal alpha-beta distance difference for either angle $\omega$ provides the upper limit of the preferred range. Therefore, the preferred range is:

Min: −2.00 Å, Max: 3.03 Å.

Furthermore, it has been demonstrated in several cases that a protein structure can often absorb a certain amount of structural changes, and that the specificity and functionality is nonetheless maintained. Furthermore, other isoforms of the dityrosine bond are possible. It is therefore also possible, though less preferred, to introduce the reactive side-chains into residue pairs that have alpha-beta distance difference even beyond the preferred range. Given this degree of structural flexibility the largest range possible is:

Min: −2.75 Å, Max: 3.08 Å.

4. The flexibility of the side-chains' orientation toward each other is measured on the standard deviation or range of the sample, as examples, or any other statistical measure that quantifies the variability of the side-chains of the pairs measured and compiled in a 3-D database. The range for this selection is preferably set in such a way that the average measured alpha-beta distance difference of the selected residue pairs is within less than one standard deviation of the preferred range. However, 2 standard deviations are also possible as a selection criterion.

5. Pairs that contain one or both residues that are at least 95% or more, preferably 80% or more, possibly also 50% or more conserved among the domains in the sample are eliminated, as they are likely to be important for the overall architecture of the domain, e.g. cysteines in the formation of di-sulfide bonds, leucines in the formation of leucine zippers, etc.

6. Side-chain physical properties, e.g. charge, hydrophobicity, van der Waals volumes, molecular weight, etc. The selection is carried out on the average, median, mode, or any other statistical value of these properties, individually or combined, suitable to determine whether the mutations to tyrosine and the cross-link between a residue pair will minimally distort the overall structure. The degree, to which a residue is conserved, is measured by the standard deviation or range, as examples, or any other statistical measure of the sample that quantifies the variability of the side-chains physical properties which are measured and compiled in a 2-D database.

The range can be set, as an example, in the following manner: the value of a physical property for a tyrosine pair (2×value of tyrosine) is compared with the combined value of both residues of a pair, and the difference is obtained by subtraction. The difference is then compared with the combined standard deviations of the residue pair. A multiple smaller than 2 of the combined standard deviations should make up for the difference between the value of a tyrosine pair and the combined averages of the residue pair. However, more direct or intuitive measures, as well as more sophisticated and accurate measures, can also be used to score and select for physical properties of residue pairs.

7. Elimination of pairs of which one or both residues are at a minimum 90% or more, conserved glycines, preferably 60% or more. Glycine is the smallest of the amino acids and has no beta carbon. Glycine is often associated with turns in protein structures, and substitution of a glycine with one of the largest amino acids, tyrosine, would likely have too great an impact on the overall structure.

8. The above structural and/or amino acid side-chain conservation and/or physical properties of residues/residue pairs proximal to each residue/residue pair. Proximity can be determined with regard to both the polypeptide sequences (2-D) and the overall structure of the polypeptide or polypeptide complex (3-D).

9. Functional properties concerning the effect of a residue/residue pair on the functionality and/or specificity of the polypeptide or polypeptide complex.

5.10.1. Incorporation of Data Derived from Modeling

Particularly in embodiments of the instant invention, in which a single polypeptide is stabilized, such as, for example, a peptide growth factor or a biocatalyst, any of the known methods in the art may be employed to calculate and/or compute the effects of the mutations and/or the cross-link on the structure, stability, activity, or specificity of the resultant polypeptide. One example of such a software package is the above mentioned CNS (Adams P. D. et al. Acta Crystallogr. D. Biol. Crystallogr.; vol. 55 (Pt 1): pp.

181–90, 1999) using the CHARM energy minimization plug-in. Data derived from such analyses may be used to further narrow down the selection or residue pairs, and may also be used to inform the settings of the selection parameters, such as, for example, the selection ranges.

5.10.2. Minimally Required Filters for Selection

Depending on the nature of the polypeptide or polypeptide complex, and on the availability of data, a subset of filters can, however, suffice to select a suitable pair for the cross-link reaction. For instance, a filter based on the average of residue alpha carbon spacing (Filter 1, above) can be used alone. It is also possible to make a selection using the above filters 6 and 7, both based on the degree to which residues are conserved, if structural data is available for at least one structure of such a polypeptide or polypeptide complex. Any one or more of the above filters, and any combination thereof can be used for the selection.

The order of the filters is not of importance. Furthermore, where it would add to the quality of the selection, the above filters can be split in to two or more filters to stress certain aspects of the filter. Filters can additionally be combined by designing metrics that quantify several criteria simultaneously. Thereby, for instance, the selection can be refined further by selecting one criterion taking the value of another criterion into account.

5.11. DNA Vector Constructs

The nucleotide sequence coding for the polypeptide, or for one, any, both, several or all of the polypeptides of a complex, or functionally active analogs or fragments or other derivatives thereof, can be inserted into an appropriate expansion or expression vectors, i.e., a vector which contains the necessary elements for the transcription alone, or transcription and translation, of the inserted protein-coding sequence(s). The native genes and/or their flanking sequences can also supply the necessary transcriptional and/or translational signals.

Expression of a nucleic acid sequence encoding a polypeptide or peptide fragment may be regulated by a second nucleic acid sequence so that the polypeptide is expressed in a host transformed with the recombinant DNA molecule. For example, expression of a polypeptide may be controlled by any promoter/enhancer element known in the art.

Promoters which may be used to control gene expression include, as examples, the SV40 early promoter region, the promoter contained in the 3' long terminal repeat of Rous sarcoma, the herpes thymidine kinase promoter, the regulatory sequences of the metallothionein gene; prokaryotic expression vectors such as the β-lactamnase promoter, or the lac promoter; plant expression vectors comprising the nopaline synthetase promoter or the cauliflower mosaic virus 35S RNA promoter, and the promoter of the photosynthetic enzyme ribulose biphosphate carboxylase; promoter elements from yeast or other fungi such as the Gal 4 promoter, the alcohol dehydrogenase promoter, phosphoglycerol kinase promoter, alkaline phosphatase promoter, and the following animal transcriptional control regions, which exhibit tissue specificity and have been utilized in transgenic animals: elastase I gene control region which is active in pancreatic acinar cells (Swift et al. Cell; vol. 38: pp. 639–646, 1984); a gene control region which is active in pancreatic beta cells (Hanahan D., Nature; vol. 315: pp. 115–122, 1985), an immunoglobulin gene control region which is active in lymphoid cells (Grosschedl R. et al. Cell; vol. 38: pp. 647–658, 1984), mouse mammary tumor virus control region which is active in testicular, breast, lymphoid and mast cells (Leder A. et al. Cell; vol. 45: pp. 485–495, 1986), albumin gene control region which is active in liver (Pinkert C. A. et al. Genes Dev.; vol. 1: pp. 268–276, 1987), alpha-fetoprotein gene control region which is active in liver (Krumlauf R. et al. Mol. Cell. Biol.; vol. 5: pp. 1639–1648, 1985); alpha 1-antitrypsin gene control region which is active in the liver (Kelsey G. D. et al. Genes Dev.; vol. 1: pp. 161–171, 1987), beta-globin gene control region which is active in myeloid cells (Magram J. et al. Nature; vol. 315: pp. 338–340, 1985); myelin basic protein gene control region which is active in oligodendrocyte cells in the brain (Readhead C. et al. Cell; vol. 48: pp. 703–712, 1987); myosin light chain-2 gene control region which is active in skeletal muscle (Shani M. Nature; vol. 314: pp. 283–286, 1985), and gonadotropic releasing hormone gene control region which is active in the hypothalamus (Mason A. J. et al. Science; vol. 234: pp. 1372–1378, 1986).

In a specific embodiment, a vector is used that comprises a promoter operably linked to a gene nucleic acid, one or more origins of replication, and, optionally, one or more selectable markers (e.g., an antibiotic resistance gene). In bacteria, the expression system may comprise the lac-response system for selection of bacteria that contain the vector. Expression constructs can be made, for example, by subcloning a coding sequence into one the restriction sites of each or any of the pGEX vectors (Pharmacia, Smith D. B. and Johnson K. S. Gene; vol. 67: pp. 31–40, 1988). This allows for the expression of the protein product.

Vectors containing gene inserts can be identified by three general approaches: (a) identification of specific one or several attributes of the DNA itself, such as, for example, fragment lengths yielded by restriction endonuclease treatment, direct sequencing, PCR, or nucleic acid hybridization; (b) presence or absence of "marker" gene functions; and, where the vector is an expression vector, (c) expression of inserted sequences. In the first approach, the presence of a gene inserted in a vector can be detected, for example, by sequencing, PCR or nucleic acid hybridization using probes comprising sequences that are homologous to an inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a gene in the vector. For example, if the gene is inserted within the marker gene sequence of the vector, recombinants containing the insert an identified by the absence of the marker gene function. In the third approach, recombinant expression vectors can be identified by assaying the product expressed by the recombinant expression vectors containing the inserted sequences. Such assays can be based, for example, on the physical or functional properties of the protein in in vitro assay systems, for example, binding with anti-protein antibody.

Once a particular recombinant DNA molecule is identified and isolated, several methods known in the art may be used to propagate it. Once a suitable host system and growth conditions are established, recombinant expression vectors can be propagated and prepared in quantity. Some of the expression vectors that can be used include human or animal viruses such as vaccinia virus or adenovirus; insect viruses such as baculovirus; yeast vectors; bacteriophage vectors (e.g., lambda phage), and plasmid and cosmid DNA vectors.

Once a recombinant vector that directs the expression of a desired sequence is identified, the gene product can be analyzed. This is achieved by assays based on the physical or functional properties of the product, including radioactive labeling of the product followed by analysis by gel electrophoresis, immunoassay, etc.

5.12. Systems of Gene Expression and Protein Purification

A variety of host-vector systems may be utilized to express the protein-coding sequences. These include, as examples, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a specific embodiment, the gene may be expressed in bacteria that are protease deficient, and that have low constitutive levels and high induced levels of expression where an expression vector is used that is inducible, for example, by the addition of IPTG to the medium.

In yet another specific embodiment, the polypeptide, or one, any, both, several or all of the polypeptides of a complex may be expressed with signal peptides, such as, for example, pelB bacterisl signal peptide, that directs the protein to the bacterial periplasm (Lei et al J. BacteroL, vol. 169: pp. 4379, 1987). Alternatively, protein may be allowed to form inclusion bodies, and subsequently be resolubilized and refolded (Kim S. H. et al. Mol. Immunol., vol. 34: pp. 891, 1997).

In yet another embodiment, a fragment of the polypeptide, or one, any, both, several or all of the polypeptides a complex comprising one or more domains of the protein is expressed. Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

In addition, a host cell strain may be chosen that modulates the expression of the inserted sequences, or modifies and processes the gene product in the specific fashion desired. Expression from certain promoters can be elevated in the presence of certain inducers; thus, expression of the genetically engineered polypeptides may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign polypeptide(s) expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other embodiments of the invention, the polypeptide, or one, any, both, several or all of the polypeptides a complex, and/or fragments, analogs, or derivative(s) thereof may be expressed as a fusion-, or chimeric, protein product (comprising the protein, fragment, analog, or derivative joined via a peptide bond to a heterologous protein sequence of a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, for example, by use of a peptide synthesizer.

The polypeptides of a complex may be expressed together in the same cells either on the same vector, driven by the same or independent transcriptional and/or translational signals, or on separate expression vectors, for example by cotransfection or cotransformation and selection, for example, may be based on both vectors' individual selection markers. Alternatively, one, any, both, several or all of the polypeptides a complex may be expressed separately; they may be expressed in the same expression system, or in different expression systems, and may be expressed individually or collectively as fragments, derivatives or analogs of the original polypeptide.

5.13. The Cross-Link Reaction

5.13.1. Introduction of Point Mutations to Phenylalanine

One of the codons of every tyrosine residue pair that may react with each other and cause undesirable structural and/or functional distortions is preferably point mutated to codons that direct the expression of phenlyalanine.

Point mutations can be introduced into the DNA encoding the polypeptide, or one, any, both, several or all of the polypeptides of a complex by any method known in the art, such as oligonucleotide-mediated site-directed mutagenesis. Such methods may utilize oligonucleotides that are homologous to the flanking sequences of such codons, but that encode tytosine at the selected site or sites. With these oligonucleotides, DNA fragments containing the point mutation or point mutations are amplified and inserted into the gene or genes, for example, by subcloning. One example of such methods is the application of the QuikChange™ Site-Directed Mutagenesis Kit (Stratagene Catalog #200518); this kit uses the Pfu enzyme having non-strand-displacing action in any double stranded plasmid mutation in PCR reactions. Other methods may utilize other enzymes such as DNA polymerases, or fragments and/or analogs thereof.

The plasmid or plasmids containing the point mutation or point mutations are, for example, transformed into bacteria for expansion, and the DNA is prepared as described above. The isolated, expanded, and prepared DNA may be examined to verify that it encodes the polypeptide or polypeptides of the complex, and that the correct mutation or mutations were achieved. This may, for example, be verified by direct DNA sequencing, DNA hybridization techniques, or any other method known in the art.

5.13.2. Purification of Gene Products

The gene product may be isolated and purified by standard methods including chromatography (e.g., ion exchange, affinity, and sizing column chromatography), ammonium sulfate precipitation, centrifugation, differential solubility, or by any other standard technique for the purification of proteins.

The functional properties may be evaluated using any suitable assay. The amino acid sequence of the protein can be deduced from the nucleotide sequence of the chimeric gene contained in the recombinant vector. As a result, the protein can be synthesized by standard chemical methods known in the art (e.g., see Hunkapiller M. et al. Nature; vol. 310(5973): pp. 105–11, 1984).

5.13.3. The Reaction

The cross-link reaction can utilize any chemical reaction or physical reaction known in the art that specifically introduces dityrosine cross-links, such as peroxidase catalysed cross-linking, or photodynamically in the presence or absence of sensitizers (see Section II). Preferably, however, the reaction is catalyzed by a metallo-ion complex, as described in detail below.

Partially purified polypeptides containing appropriate tyrosine residues may be equilibrated by dialysis in a buffer, such as phosphate buffered saline (PBS), together or separately before mixing them. The catalyst is then added (on ice or otherwise). The catalyst of the reaction is any compound that will result in the above cross-link reaction. The catalyst should have the structural components that convey the specificity of the reaction, generally provided by a structure complexing a metal ion, and the ability to abstract an electron from the substrate in the presence of an oxidizing reagent, generally provided by the metal ion. An active metal is encased in a stable ligand that blocks non-specific binding to chelating sites on protein surfaces. For example, either a metalloporphyrin, such as, but not limited to, 20-tetrakis (4-sulfonateophenyl)-21H,23H-porphine manganese (III) chloride (MnTPPS) or hemin iron (III) protoporphyrin IX chloride (Campbell L. A. et al. Bioorganic and Medicinal Chemistry, vol. 6: pp. 1301–1037, 1998), or a metal ion-peptide complex, such as the tripeptide NH2-Gly-Gly-His-COOH complexing Ni++ can serve as the catalyst of the reaction. Metalloporphoryns are a class of oxidative ligand-metal complexes for which there are few, if any, high affinity sites in naturally occurring eukaryotic proteins. The reaction can also be catalyzed by intramolecular Ni++ peptide complexes, such as—and C-terminal amino acids consisting either of 3 or more histidine residues (his-tag), or of the above GGH tripeptide. The reaction is initiated by the addition of the oxidizing reagent at room temperature or otherwise. Oxidizing reagents include, but are not limited to, hydrogen peroxide, oxone, and magnesium monoperxyphthalic acid hexahydrate (MMPP) (Brown K. C. et al. Biochem.; vol. 34(14): pp. 4733–4739, 1995). Higher specificity can be achieved by using a photogenerated oxidant, such as the oxidant used in the process described by Fancy D. and Thomas Kodadek, which involves brief photolysis of tris-bipyridylruthenium(II) dication with visible light in the presence of an electron acceptor, such as aminonium persulfate (Fancy D. A. and Kodadek T. Proc. Natl. Acad. Sci., U.S.A.; vol. 96: pp. 6020–24, 1999). The optimal reaction period is preferably determined for each application; however, In cases where an optimization process is not possible, the reaction should preferably be stopped after one minute. Using a photogenerated oxidant, such as above described, the exposure to light can be less than one second. The reaction is stopped by the addition of a sufficient amount of reducing agent, such as β-mercaptoethanol, to counteract and/or neutralize the oxidizing agent.

Alternatively, the reaction may be stopped by the addition of a chelating reagent, such as, for example, EDTA or EGTA. The solution is again equilibrated by dialysis in a buffer, such as phosphate buffered saline (PBS), to remove the reagents required for the cross-link reaction, such as the oxidizing reagent, the catalyst, or the metal ion, reducing agents, chelating reagents, etc. The cross-link reaction conditions are preferably adjusted such that the polypeptides or polypeptides of a complex that have been mutated to remove undesirable tyrosyl side-chains no longer form a bond. These conditions are adjusted by varying the reaction temperature, pH, or osmolarity conditions, or by varying the concentration of the polypeptides, the catalyst, the oxidizing agent, or any other reagents that are applied toward such a reaction. The catalyst is a small molecule that diffuses easily, and can be used at varying concentrations. Tightly packed polypeptide hydrophobic cores have a degree of solvent accessibility. This may be modulated by any known method in the art, including, but not limited to, by altering the reaction temperature, or by the addition of salts, detergents, deoxycholate, or guanidinium.

5.14. Achieving a Stabilized Polypeptide or Complex

5.14.1. Point Mutation to Tyrosine and Gene Product Purification

The codons of the residues identified as a suitable pair to which the cross-link should be directed, as described above, and selected for a particular embodiment of the instant invention, are point mutated such that the resultant residue pairs direct the expression of tyrosyl side-chains. Point mutations are introduced as described above.

The gene products are again purified as described above.

5.14.2. Cross-Linking the Polypeptide or Complex

The polypeptides now containing tyrosyl side-chains at the residues to which the cross-link reaction should be directed are subjected to the cross-link reaction under the conditions determined as described above and carried out, also as described above. The efficiency of the reaction may be examined, for example, by Western blotting experiments, in which a cross-linked complex should run at approximately the molecular weight of both or all polypeptides of the complex. If the bond is readily formed under the above conditions, the strength of the reaction may still be further adjusted to the minimally required strength.

In embodiments of the invention wherein the cross-link is directed to residue pairs that are buried and/or are not readily accessible to the catalyst or oxidizing reagents, secondary and higher order polypeptide structure can be temporarily dissociated to permit reagent access. For example, such an approach may be necessary when directing the cross-link to the hydrophobic core of a single polypeptide or to a buried residue pair of polypeptide complex having very high affinity among subunits. Any means known in the art may be used to reversibly denature polypeptide structure to permit reagent access to buried residue pairs. Such means include, but are not limited to, manipulating (increasing or decreasing) salt concentration or reaction temperature, or employing detergents, or such agents as guanidine HCl. As denaturing conditions are withdrawn (e.g., by dialysis) and the polypeptide or complex begins to refold/reassociate, the catalyst and oxidizing reagents may be added, as described above.

5.15. Purification of Cross-Linked Complexes

The cross-linked polypeptide or complex may be isolated and purified from proteins in the reaction that failed to cross-link, or any other undesirable side-products, by standard methods including chromatography (e.g., sizing column chromatography, glycerol gradients, affinity), centrifugation, or by any other standard technique for the purification of proteins. In specific embodiments it may be necessary to separate polypeptides that were not cross-linked, but that homo- or heterodimerize with other polypeptides due to high affinity binding. Separation may be achieved by any means known in the art, including, for example, addition of detergent and/or reducing agents.

Yield of functionally cross-linked polypeptides or complexes can be determined by any means known in the art, for example, by comparing the amount of stabilized complex, purified as described above, with the starting material. Protein concentrations are determined by standard procedures, such as, for example, Bradford or Lowrie protein assays. The Bradford assay is compatible with reducing agents and denaturing agents (Bradford, M. Anal. Biochem.; vol. 72: pp. 248, 1976), the Lowry assay is better compatibility with detergents and the reaction is more linear with respect to protein concentrations and read-out (Lowry, O. J. Biol. Chem.; vol. 193: pp. 265, 1951).

5.16. Assay of a Cross-linked Polypeptide or Complex 5.16.1. Retained Function Functionality Depending on the nature of the polypeptide or polypeptide complex, retained functionality can be tested, for example, by comparing the functionality of the cross-linked complex, cross-linked as described above, with that of the polypeptide or complex before stabilization, cross-linked or stabilized by another method, or naturally stabilized by a post-translational modification that, for example, regulates the association of certain polypeptides. Assays for retained functionality can be based, for example, on the biochemical properties of the protein in in vitro assay systems. Alternatively, the polypeptide or complex can be tested for functionality by using biological assay systems. For example, the activity of a kinase can be tested in in vitro kinase assays, and a growth factor, such as a member of the IL-8 family, can be tested for activity in chemotactic cell migration assays or beta-glucuronidase release assays (Leong S. R. et al. Protein Sci.; vol. 6(3): pp: 609–17, 1997). As another example, retained enzymatic activity of a biocatalyst can be determined by any method known to one skilled in the art. The activity of an enzyme is preferably measured directly by comparing the activity of the enzyme on a substrate before and after stabilization, and quantitating the product of the reaction. As examples, such assays include, but are not limited to, visualization upon chromatographic separation of the compounds in the reaction, spectrophotometric and fluorometric analyses of reaction products, analysis of incorporated or released detectable markers, such as, for example, radioactive isotopes. Indirect methods, that include, but are not limited to, computational, structural, or other thermodynamic analyses, may also be used for the determination of the activity of the stabilized biocatalyst. More specifically, as an example of a biocatalyst, the activity of a lipase, or specifically the activity of carboxylesterases catalyzing the hydrolysis of long-chain acylglycerols, is determined by any method known in the art, including, but not limited to the measurement of the hydrolysis of p-nitrophenylesters of fatty acids with various chain lengths (>=C-10) in solution by spectrophotometric detection of p-nitrophenol at 410 nm. Where it is necessary to distinguish between lipases and esterases, the triglyceride derivative 1,2-O-dilauryl-rac-glycero-3-glutaric acid resorufin ester (available from Boehringer Mannheim Roche GmbH, Germany), may also be used as a substrate, yielding resorufin, which can be determined spectrophotometrically at 572 nm, or fluorometrically at 583 nm (Jaeger K-E et al. Annu. Rev. Microbiol. 1999. 53: pp. 315–51).

Specificity

Depending on the nature of the polypeptide or polypeptide complex, retained specificity can be tested, as examples, by comparing the specificity of the cross-linked polypeptide or complex with that of the polypeptide or complex before stabilization, cross-linked or stabilized by another method, or naturally stabilized by a post-translational modification. Assays for retained specificity can be based, for example, on enzymatic substrate specificity, or ELISA-type procedures. For example, the retained or resultant specificity of a lipase (carboxylesterase) may be determined by any method known to one skilled in the art. Non-limiting examples of such methods include using a number of fluorogenic alkyldiacylglycerols as substrates for an analysis of the biocatalyst's stereoselectivity. For a detailed description of such methods and of certain such compounds, see the article "New fluorescent glycerolipids for a dual wavelength assay of lipase activity and stereoselectivity" (Zandonella G. et al., 1997, J. Mol. Catal. B: Enzymn. 3: pp. 127–30).

5.16.2. Stability

In vitro

Stability of the polypeptide or complex may be tested in vitro in, for example but not limited to, time-course experiments incubating the polypeptide or complex at varying concentrations and temperatures. Polypeptide or complex stability may also be tested at various pH levels and under various redox conditions. For all of the above conditions, the remaining levels of functional polypeptides or polypeptide complexes is determined by assaying as described above (Functionality). In the above example of a biocatalyst, improved or altered stability of a stabilized polypeptide or complex can be determined by any method known to one skilled in the art. Such methods include, but are not limited to, calorimetric and/or structural analyses, thermodynamic calculations and analyses, and comparison of the activities of the stabilized and unstabilized enzymes under their optimal conditions and under suboptimal, or adverse reaction conditions, such as higher or lower temperature, pressure, pH, salt concentration, inhibitory compound, or enzyme and/or substrate concentration. Any of the above analyses may also include time course experiments directed to the determination of stabilized biocatalyst half-life and/or shelf-life. Stabilization of a biocatalyst according to the invention can also be evaluated in the context of other methods of biocatalyst stabilization. As non-limiting examples, the above enzymatic activities can be tested in immobilizing gels or other matrices, or in partial or pure organic solvents. Furthermore, a biocatalyst stabilized by any of the methods known in the art (such as directed evolution or designed mutagenesis, see Background) can also be subjected to the methods of the instant invention to achieve further stabilization.

In vivo

Pharmaceutical and therapeutic applications are best tested in vivo or under conditions that resemble physiological conditions (see also, below). The stability of the polypeptide or complex may be tested in, for example but not limited to, serum, incubating the polypeptide or complex in time-course experiments at various temperatures (e.g. 37, 38, 39, 40, 42, and 45° C.), and at different serum concentrations, and assaying for the remaining levels of functional polypeptides or complexes. Furthermore, stability of a polypeptide or complex in the cytoplasm may be tested in time-course experiments in cell-lysates, lysed under various conditions (e.g. various concentrations of various detergents) at different temperatures (e.g. 37, 38, 39, 40, 42, and 45° C.), and assaying for the remaining levels of functional polypeptides or complexes. More directly, stability in the cytoplasm may be tested in time-course experiments by scrape-loading tissue culture cells with stabilized polypeptide or complex and assaying for the remaining levels of function. The stability of the polypeptide or complex may also be tested by injecting it into an experimental animal and assaying for specific activity. Alternatively, the compound may be recovered from the animal at an appropriate time point, or several time points, and assayed for activity and stability, as described above.

5.16.3. Biodistribution

To determine the utility of a stabilized polypeptide or polypeptide complex more directly, biodistribution and/or other pharmacokinetic attributes may be determined. In a specific embodiment, a stabilized polypeptide or polypeptide complex may be injected into a model organism and assayed by tracing a marker, such as but not limited to, $^{125}$I or $^{18}$F radio labels (Choi C. W. et al. Cancer Research, vol. 55: pp. 5323–5329, 1995), and/or by tracing activity as described above (Colcher D. et al. Q. J. Nucl. Med. vol. 44(4): pp. 225–241, 1998). Relevant information may be obtained, for example, by determining the amount of functional polypeptide or polypeptide complex that can be expected to be pharmaceutically active due to its penetration of the specifically targeted tissue, such as, for example, a tumor. Half-life in the circulation and at the specifically targeted tissue, renal clearance, immunogenicity, and speed of penetration may also be determined in this context.

5.16.4. Animal and Clinical Studies

Utility of a stabilized polypeptide or complex can be determined directly by measuring its pharmacological activity, either in animal studies or clinically. In a specific embodiment, such measurements may include, for example, measurements with which tumor progression or regression is monitored upon treatment of an animal model or one or several patients with a stabilized polypeptide or complex designed as an anti-cancer pharmacological agent. In another embodiment, such measurements may include, for example, measurements of bone mass, such as x-ray measurements, upon treatment of an animal model or one or several patients with a stabilized polypeptide or complex designed as an anti-menopausal bone-loss pharmacological agent.

5.17. Troubleshooting 5.17.1. Polypeptide or Complex not Cross-Linked

If the polypeptide or polypeptides of a complex should not become cross-linked and stabilized by the above described reaction, as determined, for example, by non-reducing Sodium Dodecyl Sulphate Polyacrylamide Gel Electrophoresis (SDS PAGE), there may be several explanations and solutions to the problem.

Adjust Polypeptide Concentrations Salt/Osmolarity and/or pH Conditions

For the stabilization of a polypeptide complex, the least problematic explanation may be that the polypeptides, as they are not yet stabilized, do not form a sufficiently stable complex in solution for the cross-link to form under the present conditions of the reaction. This could, for example, be determined by immunoprecipitating one of the polypeptides by any method known in the art, and assaying for the presence and relative quantity of the other polypeptide(s) of the complex in the precipitate, for example, by Western blotting.

Should this be (one of) the problem(s), it may be possible to increase the strength of the polypeptides' association with each other by any known means in the art, including, but not limited to, by adjusting certain conditions of the reaction, such as, but not limited to, salt, Tris, or protein concentration, or by adjusting the pH of the reaction. If thereby the strength of the polypeptides' association is increased, for example, as determined by non-reducing SDS PAGE, the cross-link reaction should be tried again under these conditions.

The opposite could also be the problem: the polypeptides of a complex, or the polypeptide structures of a single polypeptide, associate with each other too tightly, the tyrosyl side-chains are not exposed to the catalyst or oxidizing reagents, and the dityrosine bond does not form. In such cases, the protein sub- or secondary structures or the polypeptides of a complex are first dissociated by any means known in the art, as described above, by adjusting, for example, but not limited to, the concentrations of salt, detergent, guanidine HCl, and/or any other agents that cause reversible denaturation, temperature, pressure, and/or reaction time. It may also, for example, be possible to add the oxidizing agent and catalyst at an earlier or later time-point, as the above conditions are reversed, as described above, and the polypeptide or polypeptide complex begins to refold/reassociate.

Increase Strength of Reaction Conditions

Should the cross-link not form in spite of appropriate polypeptide folding or good complex formation under the conditions of the reaction, the next solution could be to increase the strength of the conditions of the reaction, e.g. by increasing the concentration of the oxidizing reagent and/or of the catalyst. A preferred method would still use the minimal strength of the reaction required for the cross-link to form.

Identify Second-site Mutation

It may be possible, by screening a library of mutants of the polypeptide or polypeptide complex to be cross-linked, to identify second-site mutations that alter the fold and/or structure of the polypeptide or polypeptide complex in such a way, that the cross-link can form. Such second-site mutations may be identified by any methods known in the art, such as, for example, but not limited to, any of the in vitro evolutionary approaches (see above).

Direct Cross-linking Reaction to an Alternative Residue Pair

The cross-link may be directed to a pair of tyrosines that cannot be cross-linked due to structural elements not captured in the selection process. Should the above approaches not cause the cross-link to form between the selected residues of a pair encoding tyrosine under any conditions, another residue pair may be selected, and the cross-link reaction tried again, where necessary adjusting the reaction conditions, as described above.

Combined Approach

It may be necessary to employ one, two, any, several, or all of the above approaches to trouble-shooting to achieve the desired stabilizing dityrosine bond.

5.17.2. Compromise Functionality of Polypeptide or Complex

Decrease Strength of Reaction Conditions

Reducing the strength of the reaction by adjusting, for example, but not limited to, the concentration of either the catalyst or the oxidizing reagent, the temperature, pressure, and/or reaction time, may result in a stabilized polypeptide or polypeptide complex with better retained functionality.

Adjust Protein Concentrations, Salt/Osmolarity and/or pH Conditions

Non-specific cross-link reactions may compromise the functionality of the polypeptide or polypeptide complex, that may occur under certain reaction conditions, such as, but not limited to, high protein concentrations relative to the optimum, certain pH levels, or salt, detergent, denaturing, and/or any other concentrations of the components in the reaction. These conditions may be adjusted to minimize or eliminate the formation of non-specific, compromising dityrosine bonds.

Identify Second-site Mutation

It may be possible, by screening a library of mutants of the polypeptide or polypeptide complex to be cross-linked, to identify second-site mutations that alter the fold and/or structure of the polypeptide or polypeptide complex in such a way, that the its functionality upon cross-linking is restored. Such second-site mutations may be identified by any methods in the art, such as, for example, but not limited to, any of the in vitro evolutionary approaches (see above).

Direct Cross-linking Reaction to an Alternative Residue Pair

As often input data for the selection process is less than completely accurate, as or for any other reason, the selected residue pair may yield residue pairs that distort the overall structure of the polypeptide or polypeptide complex, and thereby compromise or alter its functionality. Should this be the case, another pair that the selection process yielded should be mutated such that both residues encode tyrosine, and the cross-link reaction should be tried again, and retained functionality tested.

Combined Approach

Of course, it may be necessary to employ one or more of the above approaches to trouble-shooting to achieve the desired stabilizing dityrosine bond.

5.18. Software for Selection Process

This invention provides software that permits automated selection of suitable residue pairs at which a di-tyrosine bond can be placed. Such software can be used in accordance with the geometrical, physical, and chemical criteria described above (see especially Identification of Suitable Residue Pairs for the Reaction), and a Residue Pair Selection Flowchart such as is set forth in Section 6 below. As described above, a successive array of Filters is implemented and residue pairs that "pass" through the filters comprise the selected residue pairs (FIG. 14, left side). Alternatively, filters can be implemented to process all residue pairs in a parallel array (FIG. 14, right side). Residue pairs that "pass" through a filter define that filter's set of passed pairs. In a preferred embodiment, residue pairs that are in all filters' passed sets (i.e. residue pairs that form the intersection of all filter sets) are the selected pairs. The filter requirements are as described above (Identification of Suitable Residue Pairs for the Reaction).

5.19. Pharmaceutical Composition

In one embodiment, this invention provides a pharmaceutical composition comprising an effective amount of a stabilized polypeptide or polypeptide complex, and a pharmaceutically acceptable carrier. As used herein, "an effective amount" means an amount required to achieve a desired end result. The amount required to achieve the desired end result will depend on the nature of the disease or disorder being treated, and can be determined by standard clinical techniques. In addition, in vitro assays may optionally be employed to help identify optimal dosage ranges. The precise dose to be employed will also depend on the route of administration and the seriousness of the disease or disorder, and should be decided according to the judgment of the practitioner and each subject's circumstances. Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, pharmaceutical compositions of the invention can be delivered in a controlled release system. In one embodiment, a pump may be used (see Langer, supra; Sefton, CRC Crit. Ref. Biomed. Eng.; vol. 14: pp. 201, 1987; Buchwald et al., Surgery; vol. 88: pp. 507, 1980; Saudek et al., N. Engl. J. Med.; vol. 321: pp. 574, 1989). In another embodiment, polymeric materials can be used (see Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, N.Y., 1984; Ranger and Peppas, J. Macromol. Sci. Rev. Macromol. Chem.; vol. 23: pp. 61, 1983; see also Levy et al. Science; vol. 228: pp. 190, 1985; During et al. Ann. Neurol.; vol. 25: pp. 351, 1989; Howard et al. J. Neurosurg; vol. 71: pp. 105, 1989). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138, 1984).

Other controlled release systems are discussed in the review by Langer (Science; vol. 249: pp. 527–1533, 1990).

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

5.20. Consideration for Pharmaceutical Composition

Stabilized polypeptides or polypeptide complexes of the invention should be administered in a carrier that is pharmaceutically acceptable. The term "pharmaceutically acceptable" means approved by a regulatory agency of the Federal or a state government or listed in the U.S. Pharmacopeia or other generally recognized pharmacopeia or receiving specific or individual approval from one or more generally recognized regulatory agencies for use in animals, and more particularly in humans. The term "carrier" refers to a diluent, adjuvant, excipient, or vehicle with which the therapeutic is administered. Such pharmaceutical carriers can be sterile liquids, such as water, organic solvents, such as certain alcohols, and oils, including those of petroleum, animal, vegetable or synthetic origin, such as peanut oil, soybean oil, mineral oil, sesame oil and the like. Buffered saline is a preferred carrier when the pharmaceutical composition is administered intravenously. Saline solutions and aqueous dextrose and glycerol solutions can also be employed as liquid carriers, particularly for injectable solutions. The composition, if desired, can also contain minor amounts of wetting or emulsifying agents, or pH buffering agents. These compositions can take the form of solutions, suspensions, emulsion and the like. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration. In a preferred embodiment, the composition is formulated in accordance with routine procedures as a pharmaceutical composition adapted for intravenous administration to human beings. Typically, compositions for intravenous administration are solutions in sterile isotonic aqueous buffer.

6. EXAMPLE I

Stabilized Fv Fragments

The following example illustrates certain variations of the methods of the invention for protein and protein complex stabilization. This example is presented by way of illustration and not by way of limitation to the scope of the invention.

6.1. Introduction

Several polypeptides and polypeptide complexes with significant commercial value have been identified in recent years, and furthermore, several modular domains have been identified that mediate protein-protein interactions. For many of these domains, the interaction sites with other proteins have also been mapped.

In the following section, methods of stabilizing one such complex, an Fv fragment complex, for which an abundance of data is available, are described in detail. Specifically, described below are the assembly of relevant databases for the selection process, the selection process itself, the introduction of point mutations, bacterial expression of the polypeptides and their purification, adjustment of the cross-link reaction conditions, the cross-link reaction itself, and analysis of the resulting stabilized complex.

The input data for the 2-D database is obtained from Weir's Handbook of Experimental Immunology I. Immunochemistry and Molecular Immunology, Fifth Edition. The input data for the 3-D database is obtained from the Brookhaven National Laboratory Protein Database. The derivative data relevant to the selection process in both databases is calculated as described. The selection process is carried out using a set of filters that is convenient and appropriate for this application of the instant invention.

Point mutations to tyrosine (directing the cross-link reaction) are introduced according to the final selection of the selection process, and point mutations to phenylalanine (limiting the cross-link reaction) according to the specific sequence of each Fv fragment and the corresponding and relevant structural information contained in the 3-D database. The polypeptides of the complex are expressed bacterially as GST fusion proteins, and purified over a GT-affinity column. The purified polypeptides of the complex are proteolytically cleaved from the GST parts of the fusion proteins, and the GST polypeptide is removed, again using a GT affinity column.

The minimally required reaction conditions are adjusted using a construct with the mutations to phenylalanine, but lacking the mutations to tyrosine, and the cross-link reaction is then carried out with the constructs containing both sets of point mutations. The efficiency of the reaction is tested for, and the resulting, stabilized Fv fragments are then tested for retained affinity, stability, immunogenicity, and biodistribution characteristics.

6.2. Advantages of the Tyrosyl-Tyrosyl Cross-Link for Fv Fragments

The underlying chemistry of the technology covered by the present invention causes an oxidative cross-link to form between reactive side-chains of proteins that form stable complexes. Because the cross-linking reaction is catalyzed, once established, the cross-link is stable in the absence of the catalyst under a broad range of pH and redox conditions. The cross-link reaction requires very close proximity between the molecules that will cross-link and therefore only occurs between molecules that normally interact and associate closely in solution and is therefore limited to molecules that have legitimate functional interactions.

Thus, the current invention describes a new technology that will allow stabilization of immunoglobulin-derived conjugates and result in both a very high degree of stability and minimal immunogenicity in therapeutic contexts. This technology is designed to improve on preceding, and complement compatible, technologies.

The resultant stabilized Fv fragments will have the following characteristics:

1. The conjugates will be stable under a broad range of pH and redox conditions and at high protein concentrations.

2. The resultant cross-linked complex will be minimally immunogenic since no exposed residues are altered.

This Fv fragment stabilization technology is well suited for the development of new products with novel applications, the improvement of existing immunoglobulin-based products, and the complementation of existing technologies for the development of novel immunoglobulin applications.

6.3. Fv Fragment Applications

There is a wide spectrum of potential applications for immunoglobulin-based products, the limits of which are determined by the following factors:

The target must be in an environment that is accessible to immunoglobulin-derived products, such as, for example, serum, the extracellular matrix, the brain, or the intracellular space by way of liposomes (Hoffman R. M. J. Drug Target.; vol. 5(2): pp. 67–74, 1998) or peptide induced cellular uptake (Schwarze S. R. et al. Science; vol. 285: pp. 1565–72, 1999). For intracellular applications of immunoglobulin, see Bosilevac J. M. et al. J. Biol. Chem.; vol. 273(27): pp. 16874–79, 1998; Graus-Porta D. et al. Mol. Cell Biol.; vol 15: pp. 1182–91, 1995; Richardson J. H. et al. Proc. Nat. Acad. Sci., USA; vol. 92: pp. 3137–41, 1995; Maciejewski J. P. et al. Nat. Med.; vol. 1: pp. 667–73, 1995; Marasco W. A. et al. Proc. Nat. Acad. Sci., USA; vol. 90: pp. 7889–93, 1993; Levy MintZ P. et al. J. Virol.; vol. 70: pp. 8821–32, 1996; Duan L. et al. Hum. Gene Ther.; vol. 6(12): pp. 1561–73, 1995; and Kim S. H. et al. Mol. Immunol.; vol. 34(12–13): pp. 891–906, 1997. A favorable environment is present in all tissues and organs that are reached by the blood supply, and where the target molecule is present on the cell surface or in the extra-cellular matrix. Since the functionality of iminunoglobulin-derived Fv fragments is primarily to bind to target molecules, binding to the target should preferably suffice to accomplish the desired therapeutic or diagnostic effect. Catalytic functionality is, however, also known for immunoglobulin, and may therefore also be achieved in pharmacological and/or industrial contexts (Pluckthun A. et al. Ciba Found. Symp.; vol. 159: pp. 103–12; discussion 112–7, 1991; Kim S. H. et al. Mol. Immunol, vol. 34: pp. 891–906, 1997).

There is a multitude of applications of potential immunoglobulin-based applications that meet these criteria, and it is the purpose of the following paragraphs only to point out certain relevant applications, as examples.

6.3.1. Drug Delivery/Tissue Targeting

Many existing applications of immunoglobulin therapy make use of antibody's ability to direct therapeutic agents to the targeted tissues. Such therapeutic agents have thus far been toxins and radioisotopes targeted to tumors by linkage to anti-tumor associated antigen or anti-tumor specific antibodies, on the one hand, and diagnostic agents, i.e. antibodies linked to an imaging agent, on the other hand.

6.3.2. Modulation of Extra-Cellular Biochemical Processes

There are a multitude of biochemical processes that are of therapeutic, and thus of commercial relevance that occur in extra-cellular milieus, such as blood serum. One example of such a process is the process of blood clotting. In this example, the immunoglobulin binds to one of the proteins involved in the biochemical cascade of reactions that lead to the formation of blood clots, and interrupts this cascade, thereby blocking the formation of blood clots. The therapeutic value of being able to inhibit the formation of blood clots, indeed, spurred the development of one of the first immunoglobulin-based pharmaceutical to enter the market.

6.4. Selection of Optimal Residues for Tyrosyl-Tyrosyl Cross-Link

The selection process consisted of a series of statistical tests or 'filters' aimed at successively narrowing down the residue pairs most likely to result in a cross-linked heavy chain-light chain tyrosine pair that minimally alter the Fv fragment's' structural characteristics.

6.4.1. Data used for the Analysis

Residue amino acid usage data is data compiled on amino acids encoded and expressed at each residue of known and sequenced Fv fragments. It is collected in, and obtained from, the publication "Proteins of Immunological Interest", Kabat and Wu, Government Printing Office, NIH Publication 91–3242, 1991 ("K&W"). The amino acid sequences in this publication are ordered according to a standardized numbering system that takes into account the gene structure of the heavy and light chain variable regions. In the variable regions of the heavy and light chains alike, four Framework Region segments (FRs)—which are relatively conserved—are interspersed by three—highly variable—Complementarity Determining Regions (CDRs). The CDRs contain the amino acids that determine the antibody's specificity, and that physically contad the antigen. Aligning ali sequences according to the K&W numbering system was very important for the purpose of performing a statistical analysis as described in this example since the corresponding residues of the FRs are thereby always aligned, regardless of the varying sequence lengths of the interspersed CDRs. This ensured that statistical measurements were made with sets of data containing appropriate and comparable data points. Coordinate data for distance calculations of all atoms other than hydrogens of 17 Fv fragments from crystallographically solved immunoglobulin structures was downloaded from the protein structure database Brookhaven National Laboratory (FIG. 5). These data provide the three-dimensional coordinates (x, y, and z) for each atom in a solved structure, expressed in metric units, i.e. Angstroms ($10^{-10}$ m, Å). With this data it was possible to calculate the three-dimensional distances between any desired atoms (e.g., amino alpha and beta carbon atoms) and to calculate statistical measurements of the variability of such distance between the different Fv fragments in the sample being analyzed (FIGS. 5, 6, and 7).

6.4.2. Selection Methodology

Optimal residues, to which the cross-link reaction is directed, were selected by a series of filters based on the statistical measurements of values in databases compiled for the purposes of this selection. These databases contain numeric measurements of (1) alpha carbon spacing, (2) beta carbon spacing and the difference between the alpha and beta distances, and (3) residue amino acid usage (see below).

6.5. Filter 1

Elimination of Residue Pairs with Glycines

Glycine is the smallest of the amino acids and has no beta carbon and is often associated with positional flexibility of protein structures. Substitution of a glycine with one of the largest amino acids, tyrosine, would likely have too great an impact on the overall structure of the protein complex, and thereby on the antigen-binding characteristics of the cross-linked Fv fragment. Therefore, as a first cut, from among all candidate residue pairs of the Framework Regions, those pairs, of which one of the residues is most frequently a glycine (as determined by comparison with the K&W data) were eliminated a priori. For the purposes of this analysis 'most frequent' occurrence of a particular amino acid at a given residue was defined as occurrence in more than 75% of the sample.

TABLE 1

Heavy chain-light chain candidate pairs with average alpha carbon distance measurements mx, within the range of 5.70Å to 11.74Å (sorted by K&W numbering, first on the light chain, second on heavy chain positions).

| Light | Heavy | AVERAGE | STDEV | Light | Heavy | AVERAGE | STDEV |
|---|---|---|---|---|---|---|---|
| 36 | 45 | 10.38 | 0.23 | 44 | 91 | 9.33 | 0.33 |
| 36 | 103 | 10.99 | 0.31 | 44 | 92 | 10.91 | 0.40 |
| 37 | 45 | 11.49 | 0.36 | 44 | 93 | 9.74 | 0.29 |
| 38 | 39 | 11.49 | 0.18 | 44 | 103 | 6.92 | 0.30 |
| 38 | 45 | 10.17 | 0.43 | 44 | 105 | 8.95 | 0.55 |
| 38 | 103 | 11.26 | 0.41 | 45 | 93 | 10.43 | 0.41 |
| 40 | 41 | 11.27 | 1.50 | 45 | 103 | 7.40 | 0.41 |
| 40 | 43 | 11.68 | 1.34 | 45 | 105 | 10.95 | 0.45 |
| 42 | 39 | 11.04 | 0.84 | 46 | 93 | 10.78 | 0.40 |
| 42 | 89 | 10.28 | 0.99 | 46 | 94 | 11.19 | 0.25 |
| 42 | 90 | 11.72 | 0.88 | 46 | 103 | 8.98 | 0.33 |
| 42 | 91 | 10.5 | 0.66 | 85 | 43 | 11.04 | 0.49 |
| 42 | 103 | 10.13 | 0.34 | 85 | 45 | 10.93 | 0.37 |
| 42 | 105 | 7.14 | 0.40 | 86 | 45 | 10.63 | 0.35 |
| 42 | 107 | 11.18 | 0.82 | 87 | 43 | 11.64 | 0.32 |
| 43 | 4 | 11.50 | 0.56 | 87 | 45 | 8.19 | 0.25 |
| 43 | 37 | 10.94 | 0.87 | 87 | 46 | 10.90 | 0.33 |
| 43 | 38 | 10.97 | 0.98 | 88 | 45 | 10.04 | 0.10 |
| 43 | 39 | 10.34 | 0.79 | 88 | 46 | 11.69 | 0.21 |
| 43 | 45 | 10.78 | 0.71 | 98 | 37 | 10.24 | 0.31 |
| 43 | 89 | 9.95 | 0.71 | 98 | 38 | 11.25 | 0.25 |
| 43 | 90 | 10.23 | 0.72 | 98 | 39 | 11.17 | 0.20 |
| 43 | 91 | 8.04 | 0.71 | 98 | 43 | 11.60 | 0.39 |
| 43 | 92 | 10.21 | 0.59 | 98 | 45 | 6.49 | 0.18 |
| 43 | 93 | 10.14 | 0.65 | 98 | 46 | 6.66 | 0.29 |
| 43 | 103 | 6.74 | 0.51 | 98 | 48 | 7.65 | 0.57 |
| 43 | 105 | 5.74 | 0.44 | 98 | 49 | 11.37 | 0.58 |
| 43 | 107 | 10.66 | 0.62 | 100 | 39 | 11.42 | 0.29 |
| 44 | 37 | 10.58 | 0.39 | 100 | 43 | 8.27 | 0.41 |
| 44 | 38 | 11.31 | 0.50 | 100 | 45 | 7.82 | 0.27 |
| 44 | 39 | 10.73 | 0.48 | 100 | 46 | 9.56 | 0.46 |
| 44 | 45 | 9.43 | 0.48 | 102 | 43 | 11.47 | 0.36 |

6.6. Filter 2

Identification of Appropriately Spaced Residue Pairs

To find residue pairs spaced appropriately for a tyrosyl-tyrosyl bond, the alpha carbon to alpha carbon distances from every residue in the light chain to every residue in the heavy chain in Fv fragments represented in the Brookhaven National Protein Structure Database were calculated in a 3D database. This calculation was performed by applying Pythagorean geometry to the 3D coordinates of the alpha carbons (FIG. 6). For every combination of heavy and light chain residues, the average, standard deviation, range and median of the alpha carbon-alpha carbon distance was calculated on the Fv fragments in the sample (FIG. 7). Based on the calculations above, as a second cut, all residue pairs were selected whose alpha carbons are spaced at an average, m, within the selection range. The range that was selected for was the following:

Min 5.70 Å, Max 11.74 Å.

The optimal distance (T) was calculated by averaging the maximum and the minimum of the range. Therefore, $T = (5.70 \text{ Å} + 11.74 \text{ Å})/2 = 8.72 \text{ Å}.$ In this example, 64 residue pairs met this criterion, listed in Table 1.

6.7. Filter 3

Identification of Residue Pairs with Sufficient Positional Flexibility

In order to identify residue pairs at which substitution to tyrosine is minimally disruptive, residues pairs with significant positional flexibility were selected. Therefore, residue pairs were eliminated from among those in Table 1 in which the optimal distance, 8.72 Å, does not fall within 2 times of that specific residue pair's standard deviation from its average. In this example, 36 residue pairs met this criterion. Furthermore, the relative positional flexibility of the remaining 12 candidate residue pairs was rated according to the following formula:

Rating $I = a_x^2 / \sigma_x$.

$a_x = T - \mu_x + 2\sigma_x$, for all $\mu_x \geq T$ $a_x = \mu_x + 2\sigma_x - T$, for all $\mu_x \geq T$ $T$ = optimal distance $\mu_x$ = the average distance for any given residue pair $\sigma_x$ = standard deviation of the distance for any given residue pair Thus, residues that scored highly under this metric are those that (i) have an average spacing close to the optimal distance, and/or (ii) have a large standard deviation. The remaining 12 residue pairs are listed, sorted by Rating I in Table 2.

TABLE 2

Residue pairs of Table 1 selected[1] and rated by Rating I[2].

| Heavy | Light | Rating I | AVG | STDEV |
|---|---|---|---|---|
| 44 | 105 | 1.35 | 8.95 | 0.55 |
| 43 | 91 | 0.76 | 8.04 | 0.71 |
| 46 | 103 | 0.49 | 8.98 | 0.33 |
| 100 | 43 | 0.33 | 8.27 | 0.41 |
| 43 | 37 | 0.26 | 10.9 | 0.87 |
| 42 | 89 | 0.17 | 10.3 | 0.99 |
| 40 | 41 | 0.14 | 11.3 | 1.50 |
| 44 | 45 | 0.13 | 9.43 | 0.48 |
| 43 | 89 | 0.06 | 9.95 | 0.71 |
| 100 | 46 | 0.01 | 9.56 | 0.46 |
| 98 | 48 | 0.01 | 7.56 | 0.57 |
| 44 | 91 | 0.01 | 9.33 | 0.33 |

[1] Selection criterion: optimal distance (T) must fall within the range of the residue pair's specific distance average ($\mu_x$) +/− 2 times the residue pair's specific standard deviation ($\sigma_x$).
[2] Rating I formula: $\alpha^2_x/\sigma_x$, where T is the optimal distance, and $\alpha_x = T - \mu_x + 2\sigma_x$, for all $\mu_x \geq T$, and $a_x = \mu_x + 2\sigma_x - T$, for all $\mu_x \leq T$.

6.8. Filter 4

Side-Chain Orientation

In the space that the heavy and light chains occupy, the tyrosine side chains should be oriented toward each other for a cross-link to form with minimal structural distortion. The difference between the alpha carbon distance (i.e. the backbone carbon distance; FIG. 6) and the beta carbon distance (i.e. the distance between the first carbons in each side chain; FIG. 8) of each residue pair was calculated as a proxy, i.e. an estimate of the orientation of the side chains relative to each other (FIG. 9).

The range that was selected for was the following:

Min −0.5 Å, Max 2.0 Å.

The optimal distance difference (D) was calculated by averaging the maximum and the minimum of the range. Therefore, $D = (-0.5 \text{ Å} + 2.0 \text{ Å})/2 = 0.75 \text{ Å}.$ Again, based on 3D coordinate geometry, for each residue pair, the distance between the beta carbons was calculated (FIG. 8). The beta distance was then subtracted from the alpha distance of the residue pair (FIG. 9). This filter was based on whether the average difference in the alpha and beta distances of a residue pair (FIGS. 10 and 11) falls within the estimated optimal range. In this example, 12 residue pairs met this criterion, listed in Table 3.

TABLE 3

Residue pairs of Table 2 selected by average alpha-beta distance difference.

| Heavy | Light | Rating I | AVG | STDEV | AVG | STDEV |
|---|---|---|---|---|---|---|
| 91 | 43 | 0.76 | 8.04 | 0.71 | 1.33 | 0.70 |
| 45 | 43 | 0.56 | 10.78 | 0.71 | −0.04 | 0.31 |
| 103 | 46 | 0.49 | 8.98 | 0.33 | 0.81 | 0.18 |
| 39 | 42 | 0.48 | 11.04 | 0.84 | 0.21 | 0.14 |
| 91 | 42 | 0.30 | 10.5 | 0.66 | −0.14 | 0.17 |
| 37 | 43 | 0.26 | 10.94 | 0.87 | 0.81 | 0.59 |
| 89 | 42 | 0.17 | 10.28 | 0.99 | 0.01 | 0.06 |
| 92 | 43 | 0.15 | 10.21 | 0.59 | −0.23 | 0.61 |
| 89 | 43 | 0.06 | 9.95 | 0.71 | 0.71 | 0.36 |
| 93 | 43 | 0.02 | 10.14 | 0.65 | 1.07 | 0.73 |
| 48 | 98 | 0.01 | 7.65 | 0.57 | 0.87 | 0.17 |
| 30 | 43 | 0.00 | 10.34 | 0.79 | 0.41 | 0.28 |

Furthermore, analogously to the selection based on alpha carbon distances, those pairs were eliminated for which the optimal average distance difference, 0.75 Å, does not fall within 2 times that residue pair's specific standard deviation from its average.

Rating II = $a_x^2/\sigma_x$ $\alpha_x = D - u_x + 2\sigma_x$, for all $\mu_x \geq D$ $\alpha_x = u_x + 2\sigma_x - D$, for all $\mu_x \geq D$ D = optimal distances difference $\mu_x$ = the average distance difference for any given residue pair $\sigma_x$ = standard deviation of the distance difference for any given residue pair Of the set of potential residue pairs listed in Table 4, five pairs met these criteria. This set of potential residue pairs is listed in Table 5.

TABLE 4

Residue pairs of Table 5 selected[1] and rated according to Rating II[2]

| | | Difference between C-alpha and C-beta distances | | | Alpha Carbon distance | | |
|---|---|---|---|---|---|---|---|
| Heavy | Light | Rating II | Average | Stdev | Rating I | Average | Stdev |
| 92 | 43 | 0.10 | −0.23 | 0.61 | 0.15 | 10.21 | 0.59 |
| 39 | 43 | 0.17 | 0.41 | 0.28 | 0.00 | 10.34 | 0.79 |
| 48 | 98 | 0.30 | 0.87 | 0.17 | 0.01 | 7.65 | 0.57 |
| 103 | 46 | 0.49 | 0.81 | 0.18 | 0.49 | 8.98 | 0.33 |
| 91 | 43 | 0.96 | 1.33 | 0.70 | 0.76 | 8.04 | 0.71 |
| 89 | 43 | 1.27 | 0.71 | 0.36 | 0.06 | 9.95 | 0.71 |
| 93 | 43 | 1.79 | 1.07 | 0.73 | 0.02 | 10.14 | 0.65 |
| 37 | 43 | 2.10 | 0.81 | 0.59 | 0.26 | 10.94 | 0.87 |

[1]Selection criterion: Optimal difference in alpha and beta distances (D) must fall within the range of the residue pair's average alpha-beta distance-difference ($\delta_x$) 2 × the residue pair's specific standard deviation ($\sigma_x$).
[2]Rating II formula: $\alpha_x^2/\sigma_x$, whereby D is the optimal distance difference, and $\alpha_x = D - \delta_x + 2\sigma_x$, for all $\delta_x \geq D$, and $\alpha_x = \delta_x + 2\sigma_x - D$, for all $\delta_x \leq D$.

Note that optimal alpha-alpha distance and alpha-beta distance difference (Target) also falls comfortably within the range of actually measured values of most of the residue pairs selected, as shown in Table 5. This is important, because it further underscores the likelihood that the selected candidate pairs will result in cross-linked tyrosine side chains that minimally disrupt the Fv fragment structure and function.

TABLE 5

Average, median, standard deviation, and range of actually measured alpha-alpha distances and alpha-beta distance differences. The remaining residue pairs are identified in the top two rows by their heavy and light chain K&W residue numbers.

| | | Heavy | 37 | 39 | 89 | 91 | 92 | 93 | 103 | 48 |
|---|---|---|---|---|---|---|---|---|---|---|
| | | Light | 43 | 43 | 43 | 43 | 43 | 43 | 46 | 98 |
| Alpha Carbon Distance | Average | | 10.94 | 10.34 | 9.95 | 8.04 | 10.21 | 10.14 | 8.98 | 7.65 |
| | Stdev | | 0.87 | 0.79 | 0.71 | 0.71 | 0.59 | 0.65 | 0.33 | 0.57 |
| | Max | | 13.23 | 12.37 | 11.75 | 9.82 | 11.81 | 11.81 | 9.63 | 8.68 |
| | Min | | 9.94 | 9.63 | 9.05 | 7.32 | 9.56 | 9.42 | 8.39 | 6.78 |
| | Median | | 10.81 | 10.10 | 9.80 | 7.92 | 9.99 | 9.95 | 8.95 | 7.89 |
| Ca–Cb Difference | Average | | 0.81 | 0.41 | 0.71 | 1.33 | −0.23 | 1.07 | 0.81 | 0.87 |
| | Stdev | | 0.59 | 0.28 | 0.36 | 0.70 | 0.61 | 0.73 | 0.18 | 0.17 |
| | Max | | 1.42 | 0.84 | 1.17 | 2.02 | 0.33 | 1.74 | 1.09 | 1.37 |
| | Min | | −0.64 | −0.10 | −0.08 | −0.25 | −1.86 | −0.69 | 0.40 | 0.63 |
| | Median | | 1.03 | 0.45 | 0.75 | 1.65 | 0.05 | 1.29 | 0.77 | 0.81 |

6.9. Filter 5

Amino Acid Side-Chain Usage

Since residue pairs are to be substituted with tyrosine such that the substitutions are minimally disruptive to the structure and function of the resulting cross-linked complex, residue pairs were selected from among those in Tables 4 and 5 such that the properties of the original amino acid side-chains were as similar as possible to those of tyrosine. The principal side chain properties that were measured are (i) van der Waals volume and (ii) hydrophobicity. These measurements were used as proxies for the size and charge of the amino acid side chains, respectively.

At each residue, every occurring amino acid side chain was given a numeric value representing its van der Waals volume and its hydrophobicity (FIG. 12). Based on amino acid usage data for these residues (Kabat & Wu), the average and standard deviation of the residue's van der Waals volume and hydrophobicity were calculated, both weighted, and un-weighted by the frequency at which the specific side chain occurs at this residue. A weighted statistical measurement is calculated on every value present in the sample (n=number of sequences in 2-D database), and an un-weighted statistical measurement is calculated on the value of each occurring amino acid (n=20 maximally) (FIG. 13).

For example, given 10 sequences in a database, whereby at a given residue alanine occurs 8 times, and leucine twice, the weighted average of the van der Waals volumes would be:

(8 × ala value + 2 × leu value)/10 = (8 × 67 + 2 × 124)/10 = 78.4.

In the same example, the un-weighted average would be (ala value + leu value)/2 = (67 + 124)/2 = 95.5.

The numeric values of all 20 amino acids of both van der Waals volume and hydrophobicity used for the selection are listed in Table 6.

Each of the 6 residue pairs identified in the structural analysis was examined for its ability to be "conservatively" substituted with two tyrosine residues, by comparing the pair's average van der Waals and hyrophobicity scores and their standard deviations with those of a tyrosine pair.

TABLE 6

Numeric values of amino acid side chain van der Waals volumes (Richards, F. M._J. Mol. Biol. 82, 1–14, 1974) and hydrophobicity (Eisenberg, D._Ann. Rev. Biochem. 53, 595–623, 1984).

| Amino Acid | Van der Walls volumes [$A^3$] | Hydrophobicity |
|---|---|---|
| Ala | 67 | 0.62 |
| Arg | 148 | −2.50 |
| Asn | 96 | −0.78 |
| Asp | 91 | −0.90 |
| Cys | 86 | 0.29 |
| Gln | 114 | −0.85 |
| Glu | 109 | −0.79 |
| Gly | 48 | 0.48 |
| His | 118 | −0.40 |
| Ile | 124 | 1.40 |
| Leu | 124 | 1.10 |
| Lys | 135 | −1.50 |
| Met | 124 | 0.64 |
| Phe | 135 | 1.20 |
| Pro | 90 | 0.12 |
| Ser | 73 | −0.18 |
| Thr | 93 | −0.05 |
| Trp | 163 | 0.81 |
| Tyr | 141 | 0.26 |
| Val | 105 | 1.10 |

For each of the residues listed in Table 5, the average van der Waals volumes and hydrophobicity values and their standard deviations, weighted and unweighted, are listed in Table 7 and 8, respectively.

TABLE 7

Van der Waals scores for residue pairs and comparison to a tyr-tyr pair.

| | Heavy | 37 | 39 | 89 | 91 | 92 | 93 | 103 | 48 |
|---|---|---|---|---|---|---|---|---|---|
| | Consensus | VAL | GLN | VAL | TYR | CYS | ALA | TRP | VAL |
| | Average | 109 | 113 | 110 | 141 | 86 | 69 | 160 | 110 |
| | Stdev | 8 | 12 | 12 | 1 | — | 9 | 11 | 9 |
| unweighted | Average | 116 | 103 | 122 | 138 | 86 | 78 | 136 | 116 |
| | Stdev | 10 | 51 | 18 | 4 | — | 26 | 27 | 10 |
| | Light | 43 | 43 | 43 | 43 | 43 | 43 | 46 | 98 |
| | Consensus | ALA | ALA | ALA | ALA | ALA | ALA | LEU | PHE |
| weighted | Average | 72 | 72 | 72 | 72 | 72 | 72 | 124 | 135 |
| | Stdev | 14 | 14 | 14 | 14 | 14 | 14 | 3 | 2 |
| unweighted | Average | 94 | 94 | 94 | 94 | 94 | 94 | 118 | 128 |
| | Stdev | 24 | 24 | 24 | 24 | 24 | 24 | 11 | 6 |
| | Heavy | 37 | 39 | 89 | 91 | 92 | 93 | 103 | 48 |
| | Light | 43 | 43 | 43 | 43 | 43 | 43 | 46 | 98 |
| | 2 × tyr value | 282 | 282 | 282 | 282 | 282 | 282 | 282 | 282 |
| | Comb. value[1] | 181 | 185 | 182 | 213 | 158 | 141 | 283 | 245 |
| weighted | Difference[2] | 101 | 97 | 100 | 69 | 124 | 141 | 1 | 38 |
| | Comb. Stdev.[3] | 22 | 26 | 26 | 15 | 14 | 23 | 14 | 11 |
| | Rating III[4] | 0.21 | 0.27 | 0.26 | 0.21 | 0.11 | 0.16 | 10.39 | 0.28 |
| | 2 × tyr value | 282 | 282 | 282 | 282 | 282 | 282 | 282 | 282 |
| | Comb. value[1] | 210 | 197 | 216 | 232 | 180 | 172 | 253 | 244 |
| unweighted | Difference[2] | 72 | 85 | 66 | 50 | 102 | 110 | 29 | 39 |
| | Comb. Stdev.[3] | 35 | 75 | 43 | 29 | 24 | 50 | 38 | 17 |
| | Rating IV[4] | 0.49 | 0.89 | 0.64 | 0.57 | 0.24 | 0.46 | 1.32 | 0.43 |

[1]Sum of the residue pair's average van der Waals values
[2]Size of the difference (square root of squared difference) between the sum of the value for two tyrosine residues (282) and the sum of the residue pairs' average values ([1])
[3]Sum of both residue's standard deviation
[4]Formula used: Stdev/Difference ($^3/_2$)

TABLE 8

Hydrophobicity scores for residue pairs and comparison to a tyr-tyr pair.

| | Heavy | 37 | 39 | 89 | 91 | 92 | 93 | 103 | 48 |
|---|---|---|---|---|---|---|---|---|---|
| | Consensus | VAL | GLN | VAL | TYR | CYS | ALA | TRP | VAL |
| Weighted | Average | 1.14 | −0.86 | 0.90 | 0.30 | 0.29 | 0.58 | 0.79 | 1.14 |
| | Stdev | 0.14 | 0.35 | 0.66 | 0.20 | — | 0.19 | 0.30 | 0.11 |
| Unweighted | Average | 1.07 | −0.96 | 0.41 | 0.73 | 0.29 | 0.54 | 0.41 | 1.25 |
| | Stdev | 0.27 | 1.49 | 1.37 | 0.66 | — | 0.47 | 1.05 | 0.17 |
| | Light | 43 | 43 | 43 | 43 | 43 | 43 | 46 | 98 |
| | Consensus | ALA | ALA | ALA | ALA | ALA | ALA | LEU | PHE |
| Weighted | Average | 0.50 | 0.50 | 0.50 | 0.50 | 0.50 | 0.50 | 1.08 | 1.20 |
| | Stdev | 0.33 | 0.33 | 0.33 | 0.33 | 0.33 | 0.33 | 0.09 | 0.03 |
| Unweighted | Average | 0.47 | 0.47 | 0.47 | 0.47 | 0.47 | 0.47 | 0.95 | 1.23 |
| | Stdev | 0.59 | 0.59 | 0.59 | 0.59 | 0.59 | 0.59 | 0.27 | 0.15 |
| | Heavy | 37 | 39 | 89 | 91 | 92 | 93 | 103 | 48 |
| | Light | 43 | 43 | 43 | 43 | 43 | 43 | 46 | 98 |
| | 2 × tyr value | 0.52 | 0.52 | 0.52 | 0.52 | 0.52 | 0.52 | 0.52 | 2.34 |
| | Comb. value[1] | 1.64 | −0.36 | 1.40 | 0.80 | 0.79 | 1.08 | 1.87 | 1.82 |
| Weighted | Difference[2] | 1.12 | 0.88 | 0.88 | 0.28 | 0.27 | 0.56 | 1.35 | 0.13 |
| | Comb. Stdev.[3] | 0.46 | 0.69 | 1.00 | 0.53 | 0.33 | 0.53 | 0.38 | 0.07 |
| | Rating V[4] | 0.42 | 0.78 | 1.13 | 1.89 | 1.24 | 0.97 | 0.28 | 0.06 |
| | 2 × tyr value | 0.52 | 0.52 | 0.52 | 0.52 | 0.52 | 0.52 | 0.52 | 0.52 |
| | Comb. value[1] | 1.54 | −0.49 | 0.88 | 1.20 | 0.76 | 1.01 | 1.35 | 2.48 |
| Unweighted | Difference[2] | 1.02 | 1.01 | 0.36 | 0.68 | 0.24 | 0.49 | 0.83 | 1.96 |
| | Comb. Stdev.[3] | 0.87 | 2.09 | 1.97 | 1.26 | 0.59 | 1.07 | 1.32 | 0.33 |
| | Rating IV[4] | 0.85 | 2.07 | 5.44 | 1.86 | 2.49 | 2.20 | 1.58 | 0.17 |

[1] Sum of the residue pair's average hydrophobicity values
[2] Size of the difference (square root of squared difference) between the sum of the value for two tyrosine residues (0.52) and the sum of the residue pairs' average values ([1])
[3] Sum of both residue's standard deviation
[4] Formula used: Stdev/Difference ([3]/[2])

6.10. Filter 6

Partial Elimination of Pairs with Highly Conserved Residues

All residues under consideration are within the Framework Regions of either the heavy or the light chain of Fv fragments, and can therefore be expected to be conserved. Therefore, for the purpose of this analysis, residues that are more than 80% conserved (see Table 9) are eliminated, with the exception of pairs in which an aromatic amino acid is conserved (see below).

TABLE 9

Residue amino acid identity conservation

| | Consensus[1] | Occurrence of consensus[2] | Sample size, N[3] | No. occurring AAs[4] | AA identity conservation[5] |
|---|---|---|---|---|---|
| Heavy Chain | | | | | |
| 37 | VAL | 31 | 40 | 4 | 78% |
| 39 | GLN | 35 | 37 | 3 | 95% |
| 48 | VAL | 30 | 42 | 4 | 71% |
| 89 | VAL | 25 | 40 | 7 | 63% |
| 91 | TYR | 42 | 44 | 2 | 95% |
| 92 | CYS | 44 | 44 | 1 | 100% |
| 93 | ALA | 37 | 42 | 4 | 88% |
| 103 | TRP | 30 | 33 | 3 | 91% |
| Light Chain | | | | | |
| 43 | ALA | 49 | 65 | 6 | 75% |
| 46 | LEU | 54 | 57 | 3 | 95% |
| 98 | PHE | 66 | 68 | 3 | 97% |

[1] Most frequently occurring amino acid the indicated residue
[2] Number of the consensus amino acid ([1]) occurrences at the indicated residue
[3] Number of amino acids known for an Fv fragment at the indicated residue
[4] Number of different amino acids (AAs) occurring at the indicated residue
[5] Occurrence of the consensus amino acid ([2]) divided by the sample size, N([3]).

Of the residues of the residue pairs of tables 4, 5, 6, 8, and 9, four pairs either do not contain a conserved aromatic amino acid, or do contain a residue that is more than 80% conserved, and are therefore eliminated.

The remaining residue pairs, that are predicted to be the optimal positions for the cross-link, are listed in Table 10 with all ratings described above.

TABLE 10

Selected potential residue pairs for the tyr-tyr cross-link to be directed to.

| Residue pairs (H/L) | Rating I | Rating II | Rating III/IV | Rating V/VI |
|---|---|---|---|---|
| 103/46 | 0.49 | 0.49 | 10.39/1.32 | 0.28/1.58 |
| 89/43 | 0.06 | 1.27 | 0.26/0.64 | 1.13/5.44 |
| 37/43 | 0.26 | 2.10 | 0.21/0.49 | 0.42/0.85 |
| 48/98 | 0.01 | 0.30 | 0.28/0.43 | 0.06/0.17 |

6.11. Residue Pair Selection Flowchart for Software

Database Assembly

Starting Material

2-D Database Import and Sorting of Data
  Sequence Data
  Import of 2D-polypeptide sequence data
    Define:
      s=sample size (number) of sequences of the individual polypeptide chains of the protein complex (preferably in polypeptide pairs of a complexes)
  Alignment of data according to functional conservation (e.g. Kabat & Wu numbering system for Ig)
    Define:
      i (subscript)=amino acid position within the alignment system to which any given atom belongs
  Compilation of identity (three letter code) and frequency of amino acids occurring at each residue
    Define:
      $f_i$=frequency of the occurrence of a particular amino acid at a given residue, i
      $n_i$=number of amino acids occurring at a given residue, i
  Define and mark residues of both polypeptides within the conserved regions of both polypeptides (Framework Regions for Fv fragments)
    Assign:
      con=conserved residues
      non=variable residues
  Assignment of consensus
    Define:
      The consensus is the most frequently occurring amino acid at any given residue of either polypeptide.
    Assign:
      For each residue, i,
      Assign the consensus using, for example, amino acid single-letter code. For residues at which two or more amino acids occur most frequently, assign all most frequently occurring amino acids.
  Data On Physical Properties of Amino Acid Side-Chains
  Compilation of look-up tables with amino acids and corresponding numeric values Numeric values correspond to the most relevant physical properties of amino acid side-chains as they influence the overall structure of polypeptide complexes (e.g. side-chain volume, charge, hydrophobicity, and degrees of rotational freedom, etc.)
    Define:
      p (subscript): amino acid side-chain physical property chosen for the selection process
      $N_{pi}$=numeric value of a physical property corresponding to an occurring amino acid at a given residue, i 3-D Database Import and Sorting of Data
  Sorting by Sequence (2-D)
  Import of 3D-ordinate data of the polypeptides (from the structure of the complex as a whole)
    Define:
      m (subscript)=sample size (number) of different structures file imported (for both polypeptides of a complex)
  Alignment of data according to functional conservation (e.g. Kabat & Wu numbering system for Ig)
  Sorting by Atomic, 3-D Position
  Sorting of coordinate data by amino acid residue and atom position
    Select alpha and beta carbons
    Define:
      $Ca1_i$=alpha carbon belonging to the first of two polypeptides
      $Ca2_i$=alpha carbon belonging to the second of two polypeptides
      $Cb1_i$=beta carbon belonging to the first of two polypeptides
      $C\beta2_i$=beta carbon belonging to the second of two polypeptides
      Coordinates of $Ca1_i$: $x_{A1i}$, $y_{A1i}$, $z_{A1i}$
      Coordinates of $Ca2_i$: $x_{A2i}$, $y_{A2i}$, $z_{A2i}$
      Coordinates of $C\beta1_i$: $x_{B1i}$, $y_{B1i}$, $z_{B1i}$
      Coordinates of $C\beta2_i$: $x_{B2i}$, $y_{B2i}$, $z_{B2i}$
  Assembly of Residue Pairs
  Assembly of all possible inter-chain pairs of residues
    Define
      j (subscript)=pair of amino acids as they fall within the above alignment system of both polypeptide chains
  Compilation of Relevant Measurements; Secondary, Derivative Data
    2-D Derivative Data
    Computation of Residue characteristics for each physical property
    Retrieval of numeric values of each side-chain physical property for each amino acid occurring at each residue
      Match every amino acid identity at each residue in the look-up table, and retrieve corresponding numeric values
    Calculation of weighted statistical measurements for each residue
      Define:
        $w\mu_{pi}$=weighted average of the sample, s, of numeric values of a physical property at each residue, i, weighted by each occurring amino acid s frequency of occurrence, $f_i$
        $w\sigma_{pi}$=weighted standard deviation of the sample, s, of numeric values of a physical property at any residue, i, weighted by each occurring amino acid s frequency of occurrence, $f_i$
      Calculate:
        for the sample of sequences in the database, s, for each residue, h, and for each physical property, p $$w\mu_{pi} = \Sigma(N_{pi} * f_{pi})/\Sigma f_{pi}$$

$$w\acute{o}_{pi} = SQRT((\Sigma_{pi} * \Sigma(f_{p1} * N_{pi}^2) - \Sigma(f_{pi} * N_{pi})^2)/\Sigma f_{pi} * \Sigma(f_{pi}-1))$$

Calculation of un-weighted statistical measurements for each residue
    Define:
      $u\mu_{pi}$=un-weighted average of the sample, s, of numeric values of a physical property at any residue, i, not weighted by each occurring amino acid's frequency of occurrence, $f_i$ $u\sigma_{pi}p$=un-weighted standard deviation of the sample, s, of the numeric values of a physical property at any residue, i, not weighted by each occurring amino acid's frequency of occurrence, $f_i$ Calculate:

for the sample of sequences in the database, s, for each residue, i, and for each physical property, p:

$u\mu_{pi}=(\Sigma n_{pi})/n_i$ $u\sigma_{pi}=SQRT((n_i*\Sigma n_{pi}^2-\Sigma(n_i*N_{pi})^2)/n_i*(n_i-1))$ Calculation of Each Pair's Combined Average and Standard Deviation For both residues of each pair the sum of both average and standard deviation values are calculated for each physical property.

Calculate:

For every residue pair, j:

$w\mu_{pj}=w\mu_{pi}+w\mu_{pi}$ $u\mu_{pj}=u\mu_{pi}+u\mu_{pi}$ $w\sigma_{pj}=w\sigma_{pi}+w\sigma_{pi}$ $u\sigma_{pj}=u\sigma_{pi}+u\sigma_{pi}$ 3-D Derivative Data Calculation of Residue Pari Inter-atomicalphacarbon Distances, $D_\alpha$ Application of Pythagorean geometry to the alpha carbon coordinates of each residue pair, j Calculate:

For every residue pair, j:

$D_{\alpha j}=Sqrt((x_{A1i}-x_{A2i})^2+(y_{a1i}-y_{A2i})^2+(Z_{A1i}-Z_{A2i})^2)$ And for the sample of structures in the database, m $\mu_{\alpha j}$=Average of all $D_{\alpha j}$ $\nu_{\alpha j}$=Median of all $D_{\alpha j}$ $\sigma_{\alpha j}$=Standard deviation of all $D_{\alpha j}$ $Max_{\alpha j}$=Maximum of all $D_{\alpha j}$ $Min_{\alpha j}$=Minimum of all $D_{\alpha j}$ Calculation of Difference Between Residue Pair Alpha— and Beta Carbon Distances, $\Delta_j$ Application of Pythagorean geometry to residue pair beta carbon coordinates, and subtraction Calculate:

For every residue pair, j:

$D_{\beta j}$: formula as described for alpha-carbon distance measurement with beta carbon distance measurement with beta carbon coordinates $x_{B1\ and\ 2}$, $y_{B1\ and\ 2}$, $z_{B1\ and\ 2}$ $\Delta_j=D_{\alpha j}-D_{\beta j}$ And for the sample of structures in the database, m $\mu_{\Delta j}$=Average of all $\Delta_j$ $\nu_{\Delta j}$=Median of m $\Delta_j$ $\sigma_{\Delta j}$=Standard deviation of all $\Delta_j$ $Max_{\Delta j}$=Maximum of all $\Delta_j$ $Min_{\Delta j}$=Minimum of all $\Delta_j$ Calculation of 3D Angles, $\phi_j$ and $\psi_j$ Define:

$\phi_j$=angle described by the atoms (points) $C\beta 1_i$–$C\alpha 1_i$–$C\alpha 2_i$ $\psi_j$=angle described by the points $C\beta 2_i$–$C\alpha 2_i$–$C\alpha 1_i$ $va1_j$=vector from $C\alpha 1_i$ to $C\alpha 2_i$, $va2_j$=vector from $C\alpha 2_i$ to $C\alpha 1_i$, $vb1_j$=vector from $C\alpha 1_i$ to $C\beta 1_i$, $vb2_j$=vector from $C\alpha 2_i$ to $C\beta 2_i$, Calculate:

vector coordinates, for every residue pair, j:

| $va1_j$ | $va2_j$ | $vb1_j$ | $vb2_j$ |
|---|---|---|---|
| $X_{va1j} = x_{A2i} - x_{A1i}$ | $x_{va2j} = x_{A1i} - x_{A2i}$ | $x_{vb1j} = x_{B1i} - x_{A1i}$ | $x_{vb2j} = x_{B1i} - x_{A2i}$ |
| $y_{va1j} = y_{A2i} - y_{A1i}$ | $y_{va2j} = y_{A1i} - y_{A2i}$ | $y_{vb1j} = x_{B1i} - y_{A1i}$ | $y_{vb2j} = y_{B1i} - y_{A2i}$ |
| $z_{va1j} = z_{A2i} - z_{A1i}$ | $z_{va2j} = z_{A1i} - z_{A2i}$ | $z_{vb1j} = x_{B1i} - z_{A1i}$ | $z_{vb2j} = z_{B1i} - z_{A2i}$ |

Calculate:

Angle $\phi_j$ (based on scalar products), for every residue pair, j $$\varphi_j = \arccos\left(\frac{(x_{va1j}*x_{vb1j}+y_{va1j}+*y_{vb1j}z_{vb1j}*z_{vb1j})}{sqrt(x_{va1j}^2+y_{va1j}^2+z_{va1j}^2)*sqrt(x_{vb1j}^2+y_{vb1j}^2+z_{vb1j}^2)}\right)$$

And for the sample of structures in the database, m $\mu_{\phi j}$=Average of all $\phi_j$ $\nu_{\phi j}$=Median of all $\phi_j$ $\sigma_{\phi j}$=Standard deviation of all $\phi_j$ $Max_{\phi j}$=Maximum of all $\phi_j$ $Min_{\phi j}$=Minimum of all $\phi_j$ Calculate:

Angle $\psi_j$ (based on scalar products), for every residue pair, j $$\Psi_j = \arccos\left(\frac{(x_{va2j}*x_{vb2j}+y_{va2j}+*y_{vb2j}z_{vb2j}*z_{vb2j})}{sqrt(x_{va2j}^2+y_{va2j}^2+z_{va2j}^2)*sqrt(x_{vb2j}^2+y_{vb2j}^2+z_{vb2j}^2)}\right)$$

And for the sample of structures in the database, m $\mu_{\psi j}$=Average of all $\psi_j$ $\nu_{\psi j}$=Median of all $\psi_j$ $\sigma_{\psi j}$=Standard deviation of all $\psi_j$ $Max_{\psi j}$=Maximum of all $\psi_j$ $Min_{\psi j}$=Minimum of all $\psi_j$ Calculation of the Third 3D-angle Define:

Vector $g1_j$ ($vg1_j$): $A1_i$-$B2_i$

Plane $E1_j$, described by vectors $va1_j$ and $vb1_j$

Plane $E2_j$, described by vectors $va1_j$ and $vb1_j$

Vector $n1_j(vn1_j)$, perpendicular to $E1_j$, the vector product of $va1_j$ and $vb1_j$ Vector $n2_j(vn2_j)$, perpendicular to $E2_j$, the vector product of $va1_j$ and $vb1_j$ Calculate:
vg1 coordinates, for every residue pair, j

| $vg1_j$ |
|---|
| $x_{vg1j} = x_{B2i} - x_{A1i}$ |
| $y_{vg1j} = y_{B2i} - y_{A1i}$ |
| $z_{vg1j} = z_{B2i} - z_{A1i}$ |

Calculate:
vn1 and vn2 coordinates (vector products), for every residue pair, j
$vn1_j$=vector product of $va1_j$ and $va2_j$
$vn2_j$=vector product of $va1_j$ and $vg1_j$

| $vn1_j$ | $vn2_j$ |
|---|---|
| $x_{vn2j} = y_{va1j} * z_{vb1j} - y_{vb1j} * z_{vb1j}$ | $x_{vn2j} = y_{va1j} * z_{vb1j} - y_{vb1j} * z_{vb1j}$ |
| $y_{vn2j} = z_{va1j} * x_{vb1j} - z_{vb1j} * x_{vb1j}$ | $y_{vn2j} = z_{va1j} * x_{vb1j} - z_{vb1j} * x_{vb1j}$ |
| $z_{vn2j} = x_{va1j} * y_{vb1j} - x_{vb1j} * y_{vb1j}$ | $z_{vn2j} = x_{va1j} * y_{vb1j} - x_{vb1j} * y_{vb1j}$ |

Calculate:
Angle between $vn1_j$ and $vn2_j$, angle $\chi_j$, for every residue pair, j $$\chi_j = \arccos\left(\frac{(x_{vn1j}*x_{vn2j} + y_{vn1j}*y_{vn2j} + z_{vn1j}*z_{vn2j})}{Sqrt(x_{vn1j}^2 + y_{vn1j}^2 + z_{vn1j}^2) * sqrt(x_{vn2j}^2 + y_{vn2j}^2 + z_{vn2j}^2)}\right)$$

And for the sample of structures in the database, m
$\mu_{\chi j}$=Average of all $\chi_j$
$\nu_{\chi j}$=Average of all $\chi_j$
$\sigma_{\chi j}$=Standard deviation of all $\chi_j$
$Max_{\chi j}$=Maximum of all $\chi_j$
$Min_{\chi j}$=Minimum of all $\chi_j$ Compilation of Residue Pair Ratings; Tertiary, Derivative Data Residue Pair Ratings Based on 2-D Database For each Physical Property Chosen for the Selection Process
Define:
$T_p$=sum of the numeric values of the physical properties of the amino acids to be substituted with in both polypeptide chains (2× value of tyrosine for the tyrosine oxidative cross-link)

$v_p$=allowable multiples of the weighted and un-weighted standard deviations of a physical property's values, $u\sigma_{pj}$.

Rating (R) based on numeric values of a physical property, p, corresponding to occurring amino acids, weighted by the frequency of each amino acid's occurrence.
Calculate:
For each residue pair, j $$wR_{pj}=v_p*w\sigma_{pj}/(abs(T_p-w\mu_{pj}-v_p*w\sigma_{pj}))$$

Rating based numeric values of a physical property, p, corresponding to occurring amino acids.

Calculate:
For each residue pair, j $$uR_{pj}=v_p*u\sigma_{pj}/(abs(T_p-u\mu_{pj}-v_p*u\sigma_{pj}))$$

Residue Pair Ratings Based on 3-D Database
Alpha Carbon Spacing
Define:
$v_{R\alpha}$ allowable multiples of the standard deviation of inter-chain alpha carbon distances, $\sigma_{\alpha j}$
$vMax_\alpha$: maximal value allowable for $\mu_{\alpha j}$ in the selection process
$vMin_\alpha$: minimal value allowable for $\mu_{\alpha j}$ in the selection process
$T_\alpha$: Target value for alpha carbon spacing
$R_{\alpha j}$: Rating based on inter-chain alpha carbon spacing, scores high for residue pairs, j, with $\mu_{\alpha j}$ values close to the target value, $T_\alpha$, and/or with high $\sigma_{\alpha j}$ values (flexibility)

Calculate:
$T_\alpha$=average of $vMax_\alpha$ and $vMin_\alpha$
For all residue pairs, j

| For all $\mu_{\alpha j} < T_\alpha$: | For all $\mu_{\alpha j} < T_\alpha$: |
|---|---|
| $R_{\alpha j} = (T_\alpha - \mu_{\alpha j} + v_{r\alpha} * \sigma_{\alpha j})^2/\sigma_{\alpha j}$ | $R_{\alpha j} = (\mu_{\alpha j} + v_{r\alpha} * \sigma_{\alpha j} - T_\alpha)^2/\sigma_{\alpha j}$ |

Φ and ψ Angles
Define:
$V_{R\phi\psi}$: allowable multiples of the standard deviation of $\phi_j$ and $\psi_j$ angles, $\sigma_{\phi j}$ and $\sigma_{\psi j}$
$vMax_{\phi,\psi}$: maximal value allowable for $\mu_{\alpha j}$ in the selection process (same value for both angles)
$vMax_{\phi,\psi}$: minimal value allowable for $\mu_{\alpha j}$ in the selection process (same value for both angles)
$T_{\phi\psi}$: Target value of φ and ψ angles (same value for both angles)
$R_{\phi,\psi j}$: Rating based on the angles φ and ψ; scores high for residue pairs, j, with $\mu_{\phi j}$ and $\mu_{\phi j}$ values close to the target value, $T_{\phi,\psi}$, and/or with high $\sigma_{\phi j}$ and $\sigma_{\psi j}$ values (flexibility)
$r_\phi$: sub-rating based on the angle φ
$r_\psi$: sub-rating based on the angle ψ

Calculate:
$T_{\phi,\psi}$=average of $vMax_{\phi,\psi}$ and $vMin_{\phi,\psi}$
For every residue pair, j

| For all $\mu_{\phi j} < T_{\phi,\psi}$: | For all $\mu_{\alpha j} < T_{100,\psi}$: |
|---|---|
| $r_{\phi j} = (T_{\phi,\psi} - \mu_{\phi j} + v_{r\phi,\psi} * \sigma_{\phi j})^2/\sigma_{\phi j}$ | $r_{\phi j} = (\mu_{\phi,\psi} + V_{R\phi,\psi} * \sigma_{\phi j} - T_{\phi,\psi})^2/\sigma_{\phi j}$ |
| $r_{\phi j} = (T_{\phi,\psi} - \mu_{\phi j} + v_{R\phi,\psi} * \sigma_{\psi j})^2/\sigma_{\psi j}$ | $r_{\psi j} = (\mu_{\phi,\psi} + V_{R\phi,\psi} * \sigma_{\psi j} - T_{\phi,\psi})^2/\sigma_{\psi j}$ |
| $R_{\phi,\psi j}$ = average of $r_{\phi j}$ and $r_{\psi j}$ | |

Difference Between Alpha- and Beta Carbon Spacing
Define:
$v_{RA}$: allowable multiples of the standard deviation for each residue pair, j, of m differences between inter-chain alpha- and beta carbon distances, $\sigma_{Aj}$
$vMax_A$: maximal value allowable for $\mu_{Aj}$ in the selection process
$vMin_A$: minimal value allowable for $\mu_{Aj}$ in the selection process $T_A$: Target value for the difference between alpha beta carbon spacing $R_{Aj}$: Rating based on differences between inter-chain alpha- and beta carbon distances, scores high for residue pairs, j, with $\mu_{Aj}$ values close to the target value, $T_{Aj}$, and/or with high $\sigma_{Aj}$ values (flexibility)

Calculate:

$T_A$ = average of vMax$_A$ and vMin$_A$

For all residue pairs, j

| For all $\mu A_j < TA$ | For all $\mu A_j > TA$ |
|---|---|
| $R_{Aj} = (T_A - \mu_{Aj} + v_{RA} * \sigma_{Aj})^2/\sigma_{Aj}$ | $R_{Aj} = (\mu_{Aj} + v_{RA} + *\sigma_{Aj} - T_A)^2/\sigma_{Aj}$ |

Selection Processes

The sequence of filters is of no significance

I 2D Selection Processes

Filter I.1: Selection for Conserved Residues

For all residue pairs

If the amino acids of residue pair J are both assigned mark 'con' (conserved), select If either amino acid of a residue pair j is assigned 'non' (variable), discard Filter I.2: Selection Against Residues that have Glycine as Consensus Selection of Pairs of which neither residue is most frequently glycine, for all residue pairs:

If the consensus (most frequently occurring amino acid) of neither residue of a pair j is glycine, select If the consensus (most frequently occurring amino acid) of either residue of a pair j is glycine, discard Filter I.3: Selection Based on Weighted Statistical Measurements Selection using statistical measurements of a physical property, p, of occurring amino acids at each residue, i, of every residue pair, j, weighted by the occurring amino acid's frequency of occurrence Define:

Max$_{wRp}$: maximum limit for the selection of an amino acid side-chain physical property, p, based on weighted statistical measurements Min$_{wRp}$: minimum limit for the selection of an amino acid side-chain physical property, p, based on weighted statistical measurements Calculate:

IF [Min$_{wRp}$<wR$_{pj}$<Max$_{wRp}$] is True, select

IF [Min$_{wRp}$<wR$_{pj}$<Max$_{wRp}$] is False, discard

Filter I.4: Selection Based on Un-weighted Statistical Measurements

Selection using statistical measurements of a physical property, p, of occurring amino acids at each residue, i, of every pair, j, not weighted by the occurring amino acid's frequency of occurrence Define:

Max$_{uRp}$: maximum limit for the selection of an amino acid side-chain physical property, p, based on weighted statistical measurements Min$_{uRp}$: minimum limit for the selection of an amino acid side-chain physical property, p, based on weighted statistical measurements Calculate:

IF [Min$_{uRp}$<uR$_{pj}$<Max$_{uRp}$] is True, select

IF [Min$_{uRp}$<uR$_{pj}$<Max$_{uRp}$] is False, discard

II 3D Selection Process

Filter II.1: Selection for Average Alpha-carbon Distances within Selection Range Calculation:

For all residue pairs:

IF [vMin$_\alpha$<$\mu_{\alpha j}$<vMax$_\alpha$] is True, select

IF [vMin$_\alpha$<$\mu_{\alpha j}$<vMax$_\alpha$] is False, discard

Filter II.2: Selection for Sufficient Flexibility of Alpha Carbon Spacing

Calculation:

For all residue pairs:

For all $\mu_{\alpha j} < T_\alpha$

IF [$\mu_{\alpha j}+v_{R\alpha}*\sigma_{\alpha jm}>T_\alpha$]=True, select

IF [$\mu_{\alpha j}+v_{R\alpha}*\sigma_{\alpha jm}>T_\alpha$]=False, discard

For all $\mu_\alpha > T_\alpha$

IF [$\mu_{\alpha j}-v_{R\alpha}*\sigma_{\alpha j}<T_\alpha$]=True, select

IF [$\mu_{\alpha j}+v_{R\alpha}*\sigma_{\alpha j}<T_\alpha$]=False, discard

Filter II.3: Selection for Pairs with $\Phi$ and $\psi$ Angles within the Selection Range Calculation:

IF [vMin$_{\phi,\psi}$<$\mu_{\phi j}$<vMax$_{\phi,\psi}$] AND [vMin$_{\phi,\psi}$<$\mu_{\psi j}$<vMax$_{\phi,\psi}$] is True, select IF [vMin$_{\phi,\psi}$<$\mu_{\phi j}$<vMax$_{\phi,\psi}$] AND [vMin$_{\phi,\psi}$<$\mu_{\psi j}$<vMax$_{\phi,\psi}$] is False, discard Filter II.4: Selection for Average Differences Between Alpha- and Beta Carbon Distances within Selection Range $\mu_{Aj}$=average difference between residue alpha carbon and beta carbon distances Calculation:

For all residue pairs

IF [vMin$_A$<$\mu_{Aj}$<vMax$_A$] is True, select

IF [vMin$_A$<$\mu_{Aj}$<vMax$_A$] is False, discard

Filter II.5: Selection for Sufficient Flexibility of the Pairs' Difference Between Alpha and Beta Carbon Distances Calculation:

For all residue pairs:

For all $\mu_{Aj} < T_A$

IF [$\mu_{Aj}+v_{RA}*\sigma_{Aj}>T_A$]=True, select

IF [$\mu_{Aj}+v_{RA}*\sigma_{Aj}>T_A$]=False, discard

For all $\mu_\alpha > T_A$

IF [$\mu_{Aj}-v_{RA}*\sigma_{Aj}>T_A$]=True, select

IF [$\mu_{Aj}-v_{RA}*\sigma_{Aj}>T_A$]=False, discard

Final Selection

Selected Amino Acid Pairs

All residue pairs, j, that are selected in all Filters (I.1–4 and II.1–6) are compiled and listed.

Sort and Select by Ratings

All listed residue pairs are compared by their Ratings, and the pair with the highest Ratings is the FINAL SELECTION.

6.12. Point Mutagenesis and Sub-Cloning into Expression Vectors

6.12.1. Conservative Substitutions for Undesired Tyrosine Residues cDNA fragments encoding the Fv fragment heavy and light chains of the monoclonal anti-α5-integrin antibody (example 1), or the monoclonal anti-β1-integrin antibody (example 2) are isolated from the hybridomas that produce them according to standard procedures known in the art. For example, RNA is isolated from the pellet of a suspension culture of hybridoma cells, the RNA is reversed transcribed using a mixture of poly-A and random primers, and cDNAs of the heavy and light chains are isolated by the RACE method. The sequences of the heavy and light chains, that are to be cross-linked according to the procedures of the instant invention, are identified by standard procedures, and aligned with the K&W numbering system. Tyrosine residues identified are examined for their predicted proximity and positional flexibility toward each other. Residue pairs at which reactive side chains are found in the sequence that are either within an average of 15 Å or less in the sample, or that have an average and standard deviation, such that the average less one standard deviation is 15 Å or less in the sample are identified. Of these pairs, the residue of the pair at which tyrosine occurs at the lowest frequency in the 2-D Database, is point mutated to phenylalanine. Point mutations are introduced by using the QuikChange™ Site-Directed Mutagenesis Kit (Stratagene, Catalog # 200518).

6.12.2. Substitution of Residues of a Selected Pair with Tyrosine

At the residues of the pair selected, as described above, amino acid substitutions are introduced by point mutation, so far as tyrosine is not already present at the selected residues of the pair in the sequences of the heavy and light chains of the Fv fragment to be stabilized. Point mutations are introduced by using the QuikChange™ Site-Directed Mutagenesis Kit (see above).

6.12.3. Expression Vector and System

DNA fragments encoding the Fv fragment heavy and light chains, all containing the conservative amino acid substitutions for undesired tyrosine residues, identified as described above, with and without the amino acid substitutions of residues of the selected pair with tyrosine are isolated. The isolated fragments (inserts) are subcloned into a pGEX expression vector containing the TEV-protease cleavage site. For the purposes of measuring the Fv fragments retained affinity for its antigen, the insert encoding the heavy chain is also fused with a nucleotide sequence encoding a Hemaglutinin (HA)-tag at the 3' end (C-terminus of the protein), for which a secondary antibody is commercially available. For the purposes of using the Fv fragment in diagnostic, therapeutic, or any other commercial applications, however, the HA-tag should be removed again. Subcloning is carried out by standard procedures known in the art.

6.13. Fv Fragment Bacterial Expression and Purification

The above-described expression plasmids encoding modified heavy and light Fv fragments are transformed competent BL21 or XA90 bacteria. Frozen glycerol stocks (0.5 ml) are prepared from individual ampicillin resistant clones, with which expression cultures (e.g. 1000 ml Luria Broth: 10 gm tryptone, 5 gm yeast extract, 5 gm NaCl) containing 100 µg/ml ampicillin) are inoculated. The cells are grown at 30° C. on a rotary shaker (300 rpm), and protein expression is induced with 1 mM IPTG at an OD600 of 0.6. Following a three hour incubation, bacteria are harvested by centrifugation at 4000 g at 4° C. The pellet is resuspended with ice-cold 50 ml Lysis Buffer (20 mM Tris.Cl pH 7.9, 500 mM NaCl, 10% glycerol, 20 mM β-mercaptoethanol, 1 mM PMSF, 20, g/ml leupeptin, 20 µg/ml pepstatin, 1% aprotinin) and then sonicated on ice until lysis is >90% complete. Insoluble matter is removed by centrifugation at 20,000 g at 4° C. for 20min. The supernatant is then incubated with 2 ml Glutathione sepharose (Pharmacia) for 2 hrs at 4° C. The beads are then pelletted by centrifugation at 4000 g, and washed (re-suspended and pelletted) twice in 10 ml Lysis Buffer and twice in 10 ml TEV-protease Cleavage Buffer (Novagen). The beads are then incubated with 1 µg His-tagged TEV protease (Novagen) at 30° C. for 1 hr in 2 ml Cleavage Buffer. The protease is subsequently removed by adding 0.1 ml equilibrated NTA-agarose (Qiagen) slurry to the suspension. Partially purified FvH and FvL fragments are present in the supernatant following centrifugation at 4000 g.

6.14. Introduction of the Oxidative Tyrosyl-Tyrosyl Cross-Link

The Fv fragment heavy and light chain gene products containing only the mutations of undesired reactive tyrosine residues to phenylalanine, without the mutations of the selected residue pair to tyrosine are partially purified and equilibrated by dialysis in phosphate buffered saline (PBS) before mixing them at equal molarity (0.1–1000 µM). The catalyst, metalloporphyrin 20-tetrakis (4-sulfonateophenyl)-21H,23H-porphine manganese (III) chloride (MnTPPS) is then added on ice to a concentration of 1 µM, 5 µM, 10 µM, 50 µM and 100 µM to the reaction. The reaction is then initiated by the addition of the oxidant potassium monopersulfate to a concentration of 1–100 µM, at room temperature or otherwise, for each of the concentrations of the catalyst, and at several protein concentrations. After 45 seconds the reaction is quenched by the addition of Tris.Cl pH7.9 to 50 mM and β-mercaptoethanol to 10 mM, and the solution is again dialyzed against PBS to remove the catalyst, oxidizing and reducing agents. Cross-linked and not cross-linked hetero-dimers and monomers are isolated by gelfiltration FPLC. The efficiency of the cross-link reaction is tested by non-reducing PAGE and Coomassie blue staining.

At each protein concentration, the maximal concentration of oxidizing reagent and catalyst at which a cross-link between the polypeptides of the reaction does not form is noted. These conditions are used to catalyze the reaction between the Fv fragment heavy and light chain gene products containing both the mutations of undesired reactive tyrosine residues to phenylalanine, and the mutations of the selected residue pair to tyrosine. Cross-linked and not cross-linked hetero-dimers and monomers are isolated by gelfiltration FPLC. The efficiency of the cross-link reaction is tested by non-reducing PAGE and Coomassie blue staining.

6.15. Testing the Stabilized Complex 6.15.1. Yield of Functionally Stabilized Fv Fragment Complex Yield of functionally cross-linked Fv fragments is tested by passing a carefully determined amount of cross-linked, and glycerol gradient-purified Fv fragment protein over an immobilized antigen column, and comparing the flow-through with the starting material and the eluate of the column. Protein concentration measurements are carried out by standard procedures, such as Bradford or Lowrie assays (Bradford, 1976, and Lowrie, 1954), Coomassie-or silverstaining, or Western blotting.

6.15.2. Retained Affinity

Fv fragments that are successfully cross-linked under the various conditions described above are tested for their retained affinity in ELISA-type procedures. Using 96 well-plates, the inside surfaces of the ELISA-assay plate wells are coated with antigen, for example integrin α5 (Example 1)

and integrin β1 (Example 2). The wells are washed, and with respect to one another, half the concentration of the full length antibody and an equal molar concentration of the F(ab) fragment of the antibody (see below) as positive controls, and the Fv fragment of the antibody, cross-linked as described above, are incubated in PBS for two hours at 37° C. in serial dilutions in the wells coated with the respective antigen on one plate. F(ab) fragments are derived by pepsin digestion of the full length antibody and subsequent purification first by removal of the Fc fragments by running the antibody/protease solution through a Protein A column, and second by fractionating the flow-through of the Protein A column by ion exchange FPLC to remove the protease. The wells are washed four times with 200 µl of PBS and the anti-HA tag and alkaline phosphatase-coupled secondary antibody are sequentially incubated in PBS for an additional hour at 37° C. Wells are washed again four times with 200 µl of PBS. The concentrations of bound IgG, F(ab) fragment, and Fv fragment are determined by standard procedures with an ELISA assay reader.

6.15.3. Stability in Serum, Lysate, and the Cyytoplasm

Stability of the complex in serum is tested in time-course experiments by incubating the complex in human serum at 37° C., 38° C., 39° C., 40° C., 42° C., and 45° C. for up to two weeks, and testing for the remaining levels of functional Fv fragment complexes. As controls, the stability of Fab, scFv's and/or dsFv's are compared, all tagged with the same marker.

Stability of the complex in the cytoplasm is tested, also in time-course experiments, analogously to the incubation in serum, by incubating the complex in cell-lysates. More directly, the stability of the complex in the cytoplasm is tested by scrape-loading tissue culture cells with stabilized Fv fragments and assaying for the remaining levels of functional complexes. As controls, the stability of scFv's and dsFv's of the same original immunoglobulin molecule, both tagged with the same marker as the cross-linked Fv fragment, are compared.

In all of these experiments, the remaining levels of functional complexes will be determined in ELISA assays with the same secondary antibody, as described above.

6.15.4. Immunogenicity

Mice are injected with various doses, ranging from 1 µg to 10 mg, of stabilized complex. Stabilized complex is injected in the presence and absence of Freunds (Complete) Adjuvant. Further injections are given to the mice as boosts every five days (in the presence and absence of Incomplete Adjuvant. The mice receive a total of three or four boost-immunizations.

Tail-vein blood samples are taken before each injection, and one week after the final boost. Blood samples are spun at 3000 g for 30 min. at 4° C.

ELISA plates are coated with the stabilized complex and a mixture of the unstabilized Fv fragment heavy and light chains, and ELISA assays are performed according to standard procedures, using a labeled anti-mouse secondary antibody.

The immunogenicity of complexes stabilized by the methods of the instant invention are compared to dsFv's and scFv's constructs of the same original immunoglobulin molecule as controls.

6.15.5. Biodistribution $^{18}$F radiolabeled stabilized Fv fragments, labeled according to the procedures published by Lang L. and Eckelmann U., 1994, are injected into mice. Each mouse is injected with 3 µg of roughly 4.5 MBq/µg of Fv fragment complex. Injected animals are sacrificed at 15, 45, 90, 360 min. and 24 h. and immediately exsanguinated by cardiac puncture. Tissues are separated, dried and weighed on an analytical balance, and counted in a gamma-radiation counter using a high energy setting (for $^{18}$F). Aliquots of blood are also dried and counted. Counts are corrected for decay. Tissue:blood ratios, and the percentage of injected dose per gram tissue are calculated for each tissue.

Early-phase blood clearance studies are performed in mice injected with the same amount of above described $^{18}$F radio-labeled stabilized Fv fragments. Serial tail-vein blood samples are taken at 1, 2, 5, 10, 15, and 30 min. The samples are dried and counted as described above, and the half-life of the Fv fragments in blood is calculated according to standard procedures (Choi C. W. et al. Cancer Research; vol. 55: pp. 5323–5329, 1995).

As controls for the above studies, single chain and disulfide Fv fragment constructs of the same original immunoglobulin molecule are compared.

7. EXAMPLE II

*Candida antarctica* Lipase B (CALB)

The following example illustrates certain variations of the methods of the invention for protein and protein complex stabilization. This example is presented by way of illustration and not by way of limitation to the scope of the invention.

Introduction

Several polypeptides with significant commercial value have been identified in recent years, and furthermore, for many of these polypeptides structural data is available. In the following section, methods of stabilizing one polypeptide, a biocatalyst, for which data is available only for the polypeptide itself, but not for other, structurally related polypeptides. Specifically, described below are the residue pair selection process, introduction of point mutations, expression of the polypeptides and their purification and deglycosylation, the cross-link reaction itself, and analysis of the resulting stabilized biocatalyst; for the description of the adjustment of the cross-link reaction conditions, refer to Chapter 6. Furthermore, a description of the combination of the dityrosine stabilization technology with a complementary technology, a directed evolution approach, is described.

The biocatalyst stabilized in the below example is the lipase B of *Candida antarctica* ("CALB", FIGS. 1C, 15A), an enzyme for which multiple commercially relevant applications are possible due to its exquisite enantioselectivity, of which some are still uneconomic due to its lack of stability under adverse reaction conditions.

The structure file 1 LBS containing the three dimensional atomic coordinates of the polypeptide's crystal structure is obtained from the Brookhaven National Laboratory Protein Database. The derivative data relevant to the selection process is calculated as described. The selection process is carried out using a set of filters that is convenient and appropriate for this application of the instant invention.

Point mutations to tyrosine (directing the cross-link reaction) are introduced according to the final selection of the selection process, as described. The polypeptide is expressed in *Pichia pastoris* as a yeast alpha factor fusion protein, which directs the secretion of the fusion protein. The protein is affinity purified by its C-terminal His(6) tag, using NTA column.

The minimally required reaction conditions are adjusted as described in Chapter 6. The cross-link efficiency of the reaction is tested, and the resulting, stabilized biocatalyst is then tested for retained activity and specificity, and for improved stability in time, and under adverse conditions.

Advantages of the Tyrosyl-Tyrosyl Cross-Link for Biocatalysts

The underlying chemistry of the technology covered by the present invention causes an oxidative cross-link to form between reactive side-chains of polypeptides that form stable complexes. The dityrosine bond is stable under a broad range of pH and redox conditions. The cross-link reaction requires close proximity between the reactive side-chains that will cross-link.

Thus, the current invention describes a new technology that allows stabilization of biocatalysts and enables their use in a broader range of industrial applications. This technology is designed to improve on preceding, and complement compatible, technologies.

The resultant stabilized biocatalysts will have the following characteristics:

1. The enzymes will be more stable under a broad range of reaction conditions, including, but not limited to, temperature, pH, pressure, salinity, or concentration of other compounds in the reaction, such as a reducing agent, which is often a component of the chemical reaction for which the catalyst is required.

2. The resultant cross-linked and stabilized biocatalyst will retain its activity and specificity due to the specificity of the cross-link reaction and to the selection process.

This stabilization technology is well suited for the development of new products with novel applications, the improvement of existing industrial biocatalysts, and the complementation of existing technologies for the development of novel biocatalysts.

Biocatalyst Applications

Biocatalytic enzymes constitute the preferred class of catalysts for industrial processes due to their high specificity and turnover rates, and their low development costs and cycle times. However, their utility is limited by the relative instability and limited shelf-life of protein molecules that is exacerbated under adverse reaction and/or storage conditions. The technology of this invention that can be applied to stabilize biocatalysts, thereby enhancing their utility and broadening their commercial application.

Application of the instant invention stabilizes enzymes with specifically placed internal cross-links, and thereby increases the stability of enzymes without impairing their activity in the desired reaction conditions. The resulting increase in enzyme stability thus not only addresses shelf-life limitations but also increases the enzymes' reaction rates and process yields.

Industrial biocatalytic processes are used in many industry sectors, including the chemical, detergent, pharmaceutical, agricultural, food, cosmetics, textile, materials-processing, and paper industries. Within these industries, biocatalysts have many applications, ranging from product synthesis (e.g. amino acid manufacturing, and fine chemical synthesis of small-molecule pharmaceuticals) through use as active agents in products (for example, in biological washing powders) to use in diagnostic testing equipment. Biocatalysts also have industrial applications that range from wastewater and agricultural soil treatment, to crude oil refinement (e.g. desulfurication).

Thus, the example of an application of the instant invention described below focuses on a problem of wide relevance, and promises to contribute significantly to the US scientific and technical knowledge base.

Selection of Optimal Residues for Tyrosyl-Tyrosyl Cross-Link

The selection process consisted of a series of tests or 'filters' aimed at successively narrowing down the residue pairs most likely to result in a cross-linked tyrosine pair that minimally alter the activity or specificity of the enzyme, while lending maximal stability.

Data used for the Analysis

Coordinate data for distance calculations of all atoms other than hydrogens of CALB was downloaded from the protein structure database Brookhaven National Laboratory (FIG. 5). These data provide the three-dimensional coordinates (x, y, and z) for each atom in the solved structure, expressed in metric units, i.e. Angströms ($10^{-10}$ m, Å). These data also contains the amino acid sequence of the polypeptide. With this data it was possible to calculate the three-dimensional distances between any desired atoms (e.g., alpha and beta carbon atoms).

Selection Methodology

Optimal residues, to which the cross-link reaction is directed, were selected by a series of filters based on the measurements of values in a database compiled for the purposes of this selection. This database contains numeric measurements of (1) alpha carbon spacing, (2) beta carbon spacing and the difference between the alpha and beta distances, and (3) residue amino acid usage (see below).

FILTER 1: SELECTION OF SUFFICIENTLY-SPACED AROMATIC RESIDUES

Because there are a significant number of aromatic residues available in the sequence of CALB, and because mutation of an aromatic residue (other than tyrosine, i.e. tryptophane, phenylalanine, or histidine) to tyrosine would be maximally conservative, for the selection process of this example, only aromatic residue pairs were analyzed. Furthermore, to maximize the degree to which application of the instant invention stabilizes the enzyme, only pairs that are spaced more than 40 amino acids apart in the two-dimensional amino acid sequence are selected.

TABLE 11

Aromatic residue pairs with alpha carbon distances within the range of 5.70Å to 9.74Å, space more than 20 residues apart.

| CALB residue pair | | Alpha carbon distance | Cα–Cβ Distance Difference |
|---|---|---|---|
| Phe9 | Tyr82 | 9.29 | −0.20 |
| Phe48 | Trp104 | 8.85 | 1.53 |
| Trp52 | Tyr234 | 8.71 | 0.02 |
| Phe131 | Tyr183 | 6.19 | −1.31 |
| Trp104 | His224 | 9.33 | 0.33 |
| Tyr135 | Tyr203 | 7.58 | 0.10 |
| Tyr183 | His224 | 8.20 | −1.09 |
| Phe117 | Tyr300 | 7.7 | 2.07 |

FILTER 2: IDENTIFICATION OF APPROPRIATELY-SPACED RESIDUE PAIRS

To find residue pairs spaced appropriately for a tyrosyl-tyrosyl bond, the alpha carbon to alpha carbon distance between every residue pair in the polypeptide was calculated in a 3D database. This calculation was performed by applying Pythagorean geometry to the 3D coordinates of the alpha carbons (FIG. 6). Based on the calculations above, as a second cut, all residue pairs were selected whose alpha carbons are spaced within the selection range.

Because of the lack of statistical measurements that give insight to positional flexibility, the selection range was reduced by 2 Å, but only on the upper limit.

The range that was selected for was the following:

Min 5.70 Å, Max 9.74 Å.

FILTER 3: SIDE-CHAIN ORIENTATION

In the space that the heavy and light chains occupy, the tyrosine side chains should be oriented toward each other for a cross-link to form with minimal structural distortion. The difference between the alpha carbon distance (i.e. the backbone carbon distance; FIG. 6) and the beta carbon distance (i.e. the distance between the first carbons in each side chain; FIG. 8) of each residue pair was calculated as a proxy, i.e. an estimate of the orientation of the side chains relative to each other (FIG. 9).

The range that was selected for was the following:

Min −2 Å, Max 3.0 Å.

Again, based on 3D coordinate geometry, for each residue pair, the distance between the beta carbons was calculated (FIG. 8). The beta distance was then subtracted from the alpha distance of the residue pair (FIG. 9). This filter was based on whether the difference in the alpha and beta distances of a residue pair falls within the estimated optimal range. In this example, all of the residue pairs in Table 11 met this criterion.

FILTER: PARTIAL ELIMINATION OF PAIRS WITH RESIDUES IN PROXIMITY TO THE ACTIVE SITE OF THE ENZYME

The functionality of an enzyme as a biocatalyst lies in its ability to catalyze chemical reaction. The activity and selectivity of a catalyst is most sensitive at those sites where the catalyst and the reactants physically contact each other. Therefore, mutations and/or cross-links are least desirable in the active site, and residues in or proximal to the active site are excluded.

His224 is in the active site, and is therefore excluded. Because Tyr183 is in close proximity to His224, the selected residues below should be mutated to generate polypeptides with tyrosine pairs, with and without the mutation of Tyr183 to Phe183. Furthermore, because His224 is also in close proximity to Trp104, and because Trp104 is in close proximity to Phe48, residue pairs containing the above residues are also excluded. The remaining residue pairs are list in Table 12 below.

TABLE 12

List of remaining residue pairs with relevant distance measurements.

| CALB residue pair | | Alpha carbon distance | Cα–Cβ Distance Difference | Epsilon carbon distance* |
|---|---|---|---|---|
| Phe117 | Tyr300 | 7.7 | 2.07 | 4.59 |
| Trp52 | Tyr234 | 8.71 | 0.02 | 7.00 |
| Tyr135 | Tyr203 | 7.58 | 0.10 | 9.08 |
| Phe9 | Tyr82 | 9.29 | −0.20 | 9.31 |

*In Trp52, Epsilon Ni is used.

Analysis of Epsilon Carbon Distances

Because the most likely isomer of the di-tyrosine bond is thought to be the epsilon-epsilon bond, and because coordinate data for an epsilon position atom of all of the amino acids selected is available, the distances between the epsilon positions of the above selected residue pairs in Table 12 were analyzed.

The pairs in Table 12 are ranked according to their epsilon carbon distances. However, since in three of the four pairs a point-mutation is required to generate a tyrosine pair, these distances may be altered, and all of the pairs are generated and examined.

Generating Proteins Containing the Selected Point Mutations Vector Construction of pPal-CALB The *C. antarctica* lipase B gene (plasmid pMT1335) is isolated by polymerase chain reaction (PCR) omitting the pre-propeptide sequence according to standard procedures known in the art, using the plasmid pMT1335 (Patkar et al. Chem.& Phys. Of Lipids, 1998. Vol. 93, pp. 95–101) as a template. The lipase gene is amplified using the primers A and B (see FIG. 15B) for the introduction of an EcoRI (and a His(6)-tag) and a NotI site at the 5'- and 3'-end, respectively. The PCR product and the vector pPICzalphaA (Invitrogen) are digested with the restriction enzymes EcoRi and NotI, and gel purified, using the kit QiaexII Gel extraction Kit (Qiagen, 2001 catalog # 20021) according to the manufacturer's protocol. The insert is ligated into the vector, resulting in a fusion between the yeast alpha-factor secretion signal peptide (sequence contained in pPICzalphaA) and CALB, and the resulting plasmid construct, pPal-CALB, is transformed by standard methods known in the art into competent HB101 cells (*E. coli*). The transformants are selected on LB-Amp agar plates. The CALB gene is sequenced by standard methods known in the art.

Point Mutagenesis

At the residues of the pair selected, as described above, amino acid substitutions are introduced by point mutation, so far as tyrosine is not already present at the selected residues, using forward primer for M1 together with Primer B, and forward and reverse primers for M2 and M3, as described in FIG. 15B. Point mutations are introduced by using the QuikChange™ Site-Directed Mutagenesis Kit (see above).

Protein Expression and Purification

Protein expression and purification are carried out according to an adapted method published by Rotticci-Mulder et al. The yeast strain *P. pastoris* SMD1168 (his4, pep4) (Invitrogen) is used for the expression of CALB (Schmidt-Dannert. Bioorg. & Med. Chem., 1999. Vol. 7, pp. 2123–2130; Rotticci-Mulder et al. Prot. Expr. & Purif. 2001. Vol. 21, pp. 386–392.). Cells are made competent and transformed by standard methods known in the art, and transformants are selected on RD His⁻ agar plates (186 g sorbitol, 20 g agar, 20 g dextrose, 13.4 g yeast nitrogen base, 0.2 mg biotin, 50 mg amino acid mix without histidine per liter). *P. pastoris* is grown in YPD medium (10 g yeast extract, 20 g peptone, 20 g dextrose per liter) or BMGY medium (10 g yeast extract, 20 g peptone, 13.4 g yeast nitrogen base, 0.4 mg biotin, 10 mL glycerol, and 100 mL 1 M $K_2HPO_4/KH_2PO_4$, pH 6.0 per liter). Protein expression under the control of the AOX1 methanol-inducible promoter is induced by growing the culture in BMMY medium (10 g yeast extract, 20 g peptone, 13.4 g yeast nitrogen base, 0.4 mg biotin, 5 mL methanol, and 100 mL of a 1 M $K_2HPO_4/KH_2PO_4$ solution, pH 6.0 per liter).

Five-hundred milliliters of BMGY in a 5000-mL E-flask are inoculated with 1 mL of an overnight yeast culture in YPD and grown overnight at 28° C., 300 rpm. The medium is changed for 500 mL BMMY to induce for lipase expression. Methanol is added to the culture medium to a final concentration of 0.5% (v/v) every 24 h for the following 3 days. The sample is collected by separating the culture medium from the cells by centrifugation.

Aliquots of the sample are taken and concentrated according to standard procedures known in the art. The concentrated sample is separated by SDS-PAGE on a 12% polyacrylamide gel, and analyzed by Coomassie Blue and silver staining.

The protein is bound to NTA column (Qiagen) that binds the protein's His-tag according to the manufacturer's protocol, and the beads are washed several times with Phosphate Buffered Saline (PBS). Again the protein is analyzed by separation on a 12% polyacrylamide gel, and analysis by Coomassie Blue and silver staining.

Deglycosylation

Endoglycosidase H and endoglycosidase F (Boehringer-Mannheim, Mannheim, Germany) are used to cleave N-linked carbohydrates from CALB produced in *P. pastoris*. Digestion is performed according to the manufacturer's instructions under reducing conditions on the NTA beads. The deglycosylated protein is separated by SDS-PAGE on a 12% polyacrylamide gel, and analyzed by staining, and by Western blot analysis using an antibody to the c-myc tag (see above).

Active-Site Titration of Recombinant Lipase

Active-site titration of the purified lipase was performed using a methyl p-nitrophenyl n-hexylphospho-nateinhibitor in order to determine the concentration of active enzyme (Rotticci-Mulder et al. Prot. Expr. & Purif. 2001. Vol. 21, pp. 386–392). The active-site concentration was determined by measuring the concentration of released p-nitrophenolate spectrophotometrically at 25° C. and 400 nm.

Lipase Activity Assay

The hydrolytic activity of the lipase is tested by measuring hydrolysis of tributyrin. The substrate solution (0.2 M tributyrin, 2% gum arabicum, 0.2 M $CaCl_2$) is emulsified by sonication for 1 min. The reaction is initiated by the addition of enzyme to the substrate emulsion. The enzymatic reaction is carried out at 25° C. and pH 7.5, and the level of the enzyme's activity is measured by titration of the released fatty acid with 100 mM sodium hydroxide, using a pH-stat (Rotticci-Mulder et al. Prot. Expr. & Purif. 2001. Vol. 21, pp. 386–392; TIM900 Titration Manager Radiometer, Denmark).

Stabilization of CALB

Introduction of the Dityrosine Bond

Introduction of the dityrosine bond is carried out both on and off the NTA beads. To cross-link the enzyme on the beads, the catalyst, metalloporphyrin 20-tetrakis (4-sulfonateophenyl)-21H,23H-porphine manganese (III) chloride (MnTPPS) is then added to PBS to a concentration of 1 μM, 5 μM, 10 μM, 50 μM and 100 μM to the reaction. The reaction is initiated by the addition of the oxidant potassium mono-persulfate to a concentration of 1–100 μM, at room temperature or otherwise, for each of the concentrations of the catalyst. The beads are agitated, and after 45 seconds, 60 seconds, and 2 minutes the reaction is quenched by the addition of Tris HCl pH7.9 to 50 mM and β-mercaptoethanol to 10 mM, and the beads are washed several times in PBS to remove the catalyst, oxidizing and reducing agents.

To cross-link the enzyme in solution, the protein is eluted from the NTA column according to the manufacturer's protocol, the eluate is equilibrated by dialysis in phosphate buffered saline (PBS), and the protein concentration is adjusted to several concentrations between 100 nM and 1 mM. The catalyst, metalloporphyrin 20-tetrakis (4-sulfonateophenyl)-21H,23H-porphine manganese (III) chloride (MnTPPS) is added on ice to a concentration of 1 μM, 5 μM, 10 μM, 50 μM and 100 μM to the reaction. The reaction is then initiated by the addition of the oxidant potassium mono-persulfate to a concentration of 1–100 μM, at room temperature or otherwise, for each of the concentrations of the catalyst, and at several protein concentrations. After 45 seconds the reaction is quenched by the addition of Tris.Cl pH7.9 to 50 mM and β-mercaptoethanol to 10 mM, and the solution is again dialyzed against PBS to remove the catalyst, oxidizing and reducing agents.

The efficiency of the cross-link reaction is tested by reducing and non-reducing PAGE and Coomassie blue staining.

Improved Stability and Retained Activity

The retained hydrolytic activity of the lipase is tested by incubating equal amounts of the wild type and cross-linked mutants of the enzyme in PBS at 55° C., 60° C., 65° C., and 95° C. for 0, 1, 2, 5, 10, 15, 30, 60, and 90 min. Furthermore, the activity of the enzyme is assayed adding 0, 10 mM, 50 mM, 150 mM, 0.5M, 1M, and 2M of NaCl and other salts, 0 1 mM, 10 mM, 50 mM, 150 mM, 0.5M, and 1M beta mercaptoethanol. The remaining activities of the wild type and various mutants are then assayed hydrolyzing tributyrin, as described above. The enzymatic activity of the wild type and mutant enzymes in various pH conditions is determined spectrophotometrically by measuring the hydrolysis of p-nitrophenyl esters (e.g. p-nitrophenyl palmitate and/or p-nitrophenyl laurate), and the release of p-nitrophenol, at 410 nm.

Dityrosine Stabilization and Directed Evolution

General Approach

The strategy for combining a directed evolution approach with the dityrosine technology described herein is based on the concept that the cross-link conditions can be viewed as a selection environment/selective pressure to which the gene is adapted during the in vitro evolution of the enzyme. In the following, an approach is described that is an adaptation of the approach described by Liebeton et al. (Liebeton et al. "Directed Evolution of an Enantioselective Lipase". Chem. & Biol. 2000. Vol. 7 (9), pp. 709–718). Random mutations are introduced to identify sites that enhance the cross-link efficiency, the enzyme's performance upon cross-linking, or the stability of the protein in the presence of the cross-link. These sites are then further examined by saturation mutagenesis to identify the optimal mutation at the identified site.

Thus, first the mutations to tyrosine are introduced at the selected residues, as described above. Second site mutations are then randomly introduced by error-prone PCR using the mutated gene as the template, and the resulting genes, containing on average approximately 1–2 mutants per copy, are ligated into the expression vector, pYES2. 1 V5-His-TOPO (Invitrogen), and transformed into *S. cerevisiae*.

Secretion of the enzyme is directed by a *S. cerevisiae* signal-peptide. The secreted protein is cross-linked in the supernatants of the cultures, and cross-linked and non-cross-linked protein is heat-treated at 60° C. The resulting enzymes are analyzed by adding a reaction buffer containing substrate specific for lipases, in which the activity of the enzyme can easily be detected by spectrophotometric analysis. Clones identified as more readily cross-linked, more active upon cross-linking, and/or more thermostable, are recovered from the original *S. cerevisiae* clone and sequenced.

Second site mutations identified are further analyzed by saturation mutagenesis. Once the optimal mutation for a site is identified, a construct containing this mutation is used as the template for another round of random second site mutation screening, and saturation mutagenic analysis. This process is iterated 10 to 15 times over.

Vector Construction of pYal-CALB

The DNA encoding the yeast alpha factor-CALB fusion proteins is amplified from the pPal-CALB vectors containing the point mutations, as described above, using the primers Primer C and D described in FIG. 15B. The PCR products are ligated into the pYES2.1/V5-His-TOPO vector (Invitrogen) according to the manufacturer's protocol, and transformed into competent HB101 cells (*E. coli*) according to standard procedures known in the art. The transformants are selected on LB-Amp agar plates. Plasmid DNA is isolated, and the CALB genes (wild type and mutants) are sequenced by standard methods known in the art.

These constructs are isolated and purified using the Qiagen Plasmid Maxi Kit (Qiagen, 2001 catalog number 12162) according to the manufacturer's protocol.

Error Prone PCR Reactions 10 ug of the pYal-CALB vectors are cut with the restriction enzymes EcoRI and NotI, and the resulting linearized plasmid are gel purified using the Qiaex II Gel Extraction Kin (see above) according to the manufacturer's protocol.

A total volume of 50 µl of 67 mM Tria HCl pH 8.8, 16.6 mM $(NH_4)_2SO_4$, 6.1 mM $MgCl_2$, 6.7 mM EDTA, 0.2 mM dNTPs, 10 mM beta-mercaptoethanol, 10% (v/v) DMSO, 0.15 µM each of the Primers E and D, as described in FIG. 15B, contains 1 ng of template DNA and 2 units of Goldstar Taq-polymerase (Eurogentec). Ten parallel samples overlaid with 70 µl paraffin are amplified using the following thermocycling protocol:

1 cycle: 2 min. 95° C.
25 cylcles: 1 min. 94° C., 2 min. 64° C., 1 min. 64° C.
1 cycle: 7 min. 72° C.

PCR products are gel purified with the Qiaex II Gel Extraction Kit, cut with the restriction enzymes EcoRI and NotI, and again gel purified with the Qiaex II Gel Extraction Kit (see above).

In a total volume of 10 µl, 5 pmols each of insert and vector are ligated for two hrs. at room temperature according to standard procedures known in the art. Ligated DNA is transformed into competent HB101 cells according to standard procedures known in the art, and the cells are grown overnight as a culture, selecting for amp. resistance. Plasmid DNA is recovered using the Qiagen Plasmid Midi Kit (Qiagen, 2001 catalog number 12143) according to the manufacturer's protocol.

Transformation and Expression in *S. cerevisiae*

The constructs are transformed into competent, uracil auxotrophic *S. cerevisiae* using the S. C. EasyComp Transformation Kit (Invitrogen, 2001 catalog number k5050-01) according to the manufacturer's protocol. Transformants are isolated on selection plates. Because expression of the inserts in the pYal-CALB vectors is driven by a Gal-inducible promoter, the yeast strains are grown in an SC-U medium with 2% glucose suppressing protein expression (supSC-U) containing 0.67% yeast nitrogen base (without amino acids with ammonium sulfate, 2% glucose, 0.01% each of adenine, arginine, cysteine, leucine, lysine, threonine, tryptophan, and uracil, 0.005% each of aspartic acid, histidine, isoleucine, methionine, phenylalanine, proline, serine, tyrosine, and valine. Protein expression is induced by changing the medium to an SC-U medium with 2% galactose (indSC-U) containing 0.67% yeast nitrogen base (without amino acids with ammonium sulfate, 2% galactose, 0.01% each of adenine, arginine, cysteine, leucine, lysine, threonine, tryptophan, and uracil, 0.005% each of aspartic acid, histidine, isoleucine, methionine, phenylalanine, proline, serine, tyrosine, and valine. Upon induction, the enzymes with and without the point mutations are secreted into the medium, and can easily be affinity purified by their His(6) tags over NTA columns. The optimal period of induction is determined by inducing for 1, 2, 8, and 36 hours and measuring the activities in the cultures supernatants.

Approximately 1000–2000 transformants are each picked with sterile toothpicks and resuspended in a well of a 96-deep-well microtiter plate filled with 1 ml of supSC-U. Cultures are incubated on a shaker overnight at 30° C. To induce protein expression, the cultures are spun down (15 min. at 5000 g), the supernatants are removed, and 1 ml of indSC-U is added to each well. The cultures are spun down, the supernatants are distributed into 96 well plates for analysis of the enzymes (see below), and the cells are resuspended and maintained in supSC-U to be able to recover the plasmid DNA.

Cross-linking in Supernatants of the Cultures

Cross-linked and uncross-linked enzymes are compared after heat-inactivation; because of the large number of colonies to be screened for increased activity/stability, the protein in the 96well plates is cross-linked directly in the supernatants of the cultures.

35 µl of each supernatant is transferred to two 96-well plates to which 5 µl each of 10× PBS, 1 mM MnTPPS (catalyst, see above), and to the samples on one of the 96 well plates, 5 µl of 1 mM $KH_2SO4$ (oxidant) are added. After 2 minutes, the cross-link reaction is quenched in the samples of the plates to which the oxidant was added by the addition of 2.5 µl of 2.88M β-mercaptoethanol. To the samples on the other plate, 7.5 µl of 1×PBS are added.

Lipase Stabilization/Activity Assay

Lipase activity is measured both before and after heat inactivation. The period for which the protein is best heat-treated at 60° C. is determined on the wild-type in a time-course experiment. A cross-linked and a non-cross-linked 96-well plate are each heat-inactivated at 60° C. for the determined period of time. Lipase activities are determined by hydrolysis of p-nitrophenyl palmitate and spectrophotometric analysis at 410 nm, according to the methods published by Liebeton et al. and Winkler & Stuckmann (Liebeton et al. "Directed Evolution of an Enantioselective Lipase". Chem. & Biol. 2000. Vol. 7 (9), pp. 709–718; Winkler & Stuckmann. "Glycogen, Hyaluronate, and Some Other Polysaccharides Greatly Enhance the Formation of Exolipase by *Serratia marcescens*". J. Bacteriol. 1979. Vol. 138, pp. 663–670).

Saturation Mutagenesis

Saturation mutagenesis is performed as described for site directed point mutagenesis, with mutagenic primers in which the codon under investigation is randomized by mixing equal amounts of nucleoside phosphoamidates during synthesis. The optimal codon for that position is again identified by screening approximately 150–200 clones for activity upon cross-linking with and without heat treatment, as described above.

8. EXAMPLE III

Subtilisin E

The following example illustrates certain variations of the methods of the invention for protein and protein complex stabilization. This example is presented by way of illustration and not by way of limitation to the scope of the invention.

Introduction

In the following section, methods of stabilizing one polypeptide, a biocatalyst, for which structural data is available for several structurally or functionally related polypeptides. Specifically, described below are the residue pair selection process, the introduction of point mutations, bacterial expression of the polypeptides and their purification, the cross-link reaction itself, and analysis of the resulting stabilized biocatalyst. For the description of the cross-link reaction and the adjustment of the cross-link reaction conditions, refer to Chapter 6.

The biocatalyst stabilized in the below example is the serine endopeptidase Subtilisin E (FIG. 16A), which is one of the most commercially important biocatalysts. Subtilisin E is a secreted protein of *Bacillus subtilis*, and it cleaves ester and amide bonds. It is used for the total hydrolysis of proteins and peptides at alkaline pH. It has been successfully applied toward the racemic resolution of amino acids, amines, carboxylic acids and alcohols and in peptide synthesis, e.g. D-terminal deprotection.

The structure files containing the three dimensional atomic coordinates of the polypeptides are obtained from the Brookhaven National Laboratory Protein Database. The derivative data relevant to the selection process is calculated as described. In addition to the statistical selection process, carried out using a set of convenient and appropriate filters, data regarding improved stability of the protein upon introduction of disulfide bonds is used to select potential residue pairs to which the cross-link is directed.

Point mutations to tyrosine (directing the cross-link reaction) are introduced according to the final selection of residue pairs (Tables 15 and 16, FIG. 16D), and expressed in *Bacillus subtilis*. The polypeptide is affinity purified and cross-linked, and the resulting biocatalyst is evaluated, as described.

Selection of Optimal Residues for Tyrosyl-Tyrosyl Cross-Link

The selection process consisted of (1) a review of functional data on subtilisin enzymes with improved half-lives upon introduction of disulfide bonds, and (2) the statistical measurements on the alpha carbon distances within the polypeptides of a series of tests or 'filters' aimed at successively narrowing down the residue pairs most likely to result in a cross-linked tyrosine pair that minimally alters the activity or specificity of the enzyme, while lending maximal stability. Furthermore, residue pairs are further evaluated by computationally modeling the mutations to tyrosine.

Data used for the Analysis

Coordinate data for distance calculations of 3 related subtilisin proteins (subtilisin E and BPN, and subtilisin from *Bacillus lentus*) from crystallographically solved structures was downloaded from the protein structure database at Brookhaven National Laboratory These data provide the three-dimensional coordinates (x, y, and z) for each atom in the solved structure, expressed in metric units, i.e. Angströms ($10^{-10}$ m, Å). These data also contain the sequence and/or amino acid usage of the polypeptide. With this data, aligned as shown in FIGS. 16B and C, it was possible to calculate the three-dimensional distances between any desired atoms. Functional data regarding improved stability of the enzyme was taken from the literature (see below).

Selection Methodology

Optimal residues, to which the cross-link reaction is directed, were selected first based on the amino acid usage within the set of structurally and functionally related polypeptides, selecting for residues that in all of the polypeptides of the set are either Trp, Tyr, Phe, Lys, Pro, or His residues. From this set of residues, residue pairs were selected based on their average alpha carbon distances within the set of structurally and functionally related polypeptides. Finally residue pafrs were selected from the above set of residue pairs based on the proximity of the modeled tyrosine side-chains. This was done by modeling the mutations using the automated, knowledge-based protein modeling server Swiss Model, and visualizing the resultant polypeptides' structures, and with the program Swiss pdb Viewer, both of which are available from the proteomics server of the Swiss Institute of Bioinformatics (SIB). Additionally, residue pairs were selected that had previously been mutated to cysteines and formed disulfide bonds, stabilizing the enzyme and maintaining its activity.

FILTER 1: SELECTION OF RESIDUES BASED ON AMINO ACID USAGE

To minimize the distortions that point mutations to tyrosine will introduce into the structure of the enzyme, residues were selected that in every enzyme in the sample have aromatic, or hydrophobic amino acids. Amino acids that were scored for included Trp, Tyr, Phe, His, Pro, Lys, Leu, and Arg, whereby Leu and Arg were only permitted in maximally ⅓ of the sample. Selected residues are listed in Table 13.

TABLE 13

Selected residues based on their amino acid usage.

| Residue | AA Consensus* | Residue | Consensus |
|---------|---------------|---------|-----------|
| 6 | Tyr (W) | 130 | Pro |
| 14 | Pro | 168 | Tyr |
| 17 | His | 169 | Pro |
| 21 | Tyr (K) | 172 | Tyr |
| 27 | Lys | 190 | Phe |
| 39 | His | 202 | Pro |
| 40 | Pro | 211 | Pro |
| 50 | Phe | 215 | Tyr |
| 52 | Pro | 218 | (Leu, Tyr, Lys) |
| 57 | Pro | 226 | Pro |
| 65 | His | 227 | His |
| 68 | His | 238 | Lys |
| 87 | Pro | 240 | pro |
| 92 | Tyr | 242 | Trp |
| 95 | Lys | 263 | Tyr (L) |
| 114 | Trp | 284 | Tyr |

*non-consensus amino acids occurring at a position are indicated in parentheses.

FILTER 2: SELECTION OF RESIDUE PAIRS BASED ON AVERAGE ALPHA CARBON DISTANCES

To find residue pairs spaced appropriately for a tyrosyl-tyrosyl bond, the alpha carbon to alpha carbon distance between every residue pair and each of the polypeptides in the set used for the statistical analysis was calculated in a 3D database. This calculation was performed by applying Pythagorean geometry to the 3D coordinates of the alpha carbons (FIG. 6). Analogously to the selection described in Chapter 7, the range that was selected for was the following:

Min 5.70 Å, Max 9.74 Å.

Furthermore, because the dityrosine bond is intended to stabilize a single polypeptide rather than cross-link two or more proteins of a complex, it was important to select for residues that were sufficiently spaced in the two-dimensional polypeptide chain to maximize the stabilizing effect of the engineered dityrosine bond. Residue pairs were selected that are more than 40 residues apart.

TABLE 14

Aromatic residue pairs with alpha carbon distances within the selection range, each spaced more than 40 residues apart.

| Subtilisin E residue pairs | | Alpha carbon average distance | Alpha carbon distance st. dev. |
|---|---|---|---|
| Tyr6 | Pro202 | 8.2 | 0.32 |
| His17 | Pro87 | 8.9 | 0.08 |
| Tyr21 | Pro87 | 9.5 | 0.16 |
| Tyr21 | Lys238 | 6.3 | 0.51 |
| Lys27 | Tyr92 | 7.4 | 0.09 |
| His39 | Pro211 | 6.8 | 0.22 |
| Phe50 | Lys95 | 6 | 0.04 |
| Phe50 | Trp114 | 9.6 | 0.07 |
| His65 | Pro211 | 9.1 | 0.04 |
| His65 | Tyr218 | 9.0 | 0.03 |
| His68 | Pro211 | 8.2 | 0.06 |
| His68 | Tyr215 | 8.1 | 0.03 |
| His68 | Tyr218 | 8.3 | 0.002 |
| His68 | Pro226 | 9.5 | 0.06 |
| Pro130 | Lys171 | 9.5 | 0.11 |

Based on these calculations, as a second cut, all residue pairs were selected from the set of residues identified based on the residues' amino acid usage that have average alpha carbon distances within the selection range, and that are sufficiently spaced, as listed in Table 13.

Residue Pair Selection Based on Structural Modeling and Visualization of the Mutations By modeling the mutations indicated in Table 14, the likelihood was assessed that each residue pair would form a ditryosine bond, stabilize the enzyme, and introduce minimal distortions into the structure of the protein, particularly in the active site of the enzyme, to maximize its retained activity and specificity. This was achieved by using the automated knowledge-based protein modeling server Swiss Model, and visualizing the resultant polypeptides' structures and with the program Swiss pdbViewer, as stated above. Taking the epsilon carbon distances, calculated in the Swiss pdbViewer, between the modeled tyrosyl side chains into consideration, and the residues' proximity to the active site, residues that looked the most promising were selected. The remaining residue pairs are listed in Table 15.

TABLE 15

List of remaining residue pairs with relevant distance measurements.

| CALB residue pair | | Alpha carbon distance | Cα–Cβ Distance Difference | Epsilon carbon distance* |
|---|---|---|---|---|
| Tyr6 | Pro202 | 8.2 | 0.32 | 4.30 |
| His17 | Pro87 | 8.9 | 0.08 | 5.31 |
| Tyr21 | Lys238 | 6.3 | 0.51 | 4.02 |
| Lys27 | Tyr92 | 7.4 | 0.09 | 5.69 |

*Epsilon carbon distances of the modeled tyrosine pairs.

Selection of Additional Residue Pairs Based of Functional Data

Functional data is available regarding positional suitability of residues at which engineered disulfide bonds improve upon the stability of subtilisin enzymes. This information was taken into account, and residues were added to the selection of Table 15 that were able to confer significant stability by forming a disulfide bond between engineered cystine side-chains while maintaining the enzymes' activity.

Articles containing such data include Takagi et al., 1990 (Enhancement of the Thermostability of Subtilisin E by Introduction of a Disulfide Bond Engineered on the Basis of Structural Comparison with a Thermophilic Serine Protease. JBC 1990. Vol. 265(12); pages 6874–8), Mansfeld et al., 1997 (Extreme Stabilization of a Thermolysin-like Protease by an Engineered Disulfide Bond. JBC 1997. Vol. 272(17); pages 11152–56), Takagi et al., 2000 (Engineering Subtilisin E for Enhanced Stability and Activity in Polar Organic Solvents. J. Biochem. 2000. Vol. 127; pages 617–25), and Mitchinson and Wells (Protein engineering of disulfide bonds in subtilisin BPN'. Biochemistry 1989. Vol. 28(11); pages 4807–15).

In Table 16 below, these additionally-selected residues are listed along with their most relevant functional data.

TABLE 16

Additionally selected residue pairs based on disulfide bond data from the literature.

| Enzyme | Mutations/Disulfide positions | Secondary Structures* | Half-life | Activity |
|---|---|---|---|---|
| Subt. E & BPN | G61C/S98C & N61C/A98C | H3–BS3 | 2–3 × w/t | w/t |
| Subt. E | K170C/E195C | BS6–BS7 | 60% w/t | 46% w/t |
| BPN | D36C/P210C | BS2–BS8 | w/t | No report |

*Secondary structures cross-linked by the disulfide bond. H: alpha helix; BS: beta sheet.

Introduction of the Point Mutations at the Selected Residues

According to the final selection of residue pairs (Tables 15 and 16, FIG. 16D), PCR is used to introduce point mutations to tyrosine, and nucleotides are added to the 3' end of the wild type and mutant genes (FIG. 16D, Primers A and B) to introduce a poly-histidine tag to the polypeptide. Point mutations are introduced by PCR using the QuickChange™ Site-Directed Mutagenesis Kit (Stratagene, 1998 Catalog # 200518). The 5' primer (FIG. 16D, Primer A) creates an NdeI site, and the 3' primer (FIG. 16D, Primer B) creates a BamnH1 site.

The PCR product is digested with NdeI and BamHI, purified, and ligated into the multiple cloning site of a shuttle expression-vector that propagates both in bacillus and in E. coli, and that directs expression of the polypeptide under the Bacillus subtilis subtilisin promoter (PBE3, Zhao and Arnold, 1999). Ligated constructs are transformed into competent HB101 cells, grown, isolated, and analyzed by standard restriction enzyme digestion and sequencing.

Expression and Purification of the Protein

To express the proteins, the plasmids described above are transformed into competent cells of a strain of subtilisin negative bacillus subtilis (DB428; Zhao and Arnold, 1999). Cells are grown for 36 hours at 37° C., and protein is purified from the supernatants of the cultures.

The protein is bound to NTA column supplied by Invitrogen that binds the proteins' His-tags, by methods known to one skilled in the art, and/or according to the manufacturer's protocol, and the beads are washed several times with Phosphate Buffered Saline (PBS). The cross-link reaction and the adjustment of the reaction conditions, as otherwise described in Chapter 6, are carried out on the beads in PBS containing the catalyst of the cross-link reaction, 20 tetrakis (sulfonatophenyl)-21H,23H-porphorine manganese (III) chloride (MnTTP), and the oxidant, $KHSO_5$, supplied by Fluka as 47% of a mixture containing $KHSO_4$ and $K_2SO_4$.

Analysis of the Resultant Cross-Linked Enzyme

The assay for the activities of the various mutants of the enzyme are carried out using 0.2 mM suc-AAPF-pNa as the substrate in a buffer containing 100 mM Tris 8.0 and 10 mM $CaCl_2$. The activity is monitored spectrophotometrically by measuring absorbance of the reaction mixture at a wave length of 410 nm.

The enzymes are analyzed, first to determine the mutants' activity before cross-linking, relative to the wild-type enzyme. Enzymes purified from 100 µl of the cultures supernatants are analyzed for their activity by letting the enzyme assay reaction run for 0, 30, 60, and 90 min. Furthermore, the enzymes are analyzed for activity before and after cross-linking, as described above. Finally, the stability of the enzymes is determined by time-course heat inactivation experiments, where the enzymes are incubated for 0, 1, 2, 5, 15, and 60 minutes at 45° C., 55° C., 65° C., and 95° C.

9. References

Campbell L. A. et al. Protein Cross-linking Mediated by Metalloporphyrins. Bioorganic and Medicinal Chemistry, vol. 6: pp. 1301–1037, 1998

Brown K. C. et al. Highly Specific Oxidative Cross-link of Proteins Mediated by a Nickel-peptide Complex. Biochem.; vol. 34(14): pp. 4733–4739, 1995

Pollitt S. and Schultz P. Agnew. Chem. Int. Ed.; vol. 37(15): pp. 2104–2107, 1998

Spangler B. D. and Erman J. E. Cytochrome c Peroxidase Compound I: Formation of Covalent Protein Crosslinks During the Endogenous Reduction of the Active Site. Biochim. Biophys. Acta; vol. 872(1–2): pp. 155–7, 1986

Gmeiner B. and Seelos C. Phosphorylation of Tyrosine Prevents Dityrosine Formation in vitro. FEBS Lett; vol. 255(2): pp. 395–7, 1989

Kanwar R. and Balasubramanian D. Structure and Stability of the Dityrosine-linked Dimer of GammaB-crystallin. Exp. Eye Res.; vol. 68(6): pp. 773–84, 1999

Fancy D. A. and Kodadek T. Chemistry for the Analysis of Protein-protein Interactions: Rapid and Efficient Cross-linking Triggered by Long Wavelength Light. Proc. Natl. Acad. Sci., U.S.A.; vol. 96: pp. 6020–24, 1999

Klinman J. P. (ed.). Redox-active Amino Acids in Biology. Methods in Enzymology; vol. 258, 1995

Richards, F. M. The Interpretation of Protein Structures: Total Volume, Group Volume Distributions and Packing Density. J. Mol. Biol.; vol. 82: pp. 1–14, 1974

Eisenberg, D. Three-dimensional Structure of Membrane and Surface Proteins. Ann. Rev. Biochem.; vol. 53: pp. 595–623, 1984

National Brookhaven Laboratory Protein Database

Pastan et al. Recombinant Disulfide Stabilized Polypeptide Fragments Having Binding-specificity. U.S. Pat. No. 5,747,654, issued May 5, 1998

Hofmann K. The Modular Nature of Apoptotic Signaling Proteins. Cell Mol. Life Sci.; vol. 55(8–9): pp. 1113–28, 1999

Johnson, G. et al. Weir's Handbook of Experimental Immunology I. Immunochemistry and Molecular Immunology, Fifth Edition, Ed. L. A. Herzenberg, W. M. Weir, and C. Blackwell, Blackwell Science Inc., Cambridge, Me., Chapter 6.1–6.21, 1996

Wickelgren I. Mining the genome for drugs. Science; vol. 285(5430): pp. 998–1001, 1999

Leong S. R. et al. IL-8 single-chain homodimers and heterodimers: interactions with chemokine receptors CXCR1, CXCR2, and DARC. Protein Sci.; vol. 6(3): pp: 609–17, 1997

Pawson T. Tyrosine Kinase Signalling Pathways. Princess Takamatsu Symp.; vol.24: pp.303–22, 1994

Cowburn D. Peptide Recognition by PTB and PDZ Domains. Curr. Opin. Struct. Biol.; vol. 7(6): pp. 835–8, 1997

Bockaert J. and Pin J. P. Molecular Tinkering of G Protein-coupled Receptors: an Evolutionary Success. EMBO J.; vol. 18(7): pp. 1723–9, 1999

Royet J. et al. Notchless Encodes a Novel WD40-repeat-containing Protein that Modulates Notch Signaling Activity. EMBO J.; vol. 17(24): pp. 7351–60, 1998

Chou J. J. et al. Solution Structure of the RAIDD CARD and Model for CARD/CARD Interaction in Caspase-2 and Caspase-9 Recruitment. Cell; vol. 94(2): pp. 171–80, 1998

Black R. A. and White J. M. ADAMs: Focus on the Protease Domain. Curr Opin Cell Biol.; vol. 10(5): pp. 654–9, 1998

Strasser A. and Newton K. FADD/MORT1, a Signal Transducer that Can Promote Cell Death or Cell Growth. Int. J. Biochem. Cell. Biol.; vol. 31(5): pp. 533–7, 1999

McInnes C. and Sykes B. D. Growth Factor Receptors: Structure, Mechanism, and Drug Discovery. Biopolymers; vol. 43(5): pp. 339–66, 1997

Lotz M. et al. The Nerve Growth Factor/Tumor Necrosis Factor Receptor Family. J. Leukoc. Biol.; vol. 60(1): pp. 1–7, 1996

Casaccia-Bonnefil P. et al. p75 Neurotrophin Receptor as a Modulator of Survival and Death Decisions. Microsc Res Tech.; vol. 45(4–5): pp. 217–24, 1999

Natoli G. et al. Apoptotic, Non-apoptotic, and Anti-apoptotic Pathways of Tumor Necrosis Factor Signalling. Biochem. Pharmacol.; vol. 56(8): pp. 915–20, 1998

Alber T. Structure of the Leucine Zipper. Curr. Opin. Genet. Dev.; vol. 2(2): pp. 205–10, 1992

Griffith T. S. et al. Functional Analysis of TRAIL Receptors Using Monoclonal Antibodies. J. Immunol.; vol. 162 (5): pp. 2597–605, 1999

Yasuda H. et al. Identity of Osteoclastogenesis Inhibitory Factor (OCIF) and Osteoprotegerin (OPG): a Mechanism by which OPG/OCIF Inhibits Osteoclastogenesis in vitro. Endocrinology; vol. 139(3): pp. 1329–37, 1998

Ortiz A. et al. New Kids in the Block: the Role of FasL and Fas in Kidney Damage. J. Nephrol.; vol. 12(3): pp. 150–8, 1999

Price Waterhouse: Survey of Biopharmaceutical Industry, 1998 Boston Consulting Group: The Contribution of Pharmaceutical Companies: What's at stake for America, 1993

Pharmaceutical Research and Manufacturers of America. New Medicines in Develoment, Survey.

Penuche M. L. et al. Antibody-IL-2 Fusion Proteins: a Novel Strategy for Immune Protection. Hum Antibodies; vol. 8(3): pp. 106–18, 1997

Sensel M. G. et al. Engineering Novel Antibody Molecules. Chem. Immunol.; vol. 65: pp. 129–58, 1997

Reiter Y. and Pastan I. Recombinant Fv Immunotoxins and Fv Fragments as Novel Agents for Cancer Therapy and Diagnosis. TIBTECH; vol. 16(12): pp. 513–520, 1998

Reiter Y. et al. Engineering Antibody Fv Fragments for Cancer Detection and Therapy: Disulfide-stabilized Fv Fragments. Nat Biotech.; vol. 14: pp. 1239–1245, 1996

Pluckthun A. and P. Pack. New Protein Engineering Approaches to Multi-valent and Bi-specific Antibody Fragments. Immunotechnology; vol. 3(2): pp. 83–105, 1997

Wright A. and Morrison S. L. Effect of Glycosylation on Antibody Function: Implications for Genetic Engineering. Trends Biotechnol.; vol. 15(1): pp. 26–32, 1997

Schwartz M. A. et al. Monoclonal Antibody Therapy. Cancer Chemother. Biol. Response Modif.; vol. 13:pp. 156–74, 1992

Houghton A. N. and Scheinberg D. A. Monoclonal Antibodies: Potential Applications to the Treatment of Cancer. Semin Oncol.; vol. 13(2): pp. 165–79, 1986

Cao Y. and Suresh M. R. Bi-specific Antibodies as Novel Bio-conjugates. Bioconjugate Chemistry; vol. 9(6): pp. 635–644, 1998

Raag R. and Whitlow M. Single-chain Fvs. FASEB; vol. 9: pp. 73–80, 1995

Webber K. O. et al. Preparation and Characterization of a Disulfide-stabilized Fv Fragment of the Anti-Tac Antibody: Comparison with its Single-chain Analog. Mol. Immunol.; vol. 32(4): pp. 249–258, 1995

Klinman J. P. (ed.). Redox-active Amino Acids in Biology. Methods in Enzymology, vol. 258, 1995

Bosilevac J. M. et al. Inhibition of Activating Transcription Factor 1- and cAMP-responsive Element-binding Protein-activated Transcription by an Intracellular Single-chain Fv fragment. J. Biol. Chem.; vol. 273(27): pp. 16874–16879, 1998

Graus-Porta D. et al. Single Chain Mediated Intracellular Retention of ErbB-2 Impairs Neu Differentiation Factor and Epidermal Growth Factor Signaling. Mol. Cell Biol.; vol 15: pp. 1182–1191, 1995

Richardson J. H. et al. Phenotypic Knockout of the High-affinity Interleukin 2 Receptor by Intracellular Single Chain Antibodies against the Alpha Subunit of the Receptor. Proc. Nat. Acad. Sci., USA; vol. 92: pp. 3137–3141, 1995

Maciejewski J. P. et al. Intracellular Expression of Antibody Fragments Directed against Human Immunodeficiency Virus Reverse Transcriptase Prevents HIV Infection in vitro. Nat. Med.; vol. 1: pp. 667–673, 1995

Marasco W. A. et al. Design, Intracellular Expression, and Activity of a Human Anti-human Immunodeficiency Virus Type I gp120 Single Chain Antibody. Proc. Nat. Acad. Sci., USA; vol. 90: pp. 7889–7893, 1993

Levy Mintz P.et al. Intracellular Expression of Single Chain Variable Fragment to Inhibit Early Stages of the Virla Life Cycle by Targeting Human Immunodeficiency Virus Type 1 Integrase. J. Virol.; vol. 70: pp. 8821–8832, 1996

Duan L. et al. Intracellular Immunization Against Human Immunodeficiency Virus Type I Infection of Human T Lymphocytes: Utility of Anti-rev Single Chain Variable Fragment. Hum. Gene Ther.; vol. 6(12): pp. 1561–1573, 1995

Kim S. H. et al. Expression and Characterization of Recombinant Single-chain Fv and Fv Fragments Derived from a Set of Catalytic Antibodies. Mol. Immunol.; vol. 34(12–13): pp. 891–906, 1997

Choi C. W. et al. Biodistribution of 18F- and 125I-labelled Anti-Tac Disulfide-stabilized Fv Fragments in Nude Mice with Interleukin 2 a Receptor-positive Tumor Xenografts. Cancer Research; vol. 55: pp. 5323–5329, 1995

Colcher D. et al. Pharmacokinetics and Biodistribution of Genetically-engineered Antibodies. Q J Nucl Med.; vol. 42(4): pp. 225–41, 1998

Pavlinkova G. et al. Pharmacokinetics and Biodistribution of Engineered Single-chain Antibody Constructs of MAb CC49 in Colon Carcinoma Xenografts. J. Nucl. Med.; vol. 40(9): pp. 1536–46, 1999

Antibody Engineering Page, IMT, University of Marburg, FRG

Hunkapiller M. et al. A Microchemical Facility for the Analysis and Synthesis of Genes and Proteins. Nature; vol. 310(5973): pp. 105–11, 1984

Xia X and Li W H. What Amino Acid Properties Affect Protein Evolution, J. Mol. Evol.; vol. 47(5): pp. 557–64, 1998

Sandberg M, et al. New Chemical Descriptors Relevant for the Design of Biologically Active Peptides. A Multivariate Characterization of 87 Amino Acids. J. Med. Chem.; vol. 41(14): pp. 2481–91, 1998

Hopp T. P. and Woods K. R. Prediction of Protein Antigenic Determinants from Amino Acid Sequences. Proc. Natl. Acad. Sci., U.S.A.; vol. 78: pp. 3824, 1981

Bradford, M. A Rapid and Sensitive Method for the Quantitation of Microgram Quantities of Protein Utilizing the Principle of Protein-dye Binding. Anal. Biochem.; vol. 72: pp. 248–54, 1976

Lowry, O. J. Biol. Chem.; vol. 193, pp. 265, 1951

Lei S. P. et al. Characterization of the Erwinia Carotovora pelB Gene and its Product Pectate Lyase. J. Bacteril.; vol. 169: pp. 4379–83, 1987

Chou P. Y. and Fasman G. D. Prediction of Protein Conformation. Biochemistry; vol. 13(2): pp. 222–45, 1974

Lang L. and Eckelmann W. C. One-step Synthesis of 18F labeled [18F]-N-succinimidyl 4-(fluoromethyl)benzoate for Protein Labeling. Appl. Radiat. Isot.; vol. 45: pp. 1155–63, 1994

Sambrook et al.; Glover (ed.). DNA Cloning: A Practical Approach. MRL Press, Ltd., Oxford, U.K.; vol. I, II, 1985

Benton and Davis. Screening Lambdagt Recombinant Clones by Hybridization to Single Plaques in situ. Science; vol. 196(4286): pp. 180–2, 1977

Clemmons D. R. IGF Binding Proteins and their Functions. Mol. Reprod. Dev.; vol. 35: pp. 368–374, 1993

Loddick S. A. et al. Displacement of Insulin-like Growth Factors from their Binding Proteins as a Potential Treatment for Stroke. Proc. Natl. Acad. Sci., U.S.A.; vol. 95: pp. 1894–1898, 1998

Swift G. H. et al. Tissue-specific expression of the rat pancreatic elastase I gene in transgenic mice. Cell; vol. 38:pp. 639–646, 1984

Hanahan D. Heritable formation of pancreatic beta-cell tumours in transgenic mice expressing recombinant insulin/simian virus 40 oncogenes. Nature; vol. 315: pp. 115–122, 1985

Grosschedl R. et al Introduction of a mu immunoglobulin gene into the mouse germ line: specific expression in lymphoid cells and synthesis of functional antibody. Cell; vol. 38: pp. 647–658, 1984

Leder A et al. Consequences of widespread deregulation of the c-myc gene in transgenic mice: multiple neoplasms and normal development. Cell; vol. 45: pp. 485–495, 1986

Pinkert C. A. et al. An albumin enhancer located 10 kb upstream functions along with its promoter to direct efficient, liver-specific expression in transgenic mice. Genes Dev.; vol. 1: pp. 268–276, 1987

Krumlauf R. et al. Developmental regulation of alpha-fetoprotein genes in transgenic mice. Mol. Cell. Biol.; vol. 5: pp. 1639–1648, 1985

Kelsey G. D. et al. Species- and tissue-specific expression of human alpha 1-antitrypsin in transgenic mice. Genes Dev.; vol. 1: pp. 161–171, 1987

Magram J. et al. Developmental regulation of a cloned adult beta-globin gene in transgenic mice. Nature; vol. 315: pp. 338–340, 1985

Readhead C. et al. Expression of a myelin basic protein gene in transgenic shiverer mice: correction of the dysmyelinating phenotype. Cell; vol. 48: pp. 703–712, 1987

Shani M. Tissue-specific expression of rat myosin light-chain 2 gene in transgenic mice. Nature; vol. 314: pp. 283–286, 1985

Mason A. J. et al. The hypogonadal mouse: reproductive functions restored by gene therapy. Science; vol. 234: pp. 1372–1378, 1986

Smith D. B. and Johnson K. S. Single-step purification of polypeptides expressed in Escherichia coli as fusions with glutathione S-transferase. Gene; vol. 67: pp. 31–40, 1988

Lei S. P. et al. Characterization of the Erwinia carotovora pelB gene and its product pectate lyase. J. Bacteril., vol. 169: pp. 4379, 1987

Kim S. H. et al. Expression and characterization of recombinant single-chain Fv and Fv fragments derived from a set of catalytic antibodies. Mol. Immunol, vol. 34: pp. 891–906, 1997

Cale J. M. et al. Optimization of a reverse transcription-polymerase chain reaction (RT-PCR) mass assay for low-abundance mRNA. Methods Mol. Biol.; vol. 105: pp. 351–71, 1998

Weis J. H. et al. Detection of rare mRNAs via quantitative RT-PCR. Trends Genet.; vol. 8(8): pp. 263–4, 1992

Frohman M. A. On beyond classic RACE (rapid amplification of cDNA ends). PCR Methods Appl.; vol.4(1): pp. S40–58, 1994

Adams P. D. et al. Extending the limits of molecular replacement through combined simulated annealing and maximum-likelihood refinement. Acta Crystallogr. D. Biol. Crystallogr.; vol. 55 (Pt 1): pp. 181–90, 1999

Schwarze S. R. et al. In Vivo Protein Transduction: Delivery of a Biologically Active Protein into the Mouse. Science; vol. 285: pp. 1565–72, 1999

Hoffman R. M. Topical liposome targeting of dyes, melanins, genes, and proteins selectively to hair follicles. J. Drug Target.; vol. 5(2): pp. 67–74, 1998

Pluckthun A. et al. Catalytic antibodies: contributions from engineering and expression in Escherichia coli. Ciba Found. Symp.; vol. 159: pp. 103–12; discussion 112–7, 1991

Guogiang J. et al. Dimerization Inhibits the Activity of Receptor-like Protein-tyrosine Phosphatase alpha. Nature; vol. 401: pp.606–610, 1999

BIC, Explorer, Business Opportunities in Technology Commercialization.

Illanes A. Stability of biocatalysts. Elec.J.Biotech., vol. 2(1): pp. 7–15, 1999

DeSantis G. and Jones J. B. Chemical modification of enzymes for enhanced functionality. Curr. Op. Biotech., vol. 10(4): pp. 324–340, 1999

Govardhan C. P. Crosslinking of enzymes for improved stability and performance. Curr Opin Biotechnol. Aug; vol 10(4):331–5, 1999

Beguin P. Hybrid enzymes. Curr. Op. Biotech., vol. 10(4): pp. 336–340, 1999

Haring D. and Schreier P. Cross-linked enzyme crystals. Curr Opin Chem Biol.; vol. 3(1): pp. 35–8, 1999

Moreno-Hagelsieb G. and Soberon X. Protein engineering as a powerful tool for the chemical modification of enzymes. Biol Res.; vol. 29(1): pp. 127–40, 1996

Jaeger K-E. et al. Bacterial Biocatalysts: Molecular Biology, Three-Dimensional Structures, and Biotechnological Applications of Lipases. Annu. Rev. Microbiol. vol. 53: pp. 315–51, 1999

Carrea G. and Riva S. Properties and Synthetic Applications of Enzymes in Organic Solvents. Angew Chem Int Ed Engl. Vol. 39(13): pp. 2226–2254, 2000

Stemmer W. P. C. Rapid Evolution of a Protein in Vitro by DNA Shuffling. Nature. Vol. 370: pp. 389–391, 1994

Zhao H. and Arnold F. H. Optimization of DNA Shuffling for High Fidelity Recombination. Nucleic Acids Res. Vol. 25: pp. 1307–1308, 1997

Zhao H. et al. Molecular Evolution by Staggered Extension Process (StEP) in Vitro Recombination. Nat. Biotechnol. Vol 16: pp. 258–261, 1998

Shao Z. et al. Random-priming in vtro Recombination: an Effective Tool for Directed Evolution. Nucleic Acids Res. Vol. 26: pp. 681–683, 1998

Vo-Dinh T. and Cullum B. Biosensors and Biochips: Advances in Biological and Medical Diagnostics. Fresenius J Anal Chem. Vol. 366: pp. 540–551, 2000

Patkar et al. Effect of Mutations in Candida Antarctica B Lipase. Chem.& Phys. Of Lipids. Vol. 93, pp. 95–101, 1998

Rotticci-Mulder et al. Expression in Pichia Pastoris of Candida Antarctica Lipase B and Lipase B Fused to a Cellulose Binding Domain. Prot. Expr. & Purif. Vol. 21, pp. 386–392, 2001

Winkler & Stuckmann. Glycogen, Hyaluronate, and Some Other Polysaccharides Greatly Enhance the Formation of Exolipase by Serratia marcescens. J. Bacteriol. Vol. 138, pp. 663–670, 1979

Liebeton et al. Directed Evolution of an Enantioselective Lipase. Chem. & Biol. 2000. Vol. 7 (9), pp. 709–718

Schmidt-Dannert. Recombinant Microbial Lipases for Biotechnological Applications. Bioorg. & Med. Chem. Vol. 7, pp. 2123–2130, 1999

Takagi et al. Enhancement of the Thermostability of Subtilisin E by Introduction of a Disulfide Bond Engineered on the Basis of Structural Comparison with a Thermophilic Serine Protease. JBC. Vol. 265(12); pages 6874–78, 1990

Mansfeld et al. Extreme Stabilization of a Thermolysin-like Protease by an Engineered Disulfide Bond. JBC. Vol. 272(17); pages 11152–56, 1997

Takagi et al. Engineering Subtilisin E for Enhanced Stability and Activity in Polar Organic Solvents. J. Biochem. Vol. 127; pages 617–25, 2000

Mitchinson and Wells. Protein Engineering of Disulfide Bonds in Subtilisin BPN'. Biochemistry. Vol. 28(11); pages 4807–15, 1989

Zhao and Arnold. Directed Evolution Converts Subtilisin E into a Functional Equivalent of Thermitase. Protein Eng. Vol.12(1): pages 47–53, 1999

The invention claimed and described herein is not to be limited in scope by the specific embodiments, including but not limited to the deposited microorganism embodiments, herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. An isolated protein having a functional activity selected from the group consisting of an enzymatic activity, an antigen-binding activity, a protein-protein interaction activity, a DNA binding activity, a hormone activity, a receptor activity, a growth factor activity, and any combinations thereof, comprising at least one di-tyrosine cross-link, wherein at least one tyrosine of a di-tyrosine cross-link originates from a point mutation to tyrosine, and wherein the di-tyrosine cross-linked protein retains at least one functional activity displayed by the protein in the absence of di-tyrosine cross-linking.

2. The protein of claim 1, further comprising at least one amino acid which originates from a point mutation from tyrosine such that the amino acid is not cross-linked under cross-linking conditions.

3. The protein of claim 1, wherein the protein has enhanced stability compared to the same protein in the absence of di-tyrosine cross-linking.

4. The protein of claim 1, wherein the protein is an enzyme, an antibody, a hormone, a growth factor, a receptor, or a fragment of a hormone, a receptor, a growth factor, an enzyme or an antibody.

5. A method for making a stabilized protein, wherein the protein has a functional activity selected from the group consisting of an enzymatic activity, an antigen-binding activity, a protein-protein interaction activity, a DNA binding activity, a hormone activity, a receptor activity, a growth factor activity, and any combinations thereof, comprising:

(a) selecting one or more residue pairs in a polypeptide chain or chains for di-tyrosine cross-linking, (b) mutating at least one of the selected residues to tyrosine; and (c) cross-linking the residue pairs in the presence of an oxidant;

wherein the di-tyrosine cross-linked protein retains at least one functional activity displayed by the protein in the absence of di-tyrosine cross-linking, and wherein at least one tyrosine of a di-tyrosine cross-link originates from a point mutation to tyrossine.

6. The method of claim 5, wherein the di-tyrosine cross-link reaction occurs in the presence of one or more oxidants selected from the group consisting of hydrogen peroxide, oxone, magnesium monoperoxyphthalic acid hexahydrate (MMPP), a photogenerated oxidant, ammonium persulfate, or any combination thereof.

7. The method of claim 6, wherein the di-tyrosine cross-linking is catalyzed by a catalyst selected from the group consisting of polyhistidine, Gly-Gly-His, a metalloporphyrin, a peroxidase or any combination thereof.

8. The protein of claim 5, wherein the protein is a hormone, a receptor, a growth factor, an enzyme, an antibody, or a fragment of a hormone, a receptor, a growth factor, an enzyme or an antibody.

9. The protein of any of claims 1–4 or 8, wherein the protein is part of a pharmaceutical composition.

10. The protein of claim 9, wherein the pharmaceutical composition comprises a pharmaceutically acceptable carrier.

11. The protein of claim 9, wherein the pharmaceutical composition is suitable for in vivo use in humans.

12. The protein of claim 1, wherein the protein is a chimeric polypeptide comprising a hormone, a receptor, a growth factor, an enzyme, an antibody, or a fragment of an enzyme, a hormone, a growth factor, a receptor, or an antibody.

13. The protein of any of claims 1–4, 8 or 12, wherein the protein is part of a kit.

14. A composition comprising a protein of any of claims 1–4, 8 or 12.

15. The composition of claim 14, wherein the composition is part of a kit.

16. An isolated stabilized protein having a functional activity selected from the group consisting of an enzymatic activity, an antigen-binding activity, a protein-protein interaction activity, a DNA binding activity, a hormone activity, a receptor activity a growth factor activity, and any combinations thereof, wherein the protein is obtained from a method comprising:

(a) selecting one or more residue pairs in a protein for di-tyrosine cross-linking, (b) mutating at least one of the selected residues to tyrosine;

(c) isolating the protein; and (d) cross-linking tyrosine residue pairs in the presence of an oxidant;

wherein the di-tyrosine cross-linked protein retains at least one functional activity displayed by the protein in the absence of di-tyrosine cross-linking, and wherein at least one tyrosine of a di-tyrosine cross-link originates from a point mutation to tyrosine.

17. The protein of claim 16, further comprising at least one amino acid which originates from a point mutation from tyrosine such that the amino acid is not cross-linked under cross-linking conditions.

18. The protein of claim 5 or 16, wherein the protein has enhanced stability compared to the protein in the absence of di-tyrosine cross-linking.

19. The protein of claim 16, wherein the protein is an enzyme, a hormone, a growth factor, a receptor, an antibody, or a fragment of an enzyme, a hormone, a growth factor, a receptor, or an antibody.

20. The protein of claim 16, wherein the di-tyrosine cross-link reaction occurs in the presence of one or more oxidants selected from the group consisting of hydrogen peroxide, oxone, magnesium monoperoxyphthalic acid hexahydrate (MMPP), a photogenerated oxidant, ammonium persulfate, or any combination thereof.

21. The protein of claim 16, wherein the di-tyrosine cross-linking is catalyzed by a catalyst selected from the group consisting of polyhistidine, Gly-Gly-His, a metalloporphyrin, a peroxidase or any combination thereof.

22. The protein of claim 16, wherein the protein is a chimeric polypeptide comprising a hormone, a receptor, a growth factor, an enzyme, an antibody, or a fragment of an enzyme, a hormone, a growth factor, a receptor, or an antibody.

23. A composition comprising a protein of claim 16 or 22.

24. A kit comprising the protein of claim 16 or 22.

25. A kit comprising the composition of claim 23.

* * * * *

UNITED STATES PATENT AND TRADEMARK OFFICE
CERTIFICATE OF CORRECTION

PATENT NO. : 7,037,894 B2
APPLICATION NO. : 09/837235
DATED : May 2, 2006
INVENTOR(S) : Christopher P. Marshall et al.

It is certified that error appears in the above-identified patent and that said Letters Patent is hereby corrected as shown below:

Title Page, Item (75), Inventors
Please delete "Paul B. Marshall, Munich (DE)"

Signed and Sealed this

Twelfth Day of January, 2010

David J. Kappos
*Director of the United States Patent and Trademark Office*

SEQUENCE LISTING

<160> NUMBER OF SEQ ID NOS: 42

<210> SEQ ID NO 1
<211> LENGTH: 954
<212> TYPE: DNA
<213> ORGANISM: Candida antarctica

<400> SEQUENCE: 1

```
ctaccttccg gttcggaccc tgccttttcg cagcccaagt cggtgctcga tgcgggtctg      60
acctgccagg gtgcttcgcc atcctcggtc tccaaaccca tccttctcgt ccccggaacc     120
ggcaccacag gtccacagtc gttcgactcg aactggatcc ccctctcaac gcagttgggt     180
tacacaccct gctggatctc accccgccg ttcatgctca acgacaccca ggtcaacacg      240
gagtacatgg tcaacgccat caccgcgctc tacgctggtt cgggcaacaa caagcttccc     300
gtgcttacct ggtcccaggg tggtctggtt gcacagtggg gtctgacctt cttccccagt     360
atcaggtcca aggtcgatcg acttatggcc tttgcgcccg actacaaggg caccgtcctc     420
gccggccctc tcgatgcact cgcggttagt gcaccctccg tatggcagca aaccaccggt     480
tcggcactca ccaccgcact ccgaaacgca ggtggtctga cccagatcgt gcccaccacc     540
aacctctact cggcgaccga cgagatcgtt cagcctcagg tgtccaactc gccactcgac     600
tcatcctacc tcttcaacgg aaagaacgtc caggcacagg ccgtgtgtgg gccgctgttc     660
gtcatcgacc atgcaggctc gctcacctcg cagttctcct acgtcgtcgg tcgatccgcc     720
ctgcgctcca ccacgggcca ggctcgtagt gcagactatg gcattacgga ctgcaaccct     780
cttcccgcca atgatctgac tcccgagcaa aaggtcgccg cggctgcgct cctggcgccg     840
gcagctgcag ccatcgtggc gggtccaaag cagaactgcg agcccgacct catgccctac     900
gcccgcccct ttgcagtagg caaaaggacc tgctccggca tcgtcacccc ctga           954
```

<210> SEQ ID NO 2
<211> LENGTH: 317
<212> TYPE: PRT
<213> ORGANISM: Candida antarctica

<400> SEQUENCE: 2

```
Leu Pro Ser Gly Ser Asp Pro Ala Phe Ser Gln Pro Lys Ser Val Leu
  1               5                  10                  15

Asp Ala Gly Leu Thr Cys Gln Gly Ala Ser Pro Ser Ser Val Ser Lys
                 20                  25                  30

Pro Ile Leu Leu Val Pro Gly Thr Gly Thr Thr Gly Pro Gln Ser Phe
             35                  40                  45

Asp Ser Asn Trp Ile Pro Leu Ser Thr Gln Leu Gly Tyr Thr Pro Cys
         50                  55                  60

Trp Ile Ser Pro Pro Phe Met Leu Asn Asp Thr Gln Val Asn Thr
 65                  70                  75                  80

Glu Tyr Met Val Asn Ala Ile Thr Ala Leu Tyr Ala Gly Ser Gly Asn
                 85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
        130                 135                 140
```

```
Asp Ala Leu Ala Val Ser Ala Pro Ser Val Trp Gln Gln Thr Thr Gly
145                 150                 155                 160
Ser Ala Leu Thr Thr Ala Leu Arg Asn Ala Gly Gly Leu Thr Gln Ile
                165                 170                 175
Val Pro Thr Thr Asn Leu Tyr Ser Ala Thr Asp Glu Ile Val Gln Pro
            180                 185                 190
Gln Val Ser Asn Ser Pro Leu Asp Ser Ser Tyr Leu Phe Asn Gly Lys
        195                 200                 205
Asn Val Gln Ala Gln Ala Val Cys Gly Pro Leu Phe Val Ile Asp His
    210                 215                 220
Ala Gly Ser Leu Thr Ser Gln Phe Ser Tyr Val Val Gly Arg Ser Ala
225                 230                 235                 240
Leu Arg Ser Thr Thr Gly Gln Ala Arg Ser Ala Asp Tyr Gly Ile Thr
                245                 250                 255
Asp Cys Asn Pro Leu Pro Ala Asn Asp Leu Thr Pro Glu Gln Lys Val
            260                 265                 270
Ala Ala Ala Ala Leu Leu Ala Pro Ala Ala Ala Ile Val Ala Gly
        275                 280                 285
Pro Lys Gln Asn Cys Glu Pro Asp Leu Met Pro Tyr Ala Arg Pro Phe
    290                 295                 300
Ala Val Gly Lys Arg Thr Cys Ser Gly Ile Val Thr Pro
305                 310                 315

<210> SEQ ID NO 3
<211> LENGTH: 57
<212> TYPE: DNA
<213> ORGANISM: Candida antarctica

<400> SEQUENCE: 3
atgggaattc catcatcatc atcatcacag cagcggccta ccttccggtt cggaccc          57

<210> SEQ ID NO 4
<211> LENGTH: 37
<212> TYPE: DNA
<213> ORGANISM: Candida antarctica

<400> SEQUENCE: 4
ctcttggcgg ccgcctatca gggggtgacg atgccgg                                37

<210> SEQ ID NO 5
<211> LENGTH: 68
<212> TYPE: DNA
<213> ORGANISM: Candida antarctica

<400> SEQUENCE: 5
atgggaattc catcatcatc atcatcacag cagcggccta ccttccggtt cggaccctgc       60
ctattcgc                                                                68

<210> SEQ ID NO 6
<211> LENGTH: 24
<212> TYPE: DNA
<213> ORGANISM: Candida antarctica

<400> SEQUENCE: 6
cgactcgaac tacatccccc tctc                                              24
```

```
<210> SEQ ID NO 7
<211> LENGTH: 24
<212> TYPE: DNA
<213> ORGANISM: Candida antarctica

<400> SEQUENCE: 7
gagaggggga tgtagttcga gtcg                                              24

<210> SEQ ID NO 8
<211> LENGTH: 25
<212> TYPE: DNA
<213> ORGANISM: Candida antarctica

<400> SEQUENCE: 8
gggtctgacc tacttcccca gtatc                                             25

<210> SEQ ID NO 9
<211> LENGTH: 25
<212> TYPE: DNA
<213> ORGANISM: Candida antarctica

<400> SEQUENCE: 9
gatactgggg aagtaggtca gaccc                                             25

<210> SEQ ID NO 10
<211> LENGTH: 21
<212> TYPE: DNA
<213> ORGANISM: Candida antarctica

<400> SEQUENCE: 10
cgatgagatt tccttcaatt t                                                 21

<210> SEQ ID NO 11
<211> LENGTH: 21
<212> TYPE: DNA
<213> ORGANISM: Candida antarctica

<400> SEQUENCE: 11
tctagaaagg tggcggccgc c                                                 21

<210> SEQ ID NO 12
<211> LENGTH: 22
<212> TYPE: DNA
<213> ORGANISM: Candida antarctica

<400> SEQUENCE: 12
gaagctggat tccatcatca tc                                                22

<210> SEQ ID NO 13
<211> LENGTH: 21
<212> TYPE: DNA
<213> ORGANISM: Candida antarctica

<400> SEQUENCE: 13
tctagaaagg tggcggccgc c                                                 21

<210> SEQ ID NO 14
<211> LENGTH: 1074
<212> TYPE: DNA
<213> ORGANISM: Bacillus subtilis
```

```
<400> SEQUENCE: 14
atgtctgtgc aggctgccgg aaaaagcagt acagaaaaga atacattgt cggatttaaa      60 cagacaatga gtgccatgag ttccgccaag aaaaaggatg ttatttctga aaaaggcgga    120
aaggttcaaa agcaatttaa gtatgttaac gcggccgcag caacattgga tgaaaaagct    180
gtaaaagaat tgaaaaaaga tccgagcgtt gcatatgtgg aagaagatca tattgcacat    240
gaatatgcgc aatctgttcc ttatggcatt tctcaaatta agcgccggc tcttcactct     300 caaggctaca caggctctaa cgtaaaagta gctgttatcg acagcggaat tgactcttct    360
catcctgact aaacgtcag aggcggagca agcttcgtac cttctgaaac aaacccatac     420
caggacggca gttctcacgg tacgcatgta gccggtacga ttgccgctct aataactca     480 atcggtgttc tgggcgttag cccaagcgca tcattatatg cagtaaaagt gcttgattca    540
acaggaagcg gccaatatag ctggattatt aacggcattg agtgggccat tccaacaat     600 atggatgtta tcaacatgag ccttggcgga cctactggtt ctacagcgct gaaaacagtc    660
gttgacaaag ccgtttccag cggtatcgtc gttgctgccg cagccggaaa cgaaggttca    720
tccggaagca caagcacagt cggctaccct gcaaaatatc cttctactat tgcagtaggt    780
gcggtaaaca gcagcaacca aagagcttca ttctccagcg caggttctga gcttgatgtg    840
atggctcctg cgctgtccat ccaaagcaca cttcctggag gcacttacgg cgcttataac    900
ggaacgtcca tggcgactcc tcacgttgcc ggagcagcag cgttaattct ttctaagcac    960
ccgacttgga caaacgcgca agtccgtgat cgtttagaaa gcactgcaac atatcttgga   1020
aactctttct actatggaaa agggttaatc aacgtacaag cagctgcaca ataa          1074

<210> SEQ ID NO 15
<211> LENGTH: 357
<212> TYPE: PRT
<213> ORGANISM: Bacillus subtilis

<400> SEQUENCE: 15
```

Met Ser Val Gln Ala Ala Gly Lys Ser Thr Glu Lys Lys Tyr Ile
1               5                   10                  15

Val Gly Phe Lys Gln Thr Met Ser Ala Met Ser Ser Ala Lys Lys
                20                  25                  30

Asp Val Ile Ser Glu Lys Gly Gly Lys Val Gln Lys Gln Phe Lys Tyr
            35                  40                  45

Val Asn Ala Ala Ala Ala Thr Leu Asp Glu Lys Ala Val Lys Glu Leu
        50                  55                  60

Lys Lys Asp Pro Ser Val Ala Tyr Val Glu Glu Asp His Ile Ala His
65                  70                  75                  80

Glu Tyr Ala Gln Ser Val Pro Tyr Gly Ile Ser Gln Ile Lys Ala Pro
                85                  90                  95

Ala Leu His Ser Gln Gly Tyr Thr Gly Ser Asn Val Lys Val Ala Val
                100                 105                 110

Ile Asp Ser Gly Ile Asp Ser Ser His Pro Asp Leu Asn Val Arg Gly
            115                 120                 125

Gly Ala Ser Phe Val Pro Ser Glu Thr Asn Pro Tyr Gln Asp Gly Ser
        130                 135                 140

Ser His Gly Thr His Val Ala Gly Thr Ile Ala Ala Leu Asn Asn Ser
145                 150                 155                 160

Ile Gly Val Leu Gly Val Ser Pro Ser Ala Ser Leu Tyr Ala Val Lys
                165                 170                 175

```
-continued

Val Leu Asp Ser Thr Gly Ser Gly Gln Tyr Ser Trp Ile Ile Asn Gly
            180                 185                 190

Ile Glu Trp Ala Ile Ser Asn Asn Met Asp Val Ile Asn Met Ser Leu
        195                 200                 205

Gly Gly Pro Thr Gly Ser Thr Ala Leu Lys Thr Val Asp Lys Ala
    210                 215                 220

Val Ser Ser Gly Ile Val Ala Ala Ala Gly Asn Glu Gly Ser
225                 230                 235                 240

Ser Gly Ser Thr Ser Thr Val Gly Tyr Pro Ala Lys Tyr Pro Ser Thr
                245                 250                 255

Ile Ala Val Gly Ala Val Asn Ser Ser Asn Gln Arg Ala Ser Phe Ser
            260                 265                 270

Ser Ala Gly Ser Glu Leu Asp Val Met Ala Pro Gly Val Ser Ile Gln
        275                 280                 285

Ser Thr Leu Pro Gly Gly Thr Tyr Gly Ala Tyr Asn Gly Thr Ser Met
    290                 295                 300

Ala Thr Pro His Val Ala Gly Ala Ala Leu Ile Leu Ser Lys His
305                 310                 315                 320

Pro Thr Trp Thr Asn Ala Gln Val Arg Asp Arg Leu Glu Ser Thr Ala
                325                 330                 335

Thr Tyr Leu Gly Asn Ser Phe Tyr Tyr Gly Lys Gly Leu Ile Asn Val
            340                 345                 350

Gln Ala Ala Gln
        355

<210> SEQ ID NO 16
<211> LENGTH: 269
<212> TYPE: PRT
<213> ORGANISM: Bacillus subtilis

<400> SEQUENCE: 16

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190
```

```
Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                    245                 250                 255

Tyr Gly Ser Gly Leu Val Asn Ala Glu Ala Ala Thr Arg
                260                 265

<210> SEQ ID NO 17
<211> LENGTH: 275
<212> TYPE: PRT
<213> ORGANISM: Bacillus subtilis

<400> SEQUENCE: 17

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
        130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Cys Met Ala Thr
        210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275
```

-continued

```
<210> SEQ ID NO 18
<211> LENGTH: 266
<212> TYPE: PRT
<213> ORGANISM: Bacillus subtilis

<400> SEQUENCE: 18

Ala Lys Cys Val Ser Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Ala Gly Gly Ala
        35                  40                  45

Ser Phe Val Pro Ser Glu Thr Asn Pro Phe Gln Asp Asn Asn Ser His
    50                  55                  60

Gly Thr His Val Ala Gly Thr Val Leu Ala Val Ala Pro Ser Ala Ser
65                  70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
    130                 135                 140

Gly Asn Glu Gly Thr Ser Gly Ser Ser Ser Thr Val Gly Tyr Pro Gly
145                 150                 155                 160

Lys Tyr Pro Ser Val Ile Ala Val Gly Ala Val Asp Ser Ser Asn Gln
                165                 170                 175

Arg Ala Ser Phe Ser Ser Val Gly Pro Glu Leu Asp Val Met Ala Pro
            180                 185                 190

Gly Val Ser Ile Cys Ser Thr Leu Pro Gly Asn Lys Tyr Gly Ala Lys
        195                 200                 205

Ser Gly Thr Ser Met Ala Ser Pro His Val Ala Gly Ala Ala Ala Leu
    210                 215                 220

Ile Leu Ser Lys His Pro Asn Trp Thr Asn Thr Gln Val Arg Ser Ser
225                 230                 235                 240

Leu Glu Asn Thr Thr Thr Lys Leu Gly Asn Ser Phe Tyr Tyr Gly Lys
                245                 250                 255

Gly Leu Ile Asn Val Gln Ala Ala Ala Gln
            260                 265

<210> SEQ ID NO 19
<211> LENGTH: 22
<212> TYPE: DNA
<213> ORGANISM: Bacillus subtilis

<400> SEQUENCE: 19
ccgagcgttg catatgtgga ag                                          22

<210> SEQ ID NO 20
<211> LENGTH: 54
<212> TYPE: DNA
<213> ORGANISM: Bacillus subtilis

<400> SEQUENCE: 20
ttaggatcct taatgatgat gatgatgatg ttgtgcagct gcttgtacgt tgat      54
```

<210> SEQ ID NO 21
<211> LENGTH: 27
<212> TYPE: DNA
<213> ORGANISM: Bacillus subtilis

<400> SEQUENCE: 21
ggctctaacg tatatgtagc tgttatc                              27

<210> SEQ ID NO 22
<211> LENGTH: 27
<212> TYPE: DNA
<213> ORGANISM: Bacillus subtilis

<400> SEQUENCE: 22
gataacagct acatatacgt tagagcc                              27

<210> SEQ ID NO 23
<211> LENGTH: 27
<212> TYPE: DNA
<213> ORGANISM: Bacillus subtilis

<400> SEQUENCE: 23
ttaattcttt cttaccaccc gacttgg                              27

<210> SEQ ID NO 24
<211> LENGTH: 28
<212> TYPE: DNA
<213> ORGANISM: Bacillus subtilis

<400> SEQUENCE: 24
ccaagtcggg tggtaagaaa gaattaac                             28

<210> SEQ ID NO 25
<211> LENGTH: 25
<212> TYPE: DNA
<213> ORGANISM: Bacillus subtilis

<400> SEQUENCE: 25
gacagcggaa tttactcttc tcatc                                25

<210> SEQ ID NO 26
<211> LENGTH: 25
<212> TYPE: DNA
<213> ORGANISM: Bacillus subtilis

<400> SEQUENCE: 26
gatgagaaga gtaaattccg ctgtc                                25

<210> SEQ ID NO 27
<211> LENGTH: 27
<212> TYPE: DNA
<213> ORGANISM: Bacillus subtilis

<400> SEQUENCE: 27
caaagcacac tttatggagg cacttac                              27

<210> SEQ ID NO 28
<211> LENGTH: 26
<212> TYPE: DNA
<213> ORGANISM: Bacillus subtilis

<400> SEQUENCE: 28
taagtgcctc cataaagtgt gctttg                               26

<210> SEQ ID NO 29
<211> LENGTH: 28
<212> TYPE: DNA
<213> ORGANISM: Bacillus subtilis

<400> SEQUENCE: 29
ggctaccctg catattatcc ttctacta                    28

<210> SEQ ID NO 30
<211> LENGTH: 27
<212> TYPE: DNA
<213> ORGANISM: Bacillus subtilis

<400> SEQUENCE: 30
agtagaagga taatatgcag ggtagcc                     27

<210> SEQ ID NO 31
<211> LENGTH: 27
<212> TYPE: DNA
<213> ORGANISM: Bacillus subtilis

<400> SEQUENCE: 31
agcgcaggtt cttatcttga tgtgatg                     27

<210> SEQ ID NO 32
<211> LENGTH: 27
<212> TYPE: DNA
<213> ORGANISM: Bacillus subtilis

<400> SEQUENCE: 32
catcacatca agataagaac ctgcgct                     27

<210> SEQ ID NO 33
<211> LENGTH: 26
<212> TYPE: DNA
<213> ORGANISM: Bacillus subtilis

<400> SEQUENCE: 33
ccataccagg actacagttc tcacgg                      26

<210> SEQ ID NO 34
<211> LENGTH: 26
<212> TYPE: DNA
<213> ORGANISM: Bacillus subtilis

<400> SEQUENCE: 34
ccgtgagaac tgtagtcctg gtatgg                      26

<210> SEQ ID NO 35
<211> LENGTH: 26
<212> TYPE: DNA
<213> ORGANISM: Bacillus subtilis

<400> SEQUENCE: 35
aagtgcttga ttatacagga agcggc                      26

<210> SEQ ID NO 36
<211> LENGTH: 26
<212> TYPE: DNA
<213> ORGANISM: Bacillus subtilis

<400> SEQUENCE: 36
gccgcttcct gtataatcaa gcactt                      26

```
<210> SEQ ID NO 37
<211> LENGTH: 24
<212> TYPE: DNA
<213> ORGANISM: Bacillus subtilis

<400> SEQUENCE: 37
gcgccggctc tttactctca aggc                                              24

<210> SEQ ID NO 38
<211> LENGTH: 25
<212> TYPE: DNA
<213> ORGANISM: Bacillus subtilis

<400> SEQUENCE: 38
agccttgaga gtaaagagcc ggcgc                                             25

<210> SEQ ID NO 39
<211> LENGTH: 27
<212> TYPE: DNA
<213> ORGANISM: Bacillus subtilis

<400> SEQUENCE: 39
ctgggcgtta gctatagcgc atcatta                                           27

<210> SEQ ID NO 40
<211> LENGTH: 27
<212> TYPE: DNA
<213> ORGANISM: Bacillus subtilis

<400> SEQUENCE: 40
taatgatgcg ctatagctaa cgcccag                                           27

<210> SEQ ID NO 41
<211> LENGTH: 27
<212> TYPE: DNA
<213> ORGANISM: Bacillus subtilis

<400> SEQUENCE: 41
gatgtgatgg cttatggcgt gtccatc                                           27

<210> SEQ ID NO 42
<211> LENGTH: 27
<212> TYPE: DNA
<213> ORGANISM: Bacillus subtilis

<400> SEQUENCE: 42
gatggacacg ccataagcca tcacatc                                           27
```